United States Patent [19]
Debs et al.

[11] Patent Number: 5,641,662
[45] Date of Patent: Jun. 24, 1997

[54] TRANSFECTION OF LUNG VIA AEROSOLIZED TRANSGENE DELIVERY

[75] Inventors: Robert James Debs, Mill Valley; Ning Zhu, El Cerrito, both of Calif.

[73] Assignee: The Regents of the University of California, Oakland, Calif.

[21] Appl. No.: 29,022

[22] Filed: Mar. 10, 1993

Related U.S. Application Data

[63] Continuation-in-part of Ser. No. 972,135, Nov. 5, 1992, which is a continuation-in-part of Ser. No. 809,291, Dec. 17, 1991, abandoned.

[51] Int. Cl.$^6$ .......................... C12N 15/64; C12N 15/87; A61K 48/00; A61K 9/127
[52] U.S. Cl. .................... 435/172.1; 435/172.3; 435/320.1; 424/450; 514/44; 128/200.14; 128/200.24; 536/24.1; 436/71
[58] Field of Search .................... 514/44; 424/450; 435/172.1, 172.3, 320.1; 935/62, 54, 55; 128/200.14, 200.24; 536/24.1; 436/71

[56] References Cited

U.S. PATENT DOCUMENTS

| | | | |
|---|---|---|---|
| 3,826,255 | 7/1974 | Havstad et al. | 128/194 |
| 4,046,146 | 9/1977 | Rosskamp et al. | 128/266 |
| 4,253,468 | 3/1981 | Lehmbeck | 128/726 |
| 4,268,460 | 5/1981 | Boiarski et al. | 261/1 |
| 4,394,448 | 7/1983 | Szoka et al. | 435/172 |
| 4,510,929 | 4/1985 | Bordoni et al. | 128/200.14 |
| 4,649,911 | 3/1987 | Knight et al. | 128/200.21 |
| 4,804,678 | 2/1989 | Augstein et al. | 514/456 |
| 4,946,787 | 8/1990 | Eppstein et al. | 435/240.2 |
| 5,240,842 | 8/1993 | Mets | 435/172.3 |
| 5,240,846 | 8/1993 | Collins et al. | 435/240.1 |
| 5,264,618 | 11/1993 | Felgnet et al. | 560/224 |

FOREIGN PATENT DOCUMENTS

| | | |
|---|---|---|
| 0446017A1 | 9/1991 | European Pat. Off. |
| WO90/11092 | 10/1990 | WIPO |
| WO91/02796 | 3/1991 | WIPO |
| WO91/06309 | 5/1991 | WIPO |
| WO91/17773 | 11/1991 | WIPO |

OTHER PUBLICATIONS

Brigham et al., Am. J. Med. Sci., vol. 298 (1989) pp. 278–281.
Canonico et al. (1991) Expression of a CMV promoter driven human α1–antitrypsin gene in cultured lung endothelial cells and in the lungs of rabbits, *Clinica Research*, 39: 219(A).
Debs et al. (1990) Biodistribution, tissue reaction and lung retention of pentamidine aerosolized as three different salts, *Am. Rev. Respir. Dis.*, 142: 1164–1167.
Felgner et al. (1987) Lipofection: A highly efficient, Lipid–mediated DNA–transfection procedure. *Proc. Natl. Acad. Sci. USA*, 84: 7413–7417.
Hubbard et al. (1989) Fate of aerosolized recombinant DNA–produced α1–antitrypsin: Use of the epithelial surface of the lower respiratory tract to administer protein of therapeutic importance. *Proc. Natl. Acad. Sci. USA*, 86:680–684.
Hug. et al. (1991) Liposomes for the transformation of eukaryotic cells. *Biochem. et Biophysica Acta*, 1097: 1–17.
Malone et al. (1989) Cationic liposome–mediated RNA transfection., *Proc. Natl. Acad. Sci. USA*, 86: 6077–6081.
Mannino et al. (1988) Liposome mediated gene transfer. *Biotechniques*, 6: 682–690.
Rosenfeld et al. (1991) Adenovirus–mediated transfer of a recombinant α1–antitrypsin gene to the lung epithelium in vivo. *Science*, 252: 431–434.
Brigham et al. (1989) Expression of a prokaryotic gene in cultured lung endothelial cells after lipofection with a plasmid vector. *Am. J. Respir. Cell. Mol. Biol.* 1: 95: 100.
Debs et al. (1987) *Amer. Rev. Respir. Dis,.* 135: 731–737.
Debs et al. (1987) *Antimicrob. Agents Chemother.*, 31: 37–42.
Debs et al. (1988) *J. Immunol.*, 140: 3482–3488.
Gregoriadis (1985) *Trends in Biotechnology*, 3(9): 235–241.
Hazinski et al. (1991) *Am. J. Respir. Cell. Mol. Biol.* 4: 206–209.
Holden (1991) *Science*, 253: 964–965.
Huang et al. (1990) *Molecular and Cellular Biology*, 10: 1805–1810.
Leoung et al. (1990) *N. Eng. J. Med.*, 323: 769–775.
Montgomery et al. (1989) *Chest*, 95: 747–751.
Montgomery et al. (1987) *Lancet* 11: 480–483.
Nabel et al. (1990) *Science*, 249: 1285–1288.
Straubinger et al. (1993) *Meth. Enzymol.*, 101: 512–527.
Wolff et al. (1990) *Science* 247: 1465–1468.
Debs et al. (1990) Regulation of gene expression in vivo by liposome–mediated delivery of a purified transcription factor, *J. Biol. Chem.*, 265: 10189.
Knowles et al. (1990) A pilot study of aerosolized amiloride for the treatment of lung disease in cystic fibrosis. *N. Engl. J. Med.*, 322: 1189–1194.
Mercer, (1981) Production of therapeutic aerosols. *Chest*, 80(6): 813.
Mercer et al. (1968) Operating characteristics of some compressed–air nebulizers., *Am. Ind. Hyg. Assoc. J.*, 29: 66–78.
Rose et al. (1991) A new cationic liposome reagent mediating nearly quantitative transfection of animal cells. *Biotechniques*, 10: 520–525.

*Primary Examiner*—Charles C. P. Rories
*Attorney, Agent, or Firm*—Townsend and Townsend and Crew

[57] ABSTRACT

Methods and compositions for producing a mammal capable of expressing an exogenously supplied gene in cells of the airway are disclosed. Lipid carrier-nucleic acid complexes are prepared then delivered via aerosol to the lung airway. The invention provides a direct method for transforming pulmonary cells as a means for treating disorders of the lung as for providing a means for delivering substances systematically following expression in the lung.

15 Claims, 38 Drawing Sheets
(17 of 45 Drawing(s) in Color)

pBC12/CMV/IL-2
(Cullen, B. R., Cell 46:973-982, 1986)

Partial digestion with Nde I, fill in, gel purify the band at 4570bp.
Ligation, screen clone deleted a fragment from Nde I(1755) to NdeI (1917)

pZN15

Partial digestion with EcoR I, fill in, gel purify the band cut once by EcoR I.
Ligation, screen for clone lost EcoRI (1631)

pZN26                pZN22

Sma I+EcoR I             PpuM I, fill in, then EcoR I
Gel purify the large     Gel purify the fragment
fragment                 containing intron and polyA
                         site (665bp)

Ligation

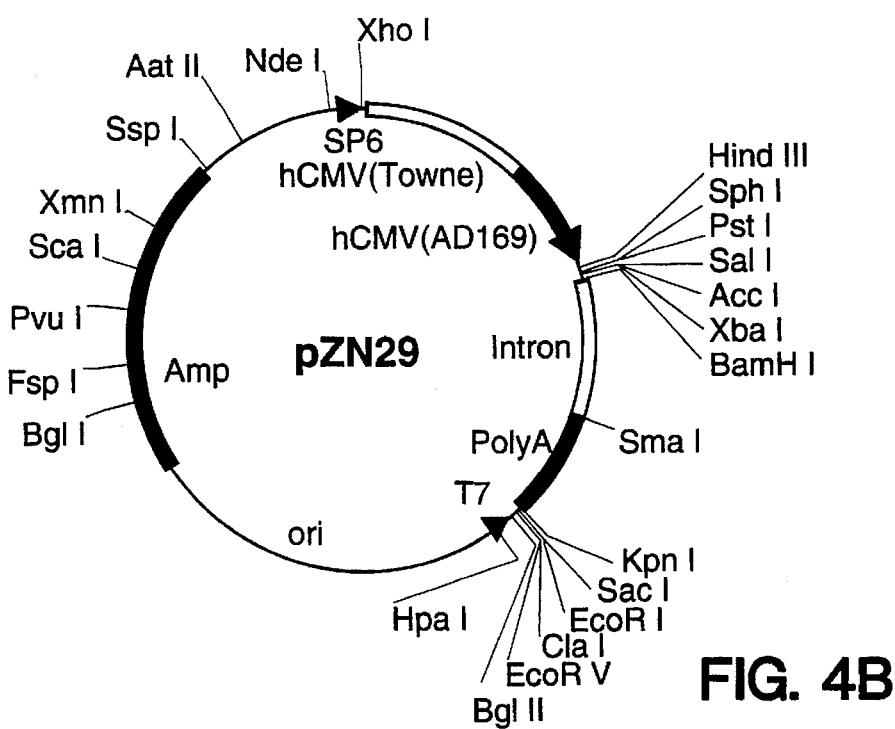

FIG. 4B

HCMV (Towne) -> Full Restriction Map

DNA sequence  616 b.p.  ggcgaccgccca ... agtgacgtaagt  linear  (SEQ ID NO:1)

Positions of Restriction Endonucleases sites (unique sites underlined)

```
                                Mae II
                                Aha II
                                Aat II                        Mae III
                                HinC II         Mae II  Mae III
                                  |    |    |     |       |
GGCGACCGCCCAGCGACCCCGCCCCGTTGACGTCAATAGTGACGTATGTTCCCATAGTAACGCCAATAGGGACTTTCCAT    80
CCGCTGGCGGGTCGCTGGGGCGGGGCAACTGCAGTTATCACTGCATACAAGGGTATCATTGCGGTTATCCCTGAAAGGTA
                           |    |    |                                  |
                          26   29   30                                  57
                               29
```

```
                              Bgl I         Rsa I        Nde I
                                |             |            |
TGACGTCAATGGGTGGAGTATTTACGGTAAACTGCCCACTTGGCAGTACATCAAGTGTATCATATGCCAAGTCCGCCCCC   160
ACTGCAGTTACCCACCTCATAAATGCCATTTGACGGGTGAACCGTCATGTAGTTCACATAGTATACGGTTCAGGCGGGGG
 |  |                                         |            |
82  82                                       114          126            141
83
Mae II
Aha II
Aat II
```

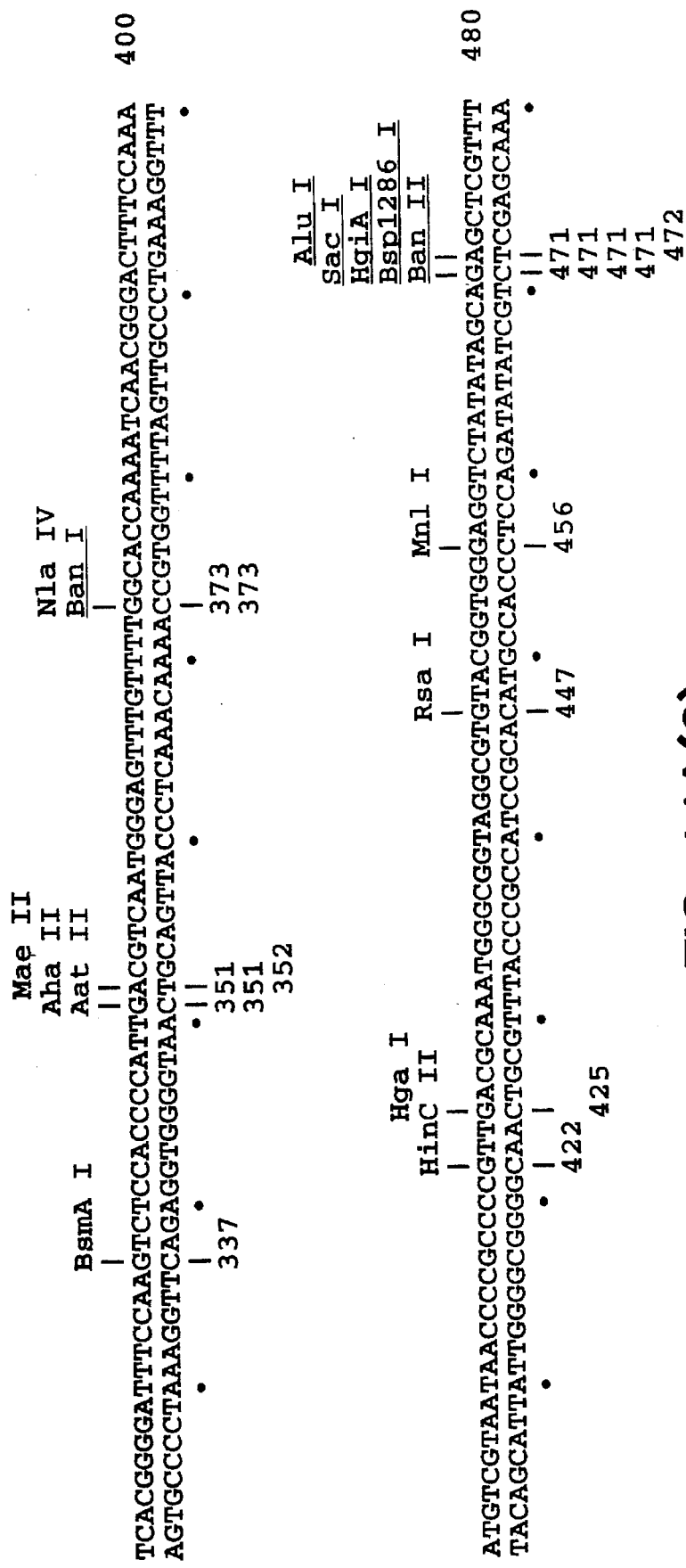
FIG. 11A(3)

```
           ScrF I
           Nci I
           Msp I
           Hpa II
           Bcn I
           Hae III
           Gdi II
           Eag I
           Eae I                    Hinf I           Mae II
           Fnu4H I        BstU I                     Mae III
           | | |             |          |              | |
           GCGGCCGGGAACGGTGCATTGGAACGCGGATTCCCCGTGCCAAGAGTGACGTAAGT  616
           CGCCGGCCCTTGCCACGTAACCTTGCGCCTAAGGGGCACGGTTCTCACTGCATTCA
           | | |             •          •              • •
           561                         585            606
           562                                        609
           562                585
           562                589
           563
           565
           565
           565
           565
           565
```

Restriction Endonucleases site usage

| | | | | | | |
|---|---|---|---|---|---|---|
| Aat II | 4 | BspH I | – | EcoR V | – | Mnl I | – | Rsr II | 3 |
| Acc I | – | BspM I | – | Esp I | – | Msc I | – | Sac I | – |
| Afl II | – | BspM II | – | Fnu4H I | 1 | Mse I | 1 | Sac II | 1 |
| Afl III | – | Bsr I | 1 | Fok I | 1 | Msp I | 1 | Sal I | – |
| Aha II | 5 | BssH II | – | Fsp I | – | Nae I | – | Sau3A I | 2 |
| Alu I | 1 | BstB I | – | Gdi II | 1 | Nar I | 1 | Sau96 I | 2 |

FIG. 11A(6)

| Enzyme | | Enzyme | | Enzyme | | Enzyme | |
|---|---|---|---|---|---|---|---|
| Alw I | 1 | BstE II | | Gsu I | 1 | Nci I | 2 |
| AlwN I | – | BstN I | 1 | Hae I | – | Nco I | 1 |
| Apa I | – | BstU I | 2 | Hae II | 2 | Nde I | 1 |
| ApaL I | – | BstX I | – | Hae III | 2 | Nhe I | – |
| Ase I | – | BstY I | – | Hga I | 1 | Nla III | 2 |
| Asp718 | – | Bsu36 I | – | HgiA I | – | Nla IV | 2 |
| Ava I | 1 | Cfr10 I | – | HgiE II | 2 | Not I | – |
| Ava II | – | Cla I | 1 | Hha I | – | Nru I | – |
| Avr II | – | Dde I | – | HinC II | – | Nsi I | – |
| BamH I | 1 | Dpn I | 2 | HinD III | 2 | Nsp7524 I | – |
| Ban I | 1 | Dra I | – | Hinf I | – | NspB II | 1 |
| Ban II | 1 | Dra III | – | HinP I | 2 | NspH I | – |
| Bbe I | – | Drd I | – | Hpa I | – | Pac I | – |
| Bbv I | – | Dsa I | 2 | Hpa II | 2 | PaeR7 I | – |
| Bbv II | 1 | Eae I | 1 | Hph I | 1 | PflM I | – |
| Bcl I | – | Eag I | 1 | Kpn I | – | Ple I | 1 |
| Bcn I | 2 | Ear I | – | Mae I | 1 | Pml I | – |
| Bgl I | 2 | Eco47 III | – | Mae II | – | PpuM I | – |
| Bgl II | – | Eco57 I | – | Mae III | 7 | Pst I | – |
| BsaA I | 1 | EcoN I | – | Mbo I | 3 | Pvu I | – |
| Bsm I | – | EcoO109 I | – | Mbo II | 2 | Pvu II | – |
| BsmA I | 2 | EcoR I | – | Mlu I | 1 | Rsa I | 5 |
| Bsp1286 I | 1 | EcoR II | – | Mme I | – | | |

| | | | | | | Sca I | – |
| | | | | | | ScrF I | 3 |
| | | | | | | Sec I | 2 |
| | | | | | | SfaN I | 1 |
| | | | | | | Sfi I | – |
| | | | | | | Sma I | – |
| | | | | | | SnaB I | 1 |
| | | | | | | Spe I | – |
| | | | | | | Sph I | – |
| | | | | | | Spl I | – |
| | | | | | | Ssp I | – |
| | | | | | | Stu I | – |
| | | | | | | Sty I | – |
| | | | | | | Taq I | 1 |
| | | | | | | Tth111 I | – |
| | | | | | | Tth111 II | – |
| | | | | | | Xba I | – |
| | | | | | | Xca I | – |
| | | | | | | Xho I | – |
| | | | | | | Xcm I | – |
| | | | | | | Xma I | – |
| | | | | | | Xmn I | – |

| Enzyme | site | Use | Site position (Fragment length) Fragment order |
|---|---|---|---|
| Alu I | ag/ct | 1 | 1( 471) 1 472( 145) 2 |
| Alw I | ggatc | 1 | 1( 548) 1 549( 68) 2 |
| Ava II | g/gwcc | 4/5 1 | 1( 543) 1 544( 73) 2 |
| Ban I | g/gyrcc | 1 | 1( 372) 1 373( 244) 2 |

FIG. 11A(7)

| Enzyme | Site | | | | | | | |
|---|---|---|---|---|---|---|---|---|
| Ban II | grgcy/c | | 1 | 1( | 470) | 1 | 471( | 146) | 2 |
| Bbv II | gaagac | 2/6 | 1 | 1( | 533) | 1 | 534( | 83) | 2 |
| BsaA I | yac/gtr | | 1 | 1( | 245) | 2 | 246( | 371) | 1 |
| Bsp1286 I | gdgch/c | | 1 | 1( | 470) | 1 | 471( | 146) | 2 |
| Bsr I | actgg | 1/-1 | 1 | 1( | 202) | 2 | 203( | 414) | 1 |
| BstN I | cc/wgg | | 1 | 1( | 497) | 1 | 498( | 119) | 2 |
| Eae I | y/ggccr | | 1 | 1( | 561) | 1 | 562( | 55) | 2 |
| Eag I | c/ggccg | | 1 | 1( | 561) | 1 | 562( | 55) | 2 |
| EcoR II | /ccwgg | | 1 | 1( | 497) | 1 | 498( | 119) | 2 |
| Fnu4H I | gc/ngc | | 1 | 1( | 560) | 1 | 561( | 56) | 2 |
| Fok I | ggatg | 9/13 | 1 | 1( | 508) | 1 | 509( | 108) | 2 |
| Gdi II | yggccg | -5/-1 | 1 | 1( | 561) | 1 | 562( | 55) | 2 |
| Gsu I | ctggag | 16/14 | 1 | 1( | 498) | 1 | 499( | 118) | 2 |
| Hgi A I | gwgcw/c | | 1 | 1( | 470) | 1 | 471( | 146) | 2 |
| Hph I | ggtga | 8/7 | 1 | 1( | 271) | 2 | 272( | 345) | 1 |
| Mae I | c/tag | | 1 | 1( | 190) | 2 | 191( | 426) | 2 |
| Mbo II | gaaga | 8/7 | 1 | 1( | 533) | 1 | 534( | 83) | 2 |
| Nco I | c/catgg | | 1 | 1( | 267) | 2 | 268( | 349) | 1 |
| Nde I | ca/tatg | | 1 | 1( | 140) | 2 | 141( | 476) | 1 |
| NspB II | cmg/ckg | | 1 | 1( | 558) | 1 | 559( | 58) | 2 |
| Ple I | gagtc | 4/5 | 1 | 1( | 317) | 2 | 318( | 299) | 2 |
| Sac I | gagct/c | | 1 | 1( | 470) | 1 | 471( | 146) | 2 |
| Sac II | ccgc/gg | | 1 | 1( | 558) | 1 | 559( | 58) | 2 |
| SfaN I | gcatc | 5/9 | 1 | 1( | 274) | 2 | 275( | 342) | 2 |
| SnaB I | tac/gta | | 1 | 1( | 245) | 2 | 246( | 371) | 1 |
| Sty I | c/cwwgg | | 1 | 1( | 267) | 2 | 268( | 349) | 1 |
| Bcn I | ccs/gg | | 2 | 1( | 540) | 1 | 541( | 24) | 3 |
| Bgl II | gccnnnn/nggc | | 2 | 1( | 113) | 2 | 114( | 441) | 1 |
| BsmA I | gtctc | 1/5 | 2 | 1( | 336) | 1 | 337( | 165) | 2 | 502( | 115) | 3 |
| BstU I | cg/cg | | 2 | 1( | 559) | 1 | 560( | 25) | 3 | 585( | 32) | 2 |
| Dpn I | ga/tc | | 2 | 1( | 492) | 1 | 493( | 56) | 3 | 549( | 68) | 2 |
| Dsa I | c/crygg | | 2 | 1( | 267) | 2 | 268( | 291) | 1 | 559( | 58) | 3 |
| Hae III | gg/cc | | 2 | 1( | 183) | 2 | 184( | 379) | 1 | 563( | 54) | 3 |
| Hga I | gacgc | 5/10 | 2 | 1( | 424) | 1 | 425( | 79) | 3 | 504( | 113) | 2 |

| | | | | | | |
|---|---|---|---|---|---|---|
| HinC II | gty/rac | 2 | 1( 25) 3 | 26( 396) 1 | 422( 195) 2 |
| Hinf I | g/antc | 2 | 1( 317) 1 | 318( 271) 2 | 589( 28) 3 |
| Hpa II | c/cgg | 2 | 1( 540) 1 | 541( 24) 3 | 565( 52) 2 |
| Mbo I | /gatc | 2 | 1( 492) 1 | 493( 56) 3 | 549( 68) 2 |
| Msp I | c/cgg | 2 | 1( 540) 1 | 541( 24) 3 | 565( 52) 2 |
| Nci I | cc/sgg | 2 | 1( 540) 1 | 541( 24) 3 | 565( 52) 2 |
| Nla III | catg/ | 2 | 1( 208) 2 | 209( 60) 3 | 269( 348) 1 |
| Nla IV | ggn/ncc | 2 | 1( 372) 1 | 373( 170) 2 | 543( 74) 3 |
| Sau3A I | /gatc | 2 | 1( 492) 1 | 493( 56) 3 | 549( 68) 2 |
| Sau96 I | g/gncc | 2 | 1( 183) 2 | 184( 360) 1 | 544( 73) 3 |
| Sec I | c/cnngg | 2 | 1( 267) 2 | 268( 291) 1 | 559( 58) 3 |
| Mae III | /gtnac | 3 | 1( 38) 2 | 39( 18) 3 | 57( 549) 1 |
| | | | 606( 11) 4 | | |
| Mnl I | cctc | 3 | 1( 455) 1 | 456( 70) 2 | 526( 30) 4 |
| | | | 556( 61) 3 | | |
| ScrF I | cc/ngg | 3 | 1( 497) 1 | 498( 43) 3 | 541( 24) 4 |
| | | | 565( 52) 2 | | |
| Aat II | gacgt/c | 4 | 1( 28) 5 | 29( 53) 4 | 82( 83) 3 |
| | | | 165( 186) 2 | 351( 266) 1 | |
| Aha II | gr/cgyc | 5 | 1( 28) 6 | 29( 53) 5 | 82( 83) 4 |
| | | | 165( 186) 1 | 351( 153) 2 | 504( 113) 3 |
| Rsa I | gt/ac | 5 | 1( 125) 3 | 126( 80) 4 | 206( 33) 6 |
| | | | 239( 51) 5 | 290( 157) 2 | 447( 170) 1 |
| Mae II | a/cgt | 7 | 1( 29) 6 | 30( 12) 7 | 42( 41) 5 |
| | | | 83( 83) 3 | 166( 81) 4 | 247( 105) 2 |
| | | | 352( 257) 1 | 609( 8) 8 | |

98 sites found

No Sites found for the following Restriction Endonucleases

| | | | | | | |
|---|---|---|---|---|---|---|
| Dra III | cacnnn/gtg | | Nsp7524 I | r/catgy | | |
| Acc I | gt/mkac | | | | | |

FIG. 11A(8)

| | | | | | |
|---|---|---|---|---|---|
| Afl II | c/ttaag | Drd I | gacnnnn/nngtc | NspH I | rcatg/y |
| Afl III | a/crygt | Ear I | ctcttc 1/4 | Pac I | ttaat/taa |
| AlwN I | cagnnn/ctg | Eco47 III | agc/gct | PaeR7 I | c/tcgag |
| Apa I | gggcc/c | Eco57 I | ctgaag 16/14 | Pf1M I | ccannnn/ntgg |
| ApaL I | g/tgcac | EcoN I | cctnn/nnnagg | Pml I | cac/gtg |
| Ase I | at/taat | EcoO109 I | rg/gnccy | PpuM I | rg/gwccy |
| Asp718 | g/gtacc | EcoR I | g/aattc | Pst I | ctgca/g |
| Ava I | c/ycgrg | EcoR V | gat/atc | Pvu I | cgat/cg |
| Avr II | c/ctagg | Esp I | gc/tnagc | Pvu II | cag/ctg |
| BamH I | g/gatcc | Fsp I | tgc/gca | Rsr II | cg/gwccg |
| Bbe I | ggcgc/c | Hae I | wgg/ccw | Sal I | g/tcgac |
| Bbv I | gcagc 8/12 | Hae II | rgcgc/y | Sca I | agt/act |
| Bcl I | t/gatca | HgiE II | accnnnnnnggt | Sfi I | ggccnnnn/nggcc |
| Bgl II | a/gatct | Hha I | gcg/c | Sma I | ccc/ggg |
| Bsm I | gaatgc 1/-1 | HinD III | a/agctt | Spe I | a/ctagt |
| BspH I | t/catga | HinP I | g/cgc | Sph I | gcatg/c |
| BspM I | acctgc 4/8 | Hpa I | gtt/aac | Spl I | c/gtacg |
| BspM II | t/ccgga | Kpn I | ggtac/c | Ssp I | aat/att |
| BssH II | g/cgcgc | Mlu I | a/cgcgt | Stu I | agg/cct |
| BstB I | tt/cgaa | Mme I | tccrac 20/18 | Taq I | t/cga |
| BstE II | g/gtnacc | Msc I | tgg/cca | Tth111 I | gacn/nngtc |
| BstX I | ccannnnn/ntgg | Mse I | t/taa | Tth111 II | caarca 11/9 |
| BstY I | r/gatcy | Nae I | gcc/ggc | Xba I | t/ctaga |
| Bsu36 I | cc/tnagg | Nar I | gg/cgcc | Xca I | gta/tac |
| Cfr10 I | r/ccggy | Nhe I | g/ctagc | Xho I | c/tcgag |
| Cla I | at/cgat | Not I | gc/ggccgc | Xcm I | ccannnnn/nnnntgg |
| Dde I | c/tnag | Nru I | tcg/cga | Xma I | c/ccggg |
| Dra I | ttt/aaa | Nsi I | atgca/t | Xmn I | gaann/nnttc |

FIG. 11A(9)

```
*** Aligned sequences:
C1 ( 1f): |>u 1>++++++ ad169hcmv (930 bases)++++++>u 930>|
C2 ( 1f): |>u 1>++++++   hs5mie1 (616 bases)++++++>u 616>|

*** Alignment of first sequence with all others displayed
*** Key:
    UPPER CASE = aligned non-identical bases
    lower case = unaligned bases
    ---------- = aligned identical bases
    .......... = gap (SEQ ID
 NO:2) ad169hcmv : AATCAATATATTGGCCATTAGCCCATATTTATTCATTGGTTATATAGCCATAAATCAATATTGGC
(SEQ ID   hs5mie1 : ................................................................
 NO:3)

ad169hcmv : TATTGGCCATTGCATACGTTGTATCCATATCATAATATGTACATTTATATTGGCTCATGT
         hs5mie1 : ............................................................

ad169hcmv : CCAACATTACCGCCATGTTGACATTGATTATTGACTAGTTATTAATAGTAATCAATTACG
         hs5mie1 : ............................................................

ad169hcmv : GGGTCATTAGTTCATAGCCCATATATGGAGTTCCGCGTTACATAACTTACGGTAAATGGC
         hs5mie1 : ............................................................

ad169hcmv : CCGCCTGGCTGACCGCCCAACGACCCCCGCCCATTGACGTCAATAATGACGTATGTTCCC
         hs5mie1 : ---------------------G---------------G---------------------- ad169hcmv : ATAGTAACGCCAATAGGGACTTTCCATTGACGTCAATGGGTGGAGTATTTACGGTAAACT
         hs5mie1 : ------------------------------------------------------------
```

FIG. 11B(1)

```
ad169hcmv : GCCCACTTGGCAGTACATCAAGTGTATCATATGCCAAGTACGCCCCCTATTGACGTCAAT
hs5mie1   : ------------------------------C----------------------------- ad169hcmv : GACGGTAAATGGCCCGCCTGGCATTATGCCCAGTACATGACCTTATGGGACTTTCCTACT
hs5mie1   : ---------------------------A---------------C-----G---------- ad169hcmv : TGGCAGTACATCTACGTATTAGTCATCGCTATTACCATGGTGATGCGGTTTTGGCAGTAC
hs5mie1   : ------------------------------*----------------------------- ad169hcmv : ATCAATGGGCGTGGATAGCGGTTTGACTCACGGGGATTTCCAAGTCTCCACCCCATTGAC
hs5mie1   : -C---------------------------------------------------------- ad169hcmv : GTCAATGGGAGTTTGTTTTGGCACCAAAATCAACGGGACTTTCCAAAATGTCGTAACAAC
hs5mie1   : ------------------------------------------------T----------- ad169hcmv : TCCGCCCCATTGACGCAAATGGGCGGTAGGCGTGTACGGTGGGAGGTCTATATAAGCAGA
hs5mie1   : C------G----------------------------------------·----------- ad169hcmv : GCTCGTTTAGTGAACCGTCAGATCGCCTGGAGACGCCATCCACGCTGTTTTGACCTCCAT
hs5mie1   : ------------------------------------------------------------ ad169hcmv : AGAAGACACCGGGACCGATCCAGCCTCCGCGGCCGGGAACGGTGCATTGGAACGCGGATT
hs5mie1   : ------------------------------------------------------------ ad169hcmv : CCCCGTGCCAAGAGTGACGTAAGTACCGCCTATAGAGTCTATAGGCCCACCCCCTTGGCT
hs5mie1   : ·········································· ad169hcmv : TCTTATGCATGCTATACTGTTTTTGGCTTG
hs5mie1   : ··········································
```

FIG. 11B(2)

```
LOCUS        HS5IEE              930 bp ds-DNA             VRL       15-SEP-1989
DEFINITION   Human cytomegalovirus major immediate-early gene, enhancer.
ACCESSION    K03104
KEYWORDS     major immediate-early gene.
SOURCE       HCMV strain AD169.
  ORGANISM   Human cytomegalovirus
             Viridae; ds-DNA enveloped viruses; Herpesviridae;
             Betaherpesvirinae.
REFERENCE    1  (bases 1 to 930)
  AUTHORS    Boshart,M., Weber,F., Jahn,G., Dorsch-Haesler,K.,
             Fleckenstein,B. and Schaffner,W.
  TITLE      A very strong enhancer is located upstream of an immediate
             early gene of human cytomegalovirus
  JOURNAL    Cell 41, 521-530 (1985)
  STANDARD   full automatic
REFERENCE    2  (sites)
  AUTHORS    Zhang,X.-Y., Inamdar,N.M., Supakar,P.C., Wu,K., Ehrlich,M.
             and Ehrlich,K.C.
  TITLE      three MDBP sites in the immediate-early enhancer-promoter
             region of human cytomegalovirus
  JOURNAL    Virology 182, 865-869 (1991)
  STANDARD   full automatic
COMMENT      Draft entry and printed copy of sequence in [1] were kindly
             provided by M.Boshart, 24-OCT-1985.
```

FIG. 11B(3)

```
FEATURES             Location/Qualifiers
    misc_signal      214..620
                     /note="HCMV IE enhancer region"
    mRNA             738..>930
                     /note="HCMV IE mRNA"

BASE COUNT     233 A    228 C    211 G    258 T
ORIGIN      12 bp upstream of BalI site; .750 mu.
    1 AATCAAATATT GGCCATTAGC CATATATTC ATTGGTTATA TAGCATAAAT CAATATTGGC
   61 TATTGGCCAT TGCATACGTT GTATCCATAT CATAAATATGT ACATTTATAT TGGCTCATGT
  121 CCAACATTAC CGCCATGTTG ACATTGTTA TTGACTAGTT ATTAATAGTA ATCAATTACG
  181 GGGTCATTAG TTCATAGCCC ATATATGGAG TTCCGCGTTA CATAACTTAC GGTAAATGGC
  241 CCGCCTGGCT GACCGCCCAA CGACCCCCGC CCATTGACGT CAATAATGAC GTATGTTCCC
  301 ATAGTAACGC CAATAGGGAC TTTCCATTGA CGTCAATGGG TGGAGTATTT ACGGTAAACT
  361 GCCCACTTGG CAGTACATCA AGTGTATCAT ATGCCAAGTA CGCCCCCTAT TGACGTCAAT
  421 GACGGTAAAT GGCCCGCCTG GCATTATGCC CAGTACATGA CCTTATGGGA CTTTCCTACT
  481 TGGCAGTACA TCTACGTATT AGTCATCGCT ATTACCATGG TGATGCGGTT TTGGCAGTAC
  541 ATCAATGGGC GTGGATAGCG GTTTGACTCA CGGGGATTTC CAAGTCTCCA CCCCATTGAC
  601 GTCAATGGGA GTTTGTTTTG GCACCAAAAT CAACGGGACT TTCCAAAATG TCGTAACAAC
  661 TCCGCCCCAT TGACGCAAAT GGGCGGGTAGG CGTGTACGGT GGGAGGTCTA TATAAGCAGA
  721 GCTCGTTTAG TGAACCGTCA GATCGCCTGG AGACGCCATC CACGCTGTTT TGACCTCCAT
  781 AGAAGACACC GGGACCGATC CAGCCTCCGC GGCCGGGAAC GGTGCATTGG AACGCGGATT
  841 CCCCGTGCCA AGAGTGACGT AAGTACCGCC TATAGAGTCT ATAGGCCCAC CCCCTTGGCT
  901 TCTTATGCAT GCTATACTGT TTTTGGCTTG                                 (SEQ ID NO:2)
```

FIG. 11B(4)

| | | | |
|---|---|---|---|
| LOCUS | HS5MIE1 | 616 bp ds-DNA | VRL  15-SEP-1989 |
| DEFINITION | Human cytomegalovirus (Towne) major immediate-early (IE) gene, exon 1. | | |
| ACCESSION | K01484 K01090 | | |
| KEYWORDS | major immediate-early gene. | | |
| SEGMENT | 1 of 4 | | |
| SOURCE | Human cytomegalovirus (strain Towne) passed in primary human foreskin fibroblasts, DNA [1], clone pXEP22 [2]. | | |
| ORGANISM | Human cytomegalovirus<br>Viridae; ds-DNA enveloped viruses; Herpesviridae; Betaherpesvirinae. | | |
| REFERENCE | 1  (bases 460 to 616) | | |
| AUTHORS | Stenberg,R.M., Thomsen,D.R. and Stinski,M.F. | | |
| TITLE | Structural analysis of the major immediate early gene of human cytomegalovirus | | |
| JOURNAL | J. Virol. 49, 190-199 (1984) | | |
| STANDARD | full automatic | | |
| REFERENCE | 2  (bases 1 to 490) | | |
| AUTHORS | Thomsen,D.R., Stenberg,R.M., Goins,W.F. and Stinski,M.F. | | |
| TITLE | Promoter-regulatory region of the major immediate early gene of human cytomegalovirus | | |
| JOURNAL | Proc. Natl. Acad. Sci. U.S.A. 81, 659-663 (1984) | | |
| STANDARD | full automatic | | |
| COMMENT | IE region 1 gene is also known as the major IE gene. | | |

FIG. 11B(5)

(SEQ ID NO:3)

```
FEATURES             Location/Qualifiers
     prim_transcript 490..>616
                     /note="major IE mRNA"
     intron          611..>616
                     /note="major IE mRNA intron A"
BASE COUNT      144 A     165 C     162 G     145 T
ORIGIN     28 bp upstream of HincII site; 0.752 map units.
    1 GGGCGACCGCC CAGCGACCCC CGCCCGTTGA CGTCAATAGT GACGTATGTT CCCATAGTAA
   61 CGCCAATAGG GACTTTCCAT TGACGTCAAT GGGTGGAGTA TTTACGGTAA ACTGCCCACT
  121 TGGCAGTACA TCAAGTGTAT CATATGCCAA GTCCGCCCCC TATTGACGTC AATGACGGTA
  181 AATGGCCCGC CTAGCATTAT GCCCAGTACA TGACCTTACG GGAGTTTCCT ACTTGGCAGT
  241 ACATCTACGT ATTAGTCATC GCTATTACCA TGGTGATGCG GTTTTGGCAG TACACCAATG
  301 GGCGTGGATA TCACGGGGAT TTCCAAGTCT CCACCCCATT GACGTCAATG
  361 GGAGTTTGTT TTGGCACCAA AATCAACGGG ACTTTCCAAA ATGTCGTAAT AACCCCGCCC
  421 CGTTGACGCA AATGGGCGGT AGGCGTGTAC GGTGGGAGGT CTATATAGCA GAGCTCGTTT
  481 AGTGAACCGT CAGATCGCCT GGAGACGCCA TCCACGCTGT TTTGACCTCC ATAGAAGACA
  541 CCGGGACCGA TCCAGCCTCC GCGGCCGGGA ACGGTGCATT GGAACGCGGA TTCCCCGTGC
  601 CAAGAGTGAC GTAAGT
```

FIG. 11B(6)

HCMV (AD169) -> Full Restriction Map

DNA sequence    930 b.p.    aatcaatattgg ... gtttttggcttg    linear    (SEQ ID NO:4)

Positions of Restriction Endonucleases sites (unique sites underlined)

```
    Hae III
    Msc I                                                      Hae III
    Hae I                                                      Msc I
    Eae I                                                      Hae I
Ssp I                                        Ssp I             Eae I              Mae II
  |   |||                                      |                |||                 |          80
AATCAATATTGGCCATTAGCCATATTATTCATTGGTTATATAGCATAAATCAATATTGGCTATTGGCCATTGCATACGTT
TTAGTTATAACCGGTAATCGGTATAATAAGTAACCAATATATCGTATTTAGTTATAACCGATAACCGGTAACGTATGCAA
  |   |||                                                       |||                 |
  5   10                                                        64                  76
      10                                                        64
      10                                                        64
      11                                                        65

Mme I                              HinC II           Mae I
            Rsa I   Nla III                            Nla III           Spe I
              |       |                                  |                ||        160
GTATCCATATCATAATATGTACATTTATATTGGCTCATGTCCAACATTACCGCCATGTTGACATTGATTATTGACTAGTT
CATAGGTATAGTATTATACATGTAAATATAACCGAGTACAGGTTGTAATGGCGGTACAACTGTAACTAATAACTGATCAA
              |       |                                  |                ||
              99      116                                134               154
                      120                                137               155
```

FIG. 11C(1)

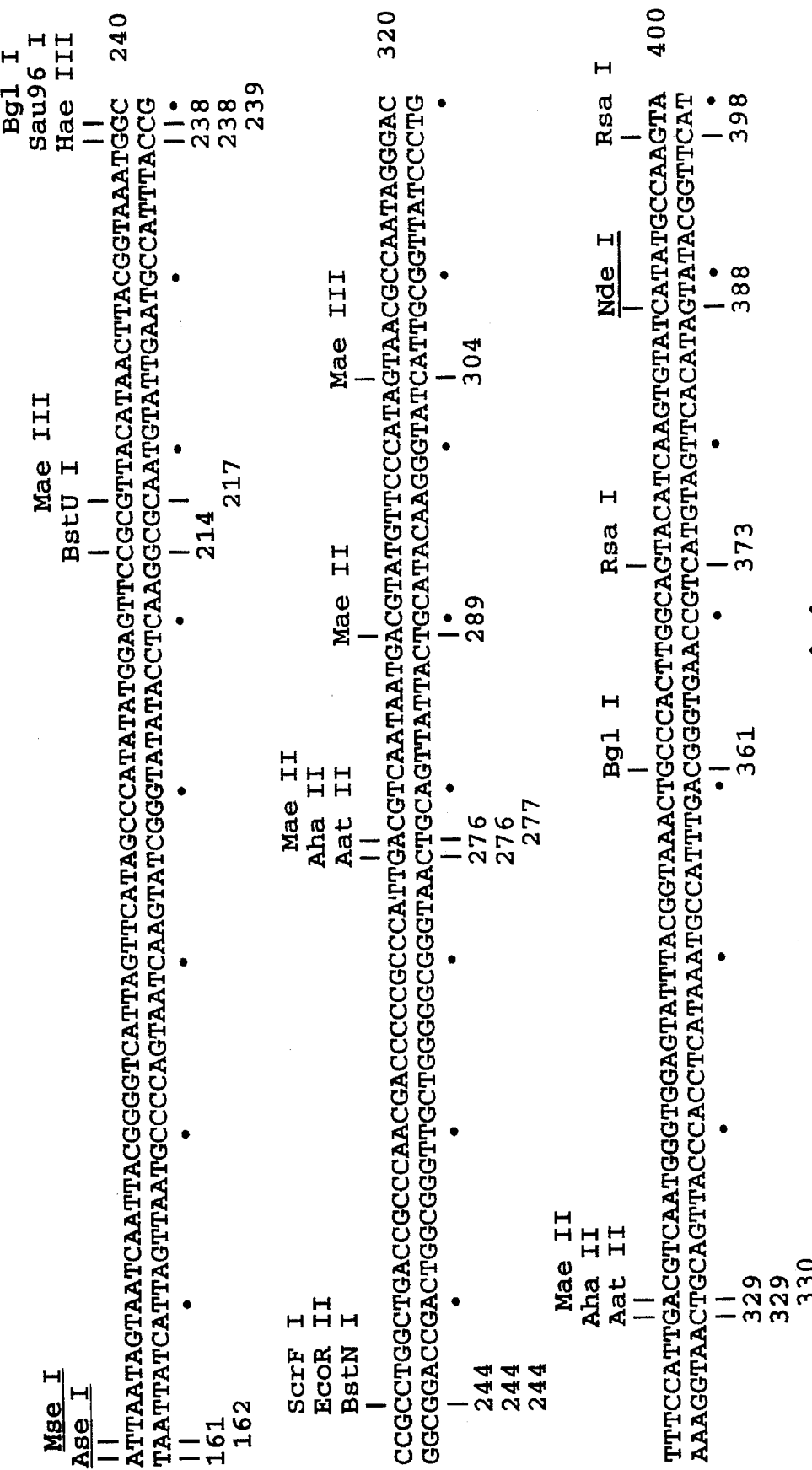
FIG. 11C(2)

FIG. 11C(3)

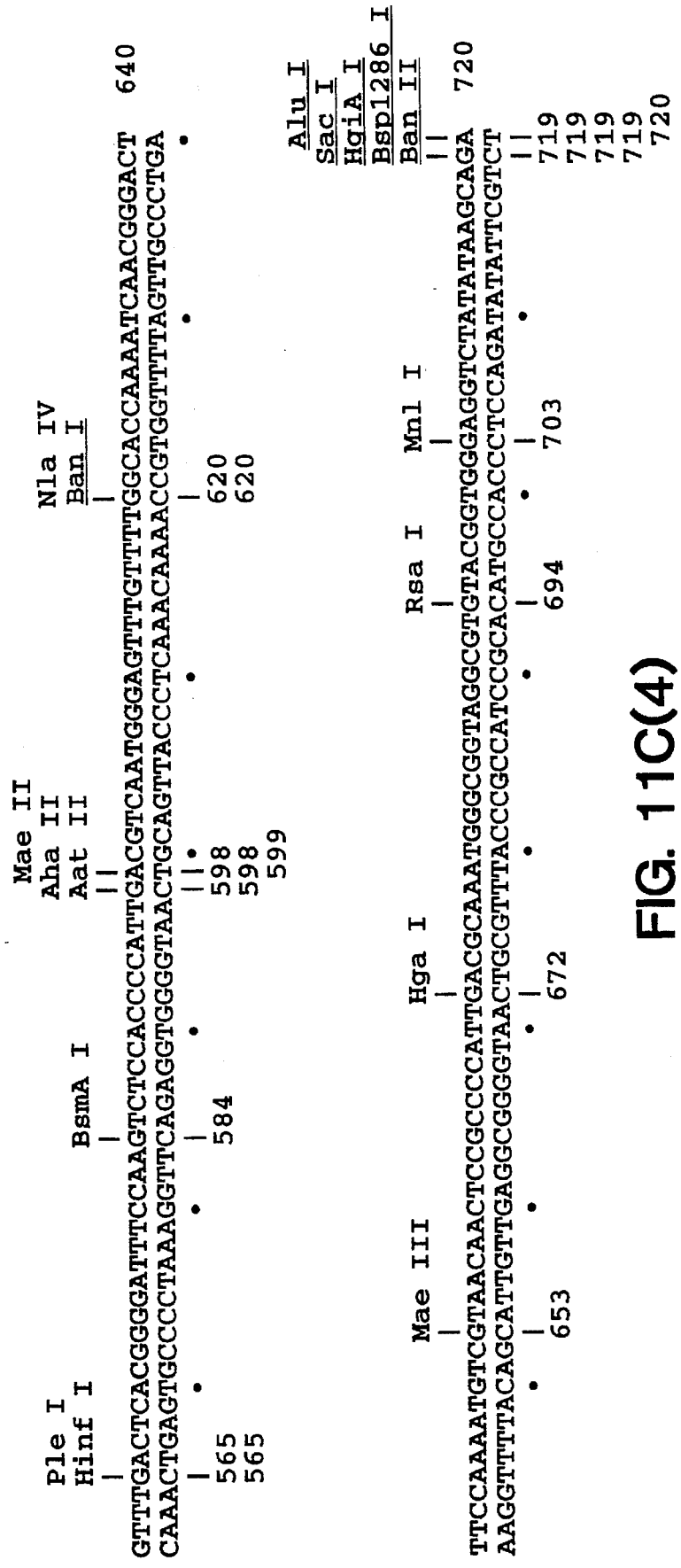
FIG. 11C(4)

FIG. 11C(5)

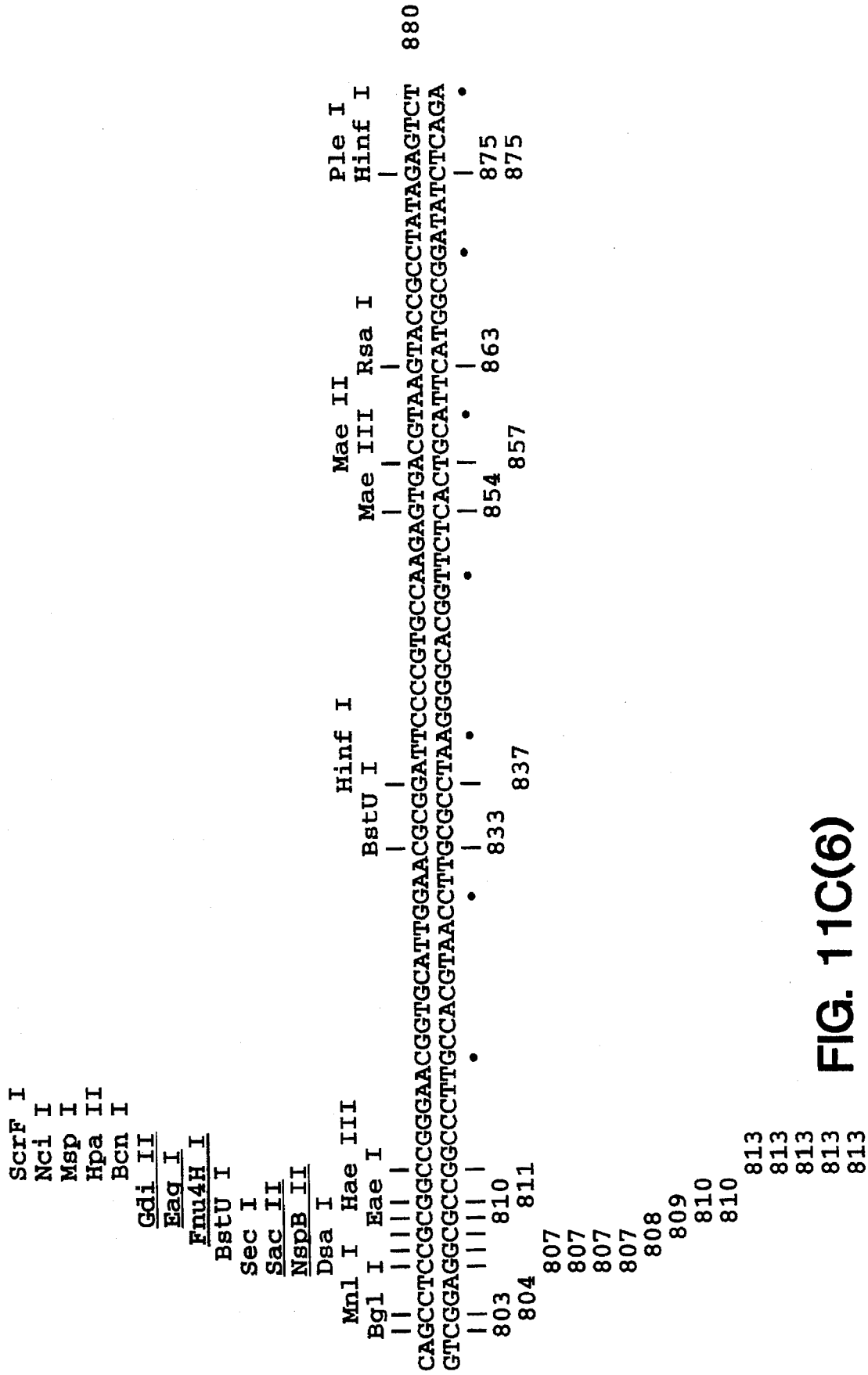
FIG. 11C(6)

```
                                            BstX I
                                        Sau96 I    Sty I          Nla III
                                        Hae III    Sec I          Sph I
                                                                  NspH I
                                                                  Nsp7524 I
                                                                  Nsi I
ATAGGCCCACCCCCTTGGCTTCTTATGCATGCTATATACTGTTTTTGGCTTG  930
TATCCGGGTGGGGGAACCGAAGAATACGTACGATATATGACAAAAACCGAAC
    |               |               |               |
   884             893             905             
   884             893             907             
   887                             907             
                                   907             
                                   908
```

FIG. 11C(7)

TRANSFECTION OF LUNG VIA AEROSOLIZED TRANSGENE DELIVERY

CROSS REFERENCE TO RELATED APPLICATIONS

This is a continuation-in-part of U.S. application Ser. No. 07/972,135, filed Nov. 5, 1992, which is a continuation-in-part of U.S. application Ser. No. 07/809,291, filed Dec. 17, 1991, now abandoned.

INTRODUCTION

1. Technical Field

The present invention relates to methods and compositions for producing a transgenic mammal which comprises an exogenously supplied gene in lung tissue. The gene is supplied by aerosolized delivery, particularly to the airways and alveoli of the lung.

2. Background

With the advent of molecular cloning techniques, an expanding array of genes with mutations responsible for important human diseases have been identified and isolated. To date, attempts to replace absent or mutated genes in human patients have relied on ex vivo techniques. Ex vivo techniques include, but are not limited to, transformation of cells in vitro with either naked DNA or DNA encapsulated in liposomes, followed by introduction into a host organ ("ex vivo" gene therapy). The criteria for a suitable organ include that the target organ for implantation is the site of the relevant disease, the disease is easily accessible, that it can be manipulated in vitro, that it is susceptible to genetic modification methods and ideally, it should contain either non-replicating cells or cycling stem cells to perpetuate a genetic correction. It also should be possible to reimplant the genetically modified cells into the organism in a functional and stable form. A further requirement for ex vivo gene therapy, if for example a retroviral vector is used, is that the cells be pre-mitotic; post-mitotic cells are refractory to infection with retroviral vectors. Exemplary of a target organ which meets the criteria for in vitro gene transfer is the mammalian bone marrow.

There are several drawbacks to ex vivo therapy. For example, if only differentiated, replicating cells are infected, the newly introduced gene function will be lost as those cells mature and die. Ex vivo approaches also can be used to transfect only a limited number of cells and cannot be used to transfect cells which are not first removed from the body.

Retroviruses, adenoviruses and liposomes have been used in animal model studies in attempts to increase the efficiency of gene transfer; DNA has been introduced into animals by intratracheal (IT), intravenous, intraperitoneal, intramuscular, and intraarterial injection. Expression of introduced genes, either complexed to cationic vectors or packaged in adenoviral vectors has been demonstrated in the lungs of rodents after IT instillation. However, IT injection is invasive and produces a non-uniform distribution of the instilled material; it also is too invasive to be performed repeatedly in humans. It therefore would be of interest to develop a non-invasive delivery technique which also results in deeper penetration of material into the lung than other methods, and can be used to deposit material evenly throughout the airways and alveoli. Such a delivery technique could be used as a means of treatment for genetic disorders, particularly of the lung, via generalized transgene expression in lung cells in vivo.

Relevant Literature

Hazinski, et al., *Am. J. Respir. Cell Mol. Biol.* (1991) 4: 206–209, relates to liposome-mediated gene transfer of DNA into the intact rodent lung. Three fusion gene constructs were complexed to cationic liposomes including (1) the chloramphenicol acetyltransferase ("CAT") gene linked to a Rous sarcoma virus ("RSV") promoter; (2) the CAT gene linked to a mouse mammary tumor virus ("MMTV") promoter; and (3) a cytomegalovirus-β-galactosidase ("CMV-β-gal") fusion gene. The liposome/DNA complexes were instilled into the cervical trachea of rats and detectable levels of gene expression observed.

Brigham et al., *Am. J. Med. Sci.* (1989) 298: 278–281, describes the in vivo transfection of murine lungs with the CAT gene using a liposome vehicle. Transfection was accomplished by intravenous, intratracheal or intraperitoneal injection. Both intravenous and intratracheal administration resulted in the expression of the CAT gene in the lungs. However, intraperitoneal administration did not. See, also Werthers, *Clinical Research* (1991) 39: (Abstract).

Canonico et al., *Clin. Res.* (1991) 39: 219A describes the expression of the human α-1 antitrypsin gene, driven by the CMV promoter, in cultured bovine lung epithelial cells. The gene was added to cells in culture using cationic liposomes. The experimenters also detected the presence of α-1 antitrypsin in histological sections of the lung of New Zealand white rabbits following the intravenous delivery of gene constructs complexed to liposomes. Yoshimura et al. disclose expression of the human cystic fibrosis transmembrane conductance regulator gene in mouse lung after intratracheal liposome-DNA gene transfer. Wolff et al., *Science* (1990) 247: 1465–1468 relates to direct transfer of the CAT, β-gal and luciferase genes into mouse skeletal muscle in vivo. Gene expression was observed in all three cases. Nabel et al., *Science* (1990) 249: 1285–1288, pertains to in vivo intra-arterial transfection of pigs with liposomes containing a β-gal expression plasmid. Site-specific gene expression was observed in the arterial wall. None of the above cited art, however, practices or teaches the use of aerosol administration to deliver genes directly to the lung. An example of a review article of human gene therapy procedures is: Anderson, *Science* (1992) 256: 808–813.

PCT/US90/01515, having International Publication No. WO 90/11092, describes a method for introducing naked DNA into muscle tissue. Debs et al. disclose pentamidine uptake in the lung by aerosolization and delivery in liposomes. *Am Rev Respir Dis* (1987) 135: 731–737.

SUMMARY

Methods and compositions are provided for producing a mammal which comprises an exogenously supplied nucleic acid in its lung cells. The method includes the steps of preparing a lipid carrier-nucleic acid mixture suitable for nebulization, nebulizing the mixture, and depositing the resulting nebulized mixture in the lung of a mammalian host of interest in an amount sufficient to transform cells contacted by the deposited nebulized mixture. The exogenously supplied nucleic acid generally is provided in an expression cassette and includes a coding sequence operably joined to transcriptional and translational regulatory sequences functional in the mammal. The methods and compositions find use particularly for in vivo gene therapy of pulmonary disorders.

BRIEF DESCRIPTION OF THE FIGURES

The file of this patent contains at least one drawing executed in color. Copies of this patent with color drawing(s) will be provided by the U.S. Patent and Trademark Office upon request and payment of the necessary fee.

FIG. 1 demonstrates that aerosol administration of pRSV-CAT-DOTMA: cholesterol complexes resulted in expression of the CAT gene in mouse lungs. Lanes 1-3 were derived from mice receiving no treatment; lanes 4-6 represent mice administered 0.5 mg pRSV-CAT with 1.0 µmole DOTMA-cholesterol liposomes; lanes 7-9 were derived from mice receiving 2.0 mg pRSV-CAT alone; and lanes 10-12 represent mice given 2.0 mg pRSV-CAT with 4.0 µmol DOTMA-cholesterol liposomes in a 2 to 1 molar ratio. The CAT gene is not normally present in mammalian cells; lanes 10-12 show spots indicative of CAT activity (the positive spots in lanes 10-11 are faint and do not reproduce well in the figure). The results thus indicate that the lung was successfully transfected by the pRSV-CAT DOTMA-cholesterol:liposome aerosol. The results also show that neither aerosol administration of the pRSV-CAT alone, nor a lower aerosol dose of pRSV-CAT: DOTMA-cholesterol complexes produce detectable expression of the CAT gene in mouse lungs. Thus, both the cationic liposome carrier, and a sufficient dose of DOTMA: liposome-RSV-CAT DNA complexes are required to produce transgene expression in the lung after aerosol administration. Maximum transgene expression is achieved by complexing the liposomes and DNA together at an appropriate ratio and in an appropriate diluent.

FIG. 2 shows the results of an experiment where mice were administered 12 mg of pCIS-CAT complexed to 24 µmoles of DOTMA/DOPE 1:1 liposomes. Lanes 1-3 show the results from animals administered the aerosol in an Intox-designed nose-only aerosol exposure chamber; lanes 4-7 are derived from mice exposed to the aerosol in a modified mouse cage; and lanes 8-10 show the results from animals placed in a smaller modified cage after being put in restrainers originally constructed for use in the Intox chamber.

FIGS. 3A, 3B, and 3C show construction of pZN13.

FIGS. 4A and 4B show construction of pZN29.

FIGS. 6A-6F show the results of immunostaining for intracellular CAT protein in lung sections from mice sacrificed 72 hours after receiving an aerosol containing 12 mg of pCIS-CAT plasmid complexed to 24 µmols of DOTMA-:DOPE liposomes (6A, 6B, 6C, 6D), or from untreated mice (6E, 6F). The section shown in 6D was treated with normal rabbit serum in place of anti-CAT antibody. Magnification: 6A, 6D (×50); 6B, 6C, 6E (×250).

Figure 7:
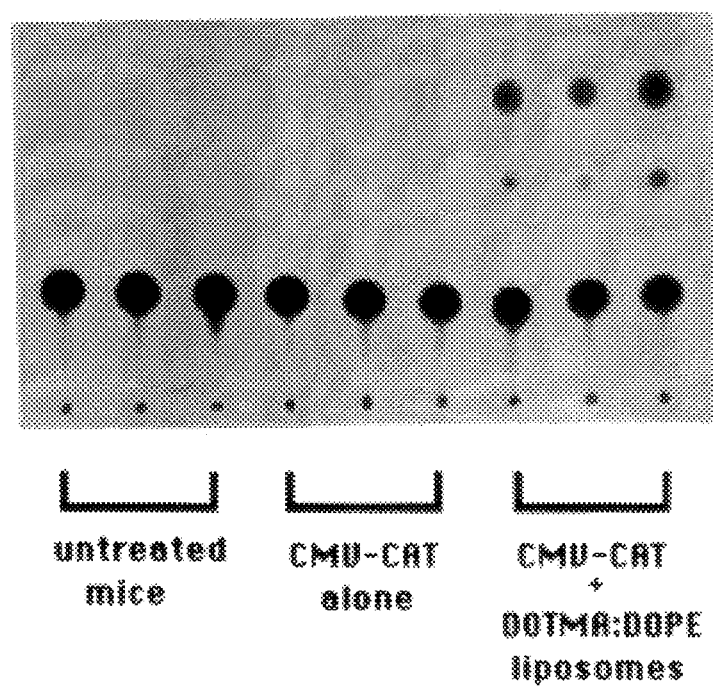

FIG. 7 shows CAT activity in lung extracts from mice sacrificed 72 hours after receiving an aerosol containing either 12 mg of CMV-CAT plasmid alone or 12 mg of CMV-CAT plasmid complex to 24 µmols of DOTMA-:DOPE (1:1) liposomes. Untreated mice were also assayed.

Figure 8A:
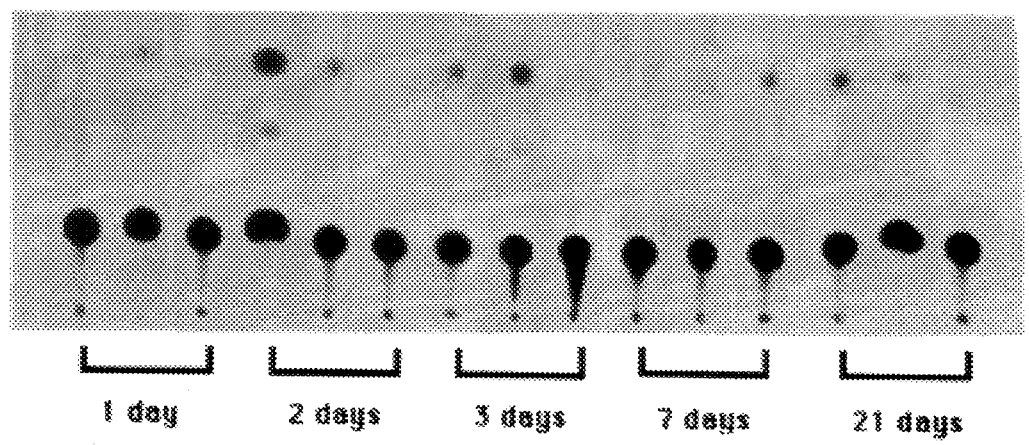
Figure 8B:
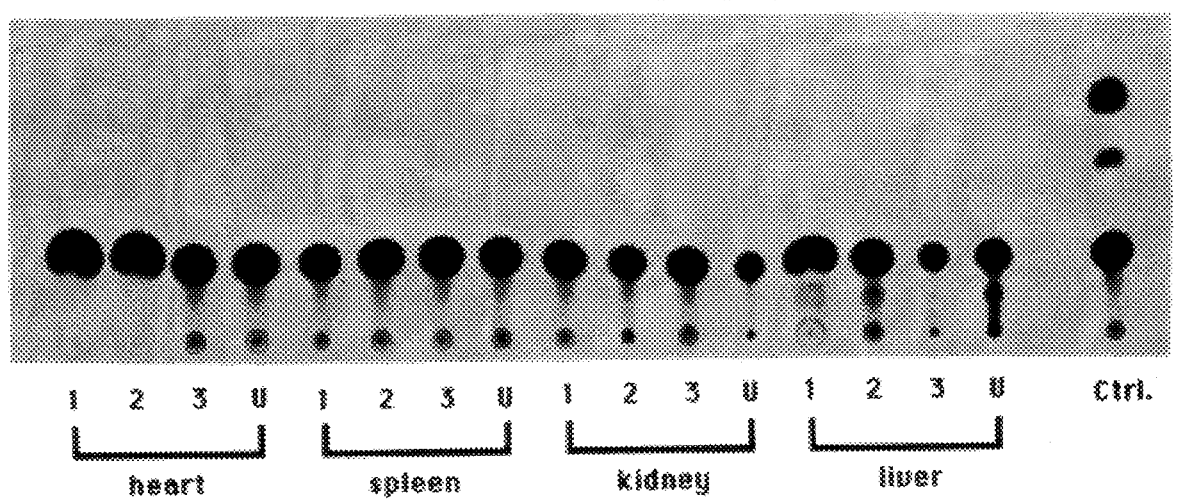

FIGS. 8A and 8B: FIG. 8A shows CAT activity in lung extracts from mice sacrificed from one to twenty-one days after receiving an aerosol containing 12 mg of pCIS-CAT plasmid complexed to 24 µmols of DOTMA:DOPE liposomes; and FIG. 8B shows CAT activity in several different tissue extracts from mice and indicates that expression of the transgene is lung-specific after aerosolization of DNA-liposome complexes into normal mice sacrificed at the three day time point in FIG. 8A. Control extract contains purified CAT enzyme.

Figure 9:
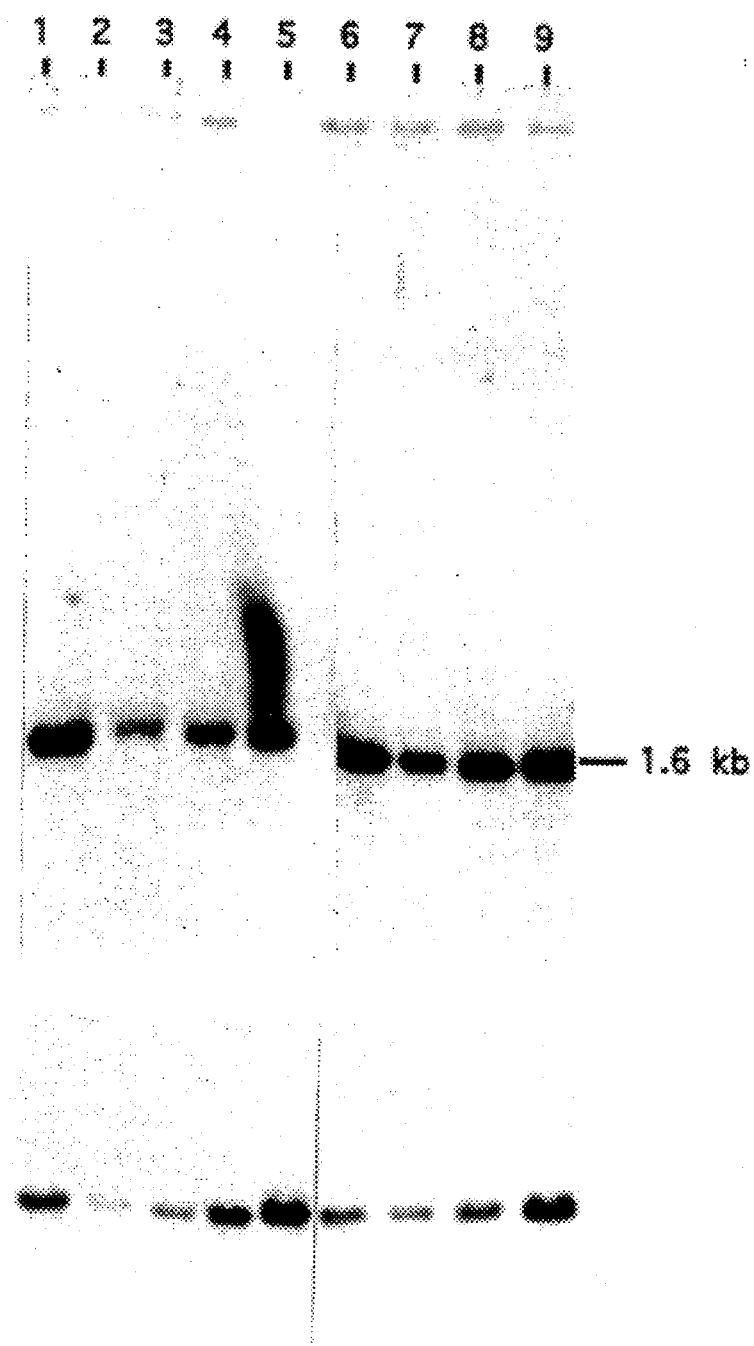

FIG. 9 shows Southern blot hybridization of genomic DNA from the lungs of mice sacrificed immediately after receiving an aerosol containing 12 mg of pCIS-CAT plasmid complexed to 24 µmols of DOTMA:DOPE liposomes (lanes 1-4, 6-9) and from an untreated control mouse (lane 5).

Samples were digested with the restriction enzyme HindIII and probed with a 1.6 kb CAT fragment (upper panel). The same membrane was hybridized with a 1.1 kb BSU 36-1 single copy probe from a mouse factor VIII. A genomic clone (lower panel).

Figure 10A:
Figure 10B:
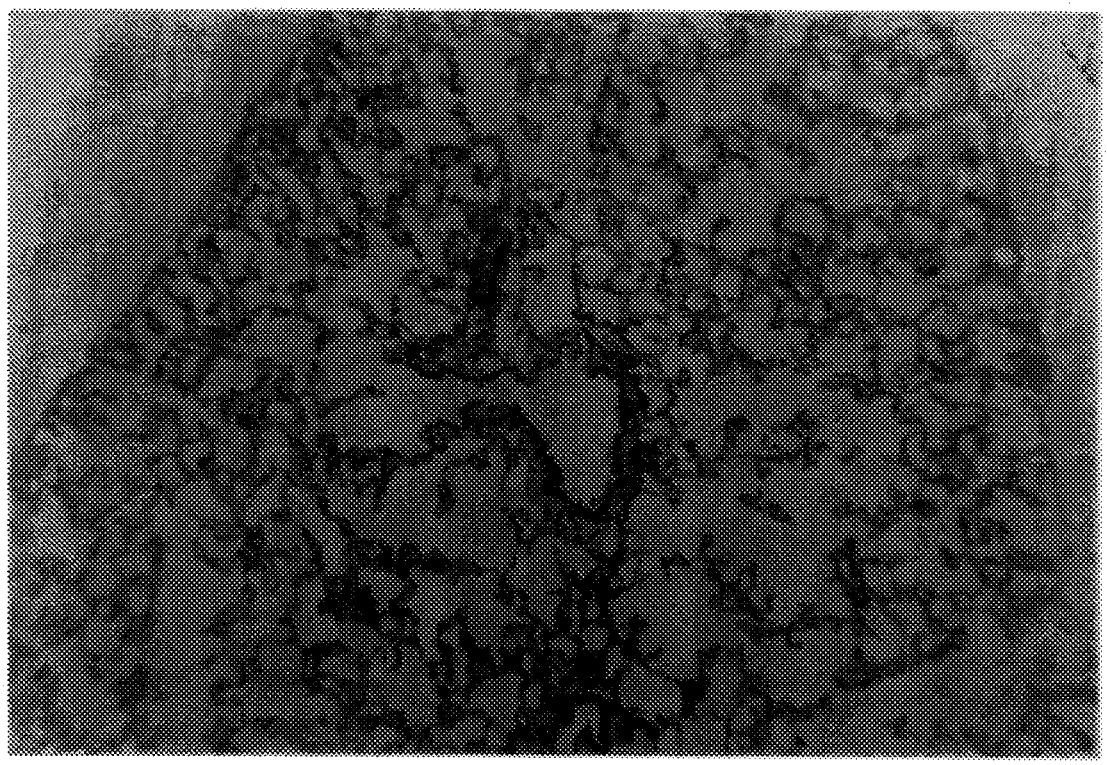
Figure 10C:
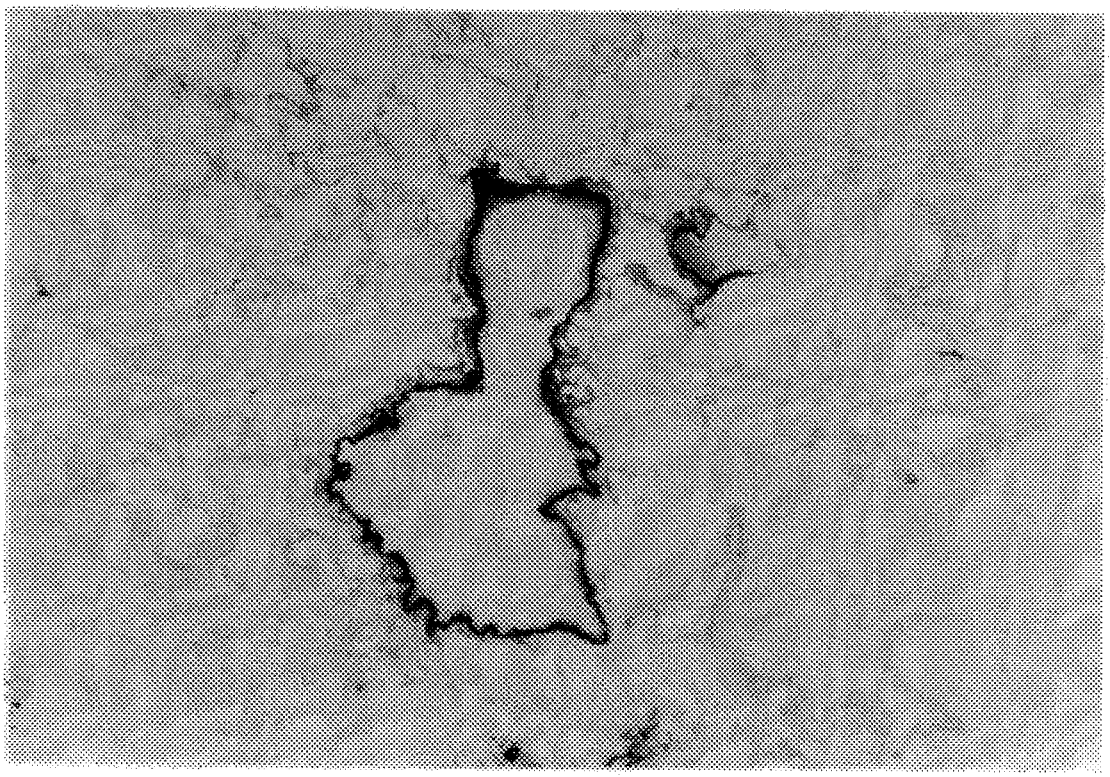
Figure 10D:
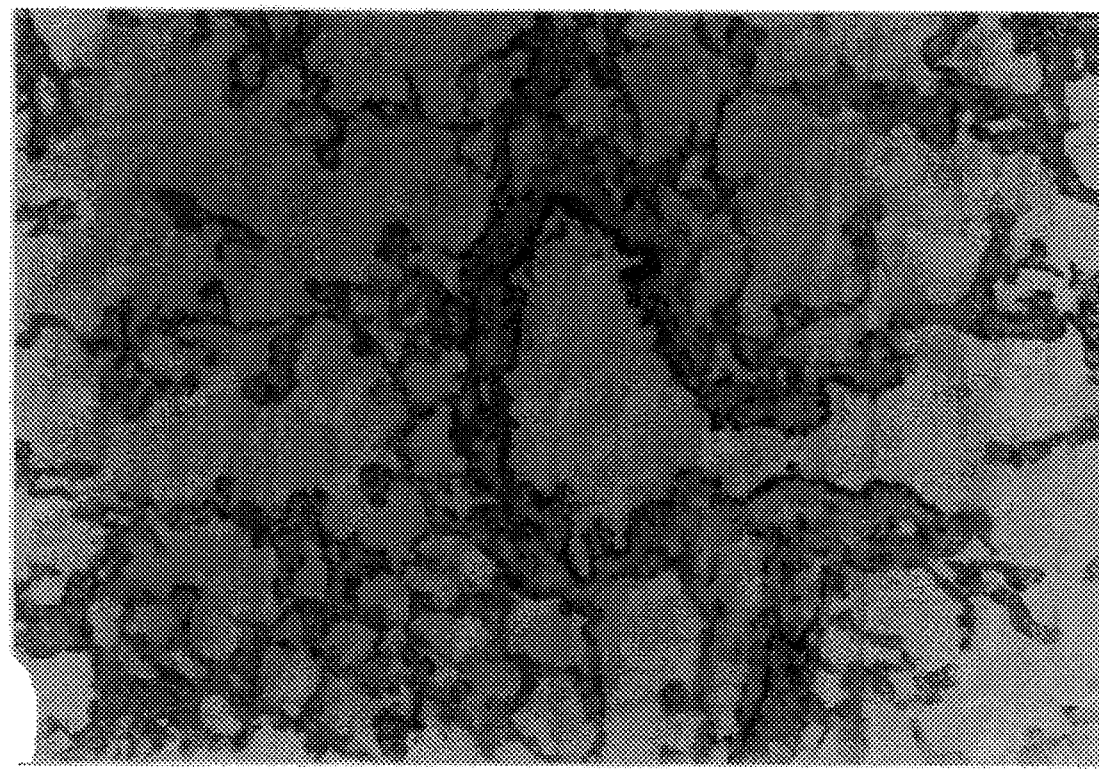
Figure 10E:
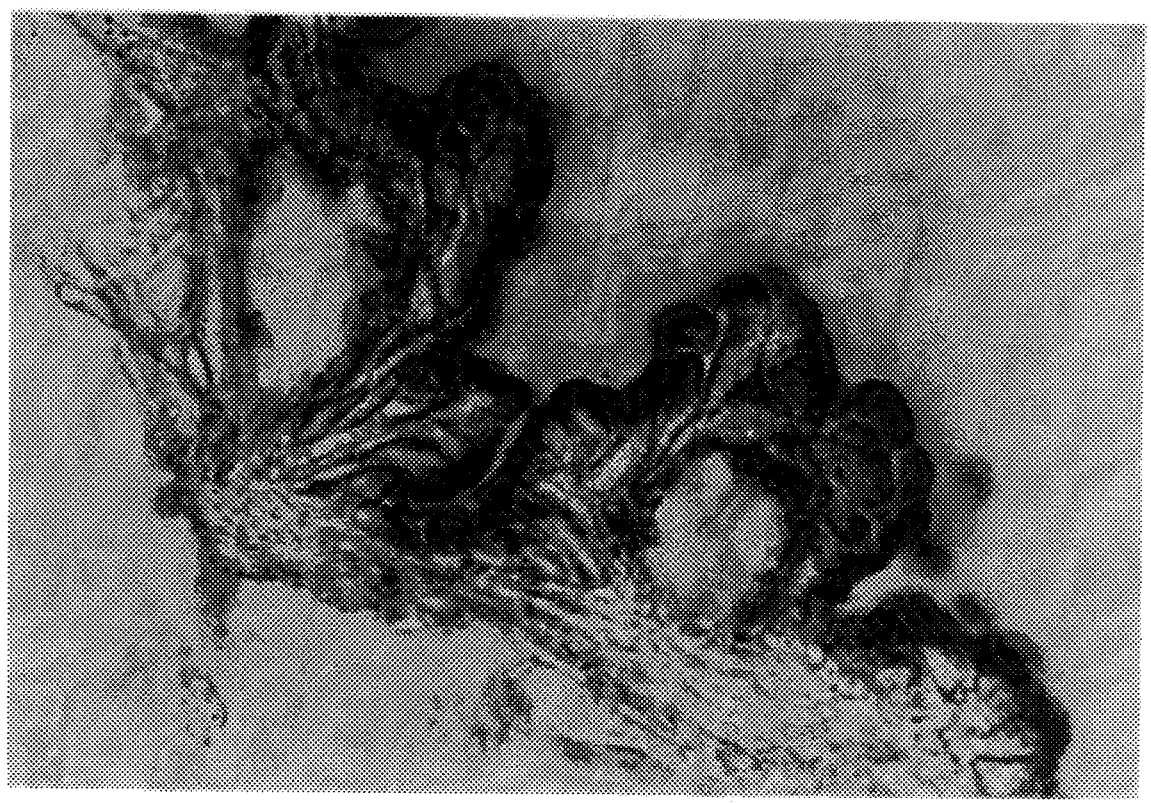

FIGS. 10A–10E show photomicrographs of frozen sections from lungs of control mice (FIGS. 10B and 10D) and mice treated with pZN32 complexed to DDAB:cholesterol (1:1) liposomes (FIGS. 10A, 10C, and 10E).

Figure 11A:
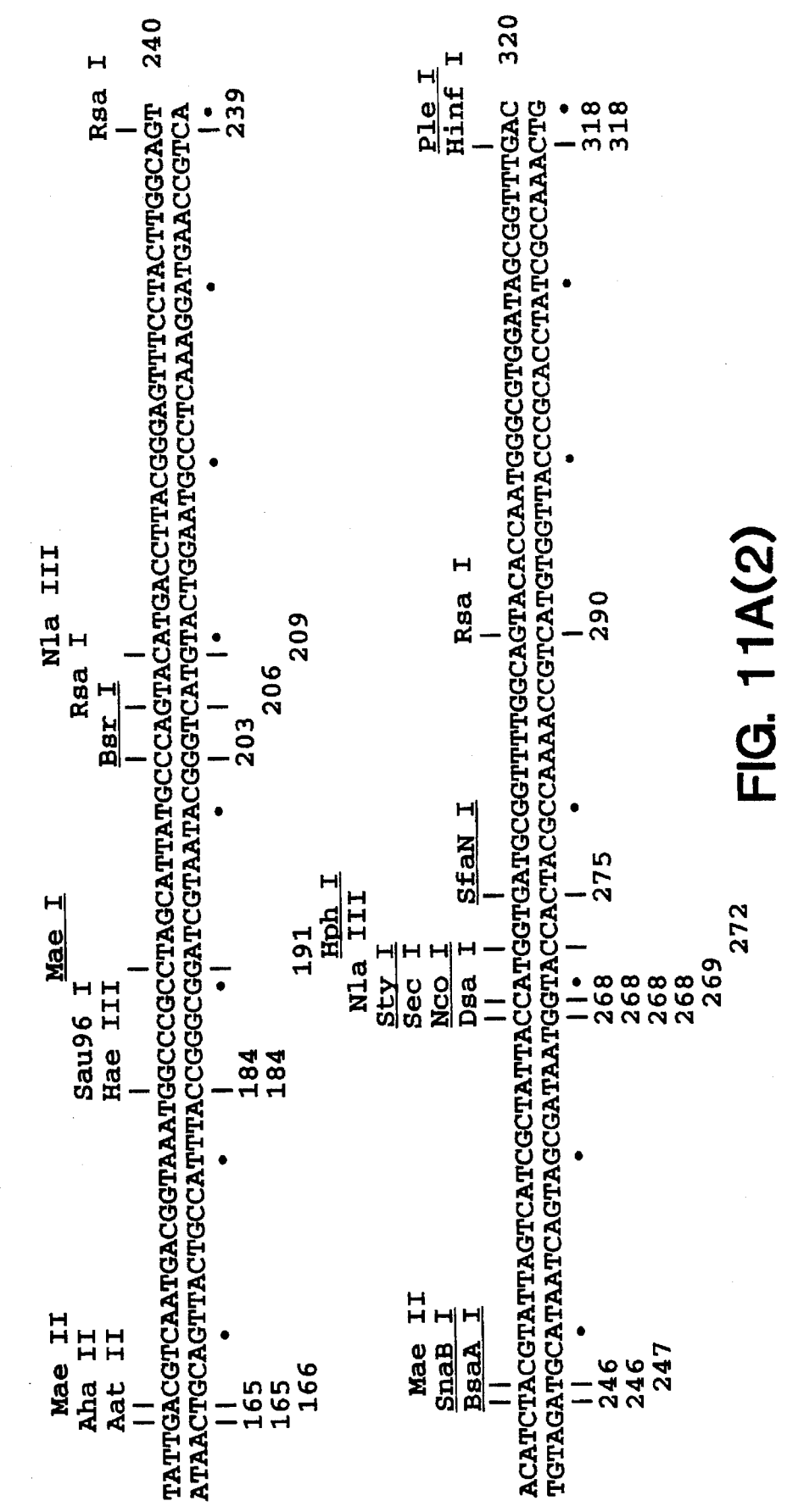
Figure 11A:
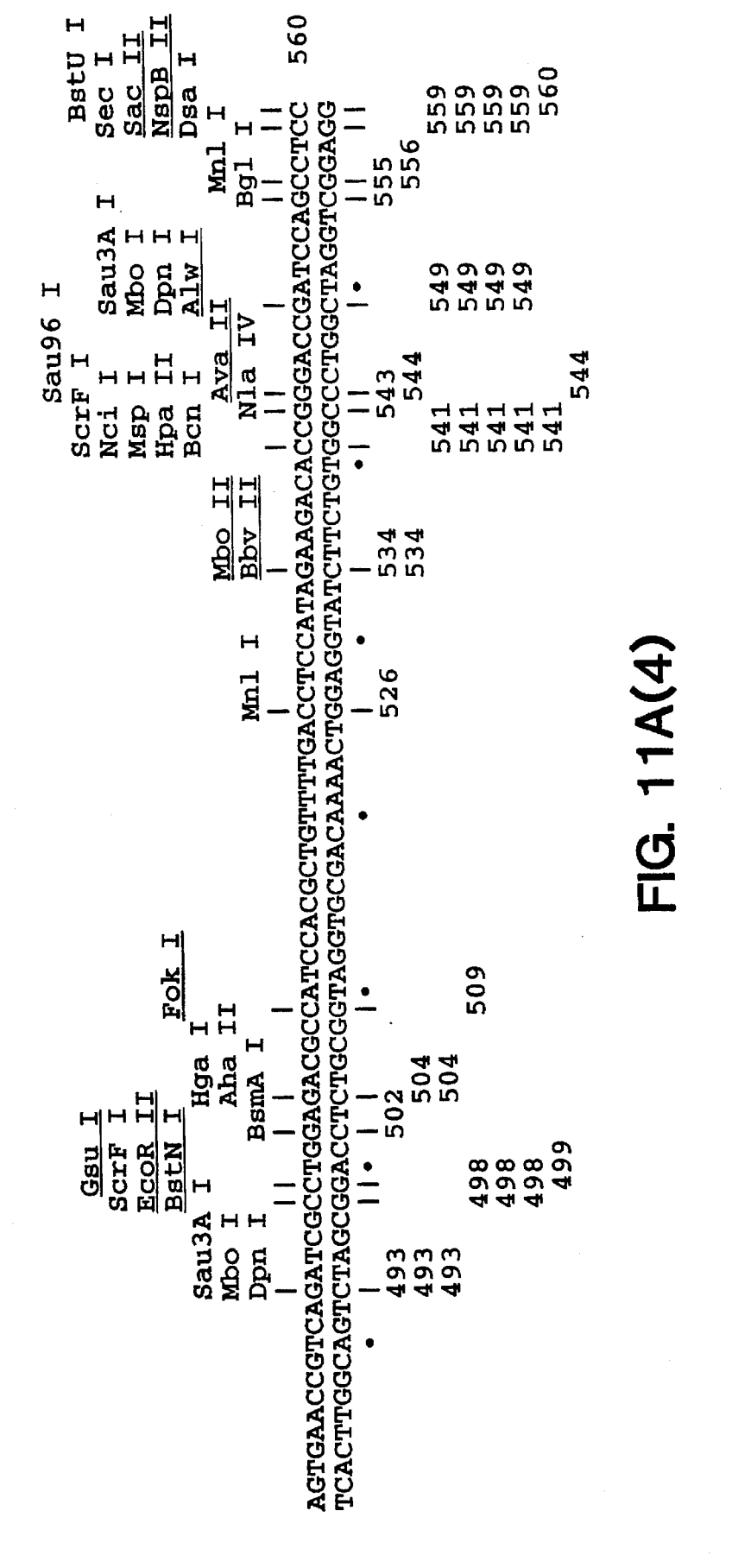

FIGS. 11A(1), 11A(2), 11A(3), 11A(4), 11A(5), 11A(6), 11A(7), 11A(8), and 11A(9) show a full restriction map of the immediate early enhancer and promoter region for HCMV (Towne).

Figure 11C:
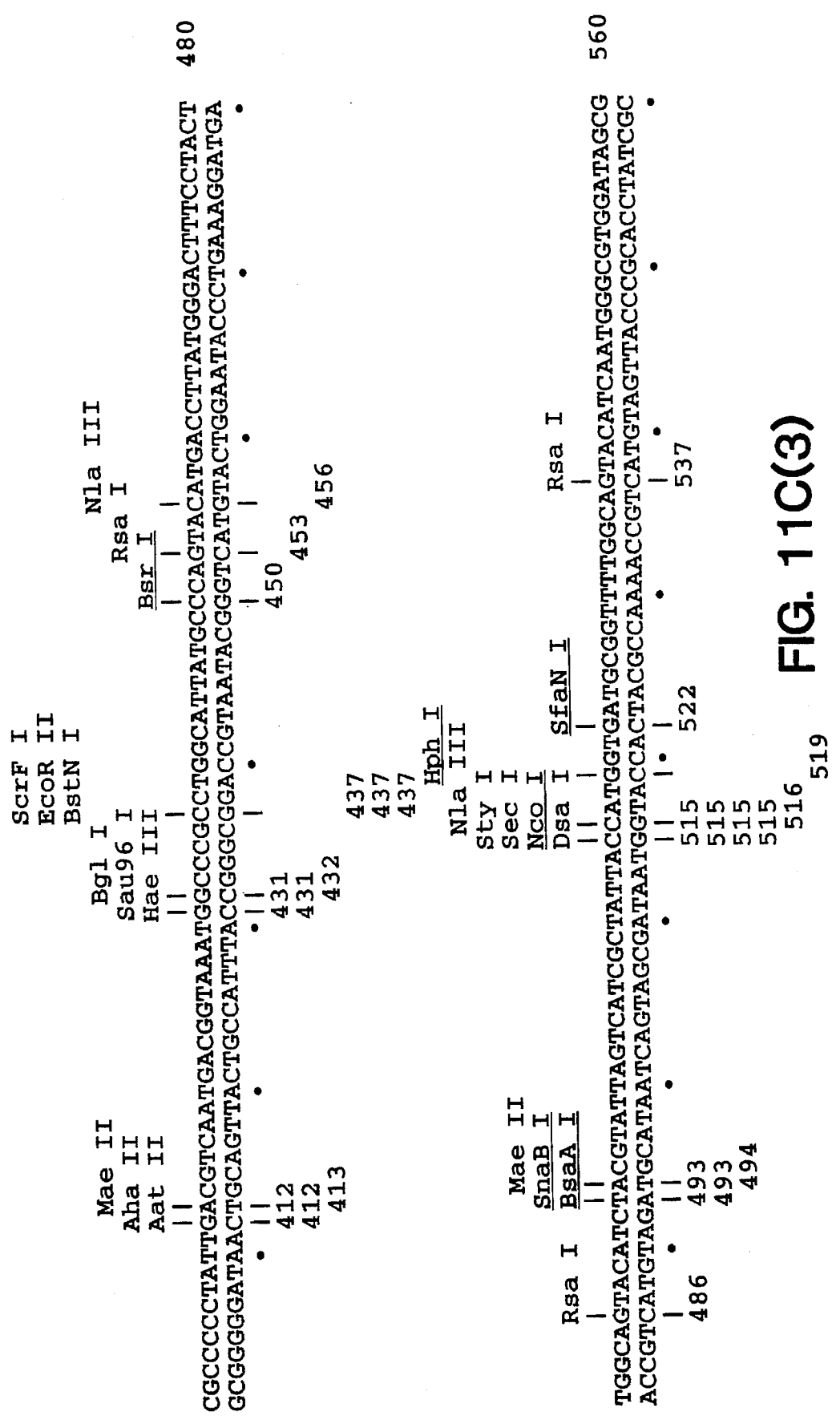
Figure 11C:
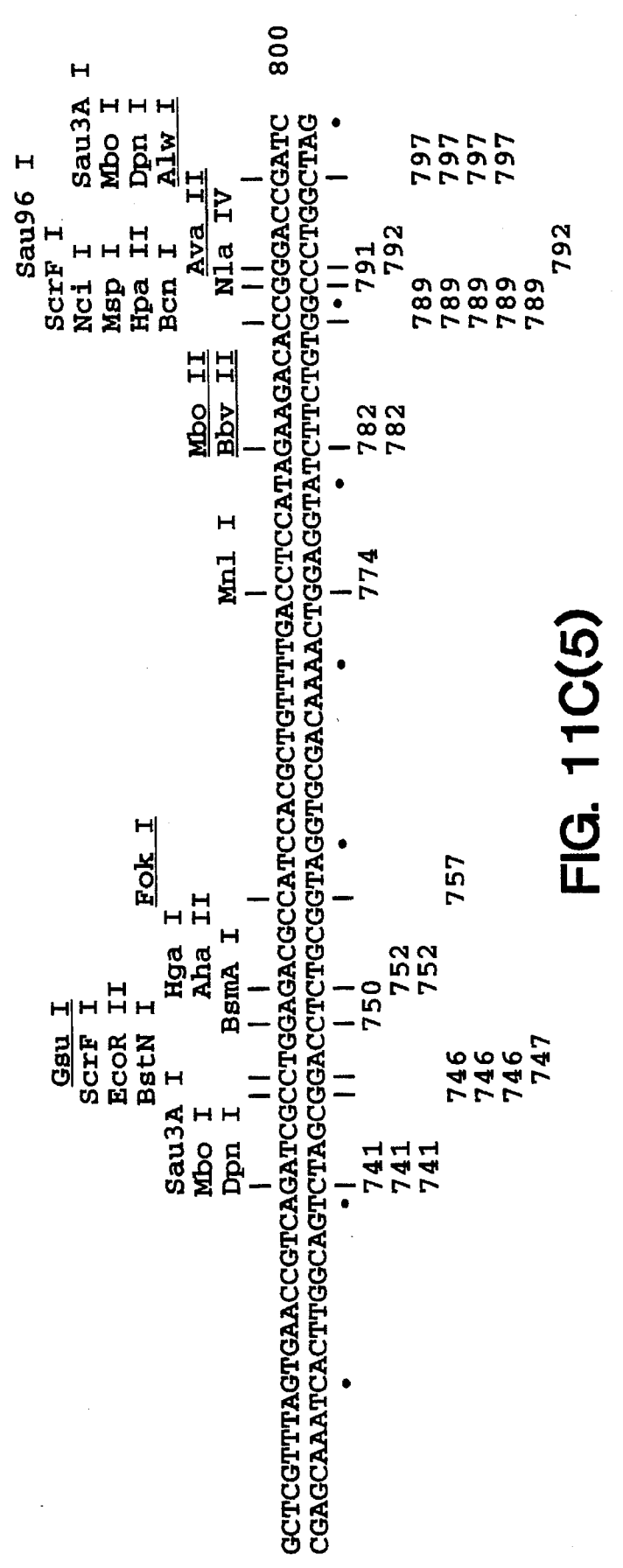

FIGS. 11C(1), 11C(2), 11C(3), 11C(4), 11C(5), 11C(6), and 11C(7) show a full restriction map of the immediate early enhancer and promoter region for HCMV (AD169).

FIGS. 11B(1), 11B(2), 11B(3), 11B(4), 11B(5), 11B(6) show a sequence comparison of the two HCMV promoters. The position of the NcoI site is indicated by an asterisk.

DESCRIPTION OF THE SPECIFIC EMBODIMENTS

In accordance with the subject invention, nucleic acid constructs together with methods of preparation and use are provided which allow for in vivo modulation of phenotype and/or genotype of cells in the respiratory tract of a mammalian host following delivery of a sufficient dose of a lipid carrier-nucleic acid aerosol to the host mammal to provide for transfection of host lung cells. The lipid carrier-nucleic acid aerosol is obtained by nebulization of a lipid carrier-nucleic acid sample mixture prepared in a biologically compatible fluid that minimizes aggregation of the lipid carrier-nucleic acid complexes. The methods and compositions can be used to produce a mammal comprising an exogenously supplied gene in lung tissue, particularly alveolar and airway passage cells.

Central to the present invention is the discovery that genes can be delivered to the lung via aerosol administration, and subsequently expressed in vivo. The instant invention takes advantage of the use of lipid carriers as a delivery mechanism. Lipid carriers are able to stably bind through charge interactions or entrap and retain nucleic acid and permit a system amenable to nebulization, whereby intact genes can be delivered to specific pulmonary tissues. Lipid carriers include but are not limited to liposome and micellas, as well as biodegradable cationic compounds comprising modified phosphoglycerides particularly alkylphosphoglycerides. Particular sites in the lung are targeted by varying the size of the aerosol particles administered, as discussed more fully below. Targeting agents, such as antibodies directed against surface antigens expressed on specific pulmonary cell types, can also be covalently conjugated to the lipid carrier surface so that nucleic acid can be delivered to specific cell types. Lipid carriers also allow for the delivery of relatively large mounts of nucleic acid, without a toxic effect, such that therapeutically effective mounts of the desired protein can be expressed in vivo. For a review of the use of liposomes as carriers for delivery of nucleic acids, see, Hug and Sleight, Biochim. Biophys. Acta. (1991) 1097: 1–17; Straubinger et ed., in Methods of Enzymology (1983), Vol. 101, pp. 512–527.

Lipid carriers, particularly liposomes, have been used effectively, particularly to introduce drugs, radiotherapeutic agents, enzymes, viruses, transcription factors and other cellular effectors into a variety of cultured cell lines and animals. In addition, successful clinical trials examining the effectiveness of liposome-mediated delivery of small drug molecules and peptides which act extracellularly have been reported. However, while the basic methodology for using liposome-mediated vectors is well developed and has been shown to be safe, the technique previously has not been developed for aerosolized delivery of nucleic acid to pulmonary tissue for in vivo gene therapy. By in vivo gene therapy is meant transcription and/or translation of exogenously supplied nucleic acid sequences to prevent, palliate and/or cure animal or human disease.

In addition to the discovery that transformation of lung cells can be obtained using aerosolized lipid carrier-nucleic acid complexes, several factors have been identified that can affect the relative ability of particular lipid carrier-nucleic acid complexes to provide transformation of lung cells following aerosolized delivery of a solution containing the lipid carrier-nucleic acid constructs and to achieve a high level of expression where that is the desired endpoint. The factors include (1) preparation of a solution that prior to or during nebulization will not form macroaggregates and wherein the nucleic acid is not sheared into fragments and (2) preparation both of lipid carriers and of expression constructs that provide for predictable transformation of host lung cells following aerosolization of the lipid carrier-nucleic acid complex and administration to the host animal. Other factors include the lipid carrier:nucleic acid ratio in the solution for nebulization and the diluent used to prepare the solution. These factors are discussed in detail below.

Aerosol delivery of nucleic acid-lipid carrier complexes provides a number of advantages over other modes of administration. For example, aerosol administration can serve to reduce host toxicity. Such an effect has been observed with the delivery of substances such as pentamidine and cytokines, which can be highly toxic when delivered systematically, but are well tolerated when aerosolized. Additionally, the results in rodents with aerosolized pentamidine accurately predicted results in human patients with AIDS treated with aerosolized pentamidine. See, for example, Debs et al., *Antimicrob. Agents Chemother.* (1987) 31: 37–41; Debs et al., *Amer. Rev. Respir. Dis.* (1987)135: 731–737; Debs et al., *J. Immunol.* (1988) 140: 3482–3488; Montgomery et al., *Lancet* (1987) 11: 480–483; Montgomery et al., *Chest* (1989) 95: 747–751; Leoung et al., *N. Eng. J. Med.* (1990) 323: 769–775. Additionally, rapid clearance of circulating liposomes by the liver and spleen reticuloendothelial system is avoided, thereby allowing the sustained presence of the administered substance at the site of interest, the lung. Serum induced inactivation of the therapeutic agent is also reduced. This method of transfection lung cells also avoids exposure of the host mammal's gonads, thus avoiding transfection of germ line cells.

Other advantages of the subject invention include ease of administration i.e., the host mammal simply inhales the aerosolized lipid carrier-nucleic acid solution into the intended tissue, the lung. Further, by varying the size of the nebulized particles some control may also be exercised over where in the lung the aerosol is delivered. Delivery may be extended over a long time period. Thus, there is a significant increase in the time period that target cells are exposed to the expression constructs. Distribution of the aerosol is even throughout areas of the lung accessible to the spray. These advantages are significant, particularly when compared to other routes of administration such as intratracheal delivery which is invasive, the expression constructs are delivered in a bolus which may disrupt the mucous barrier and additionally may result in pooling of the introduced fluid in areas of the lung at lower elevation. Further, damage from insertion of the intratracheal tube may alter the ability of cells coming into contact with the expression constructs to be transfected.

The type of vector used in the subject application may also be an advantage. For example, most gene therapy strategies have relied on transgene insertion into retroviral or DNA virus vectors. Potential disadvantages of retrovirus vectors, as compared to the use of lipid carriers, include the limited ability of retroviruses to mediate in vivo (as opposed to ex vivo) transgene expression; the inability of retrovirus vectors to transfect non-dividing cells; possible recombination events in replication-defective retrovirus vectors, resulting in infectious retroviruses; possible activation of oncogenes or inhibition of tumor suppressor genes due to the random insertion of the transgene into host cell genomic DNA; size limitations (less than 15 kb of DNA can be packaged in a retrovirus vector, whereas lipid carriers can be used to deliver sequences of DNA of $\geq 250$ kb to mammalian cells) and potential immunogenicity of the viral vectors leading to a host immune response against the vector. In addition, all ex vivo approaches require that the cells removed from the body be maintained in culture for a period of time. While in culture, cells may undergo deleterious or potentially dangerous phenotypic and/or genotypic changes. Adenovirus and other DNA viral vectors share several of the above potential limitations. Particularly for human use, but also for repeated veterinary use, biodegradable lipid carriers may be used which are metabolized by the host mammal to naturally occurring compounds that are non-toxic to the host and/or are readily excreted.

The nucleic acid constructs generally will be provided as expression cassettes which will include as operably linked components in the direction of transcription, a transcriptional initiation region, a nucleic acid sequence of interest and a transcriptional termination region wherein the transcriptional regulatory regions are functional in the mammalian host lung cell. An intron optionally may be included in the construct, preferably $\geq 100$ bp and placed 5' to the coding sequence. Generally it is preferred that the construct not become integrated into the host cell genome and it is introduced into the host as part of a non-integrating expression cassette. A coding sequence is "operably linked to" or "under the control of" transcriptional and/or translational regulatory regions in a cell when DNA polymerase will bind the promoter sequence and transcribe the coding sequence into mRNA, either a sense strand or an antisense strand. Thus, the nucleic acid sequence includes DNA sequences which encode polypeptides which are directly or indirectly responsible for a therapeutic effect, as well as genes coding for active nucleotide sequences such as antisense sequences and ribozymes.

The constructs for use in the invention include several forms, depending upon the intended use of the construct. Thus, the constructs include vectors, trancriptional cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

For the transcriptional initiation region, or promoter element, any region may be used with the proviso that it provides the desired level of transcription of the DNA sequence of interest. The transcriptional initiation region may be native to or homologous to the host cell, and/or to the DNA sequence to be transcribed, or foreign or heterologous to the host cell and/or the DNA sequence to be transcribed. By foreign to the host cell is intended that the transcriptional initiation region is not found in the host into which the construct comprising the transcriptional initiation region is to be inserted. By foreign to the DNA sequence is intended a transcriptional initiation region that is not normally associated with the DNA sequence of interest. Efficient promoter elements for transcription initiation include the SV40 (simian virus 40) early promoter, the RSV (Rous sarcoma virus) promoter, the Adenovirus major late promoter, and the human CMV (cytomegalovirus) immediate early 1 promoter.

Inducible promoters also find use with the subject invention where it is desired to control the timing of transcription. Examples of promoters include those obtained from β-inteferon gene, a heat shock gene, a metallothionein gene or those obtained from steroid hormone-responsive genes, including insect genes such as that encoding the ecdysone receptor. Such inducible promoters can be used to regulate transcription of the transgene by the use of external stimuli such as inteferon or glucocorticoids. Since the arrangement of eukaryotic promoter elements is highly flexible, combinations of constitutive and inducible elements also can be used. Tandem arrays of two or more inducible promoter elements may increase the level of induction above baseline levels of transcription which can be achieved when compared to the level of induction above baseline which can be achieved with a single inducible element.

Generally, the regulatory sequence comprises DNA up to about 1.5 Kb 5' of the transcriptional start of a gene, but can be significantly smaller. This regulatory sequence may be modified at the position corresponding to the first codon of the desired protein by site-directed mutagenesis Kunkel TA, 1985, Proc. Natl. Acad. Sci. (USA), 82: 488–492) or by introduction of a convenient linker oligonucleotide by ligation, if a suitable restriction site is found near the N-terminal codon. In the ideal embodiment, a coding sequence with a compatible restriction site may be ligated at the position corresponding to codon #1 of the gene. This substitution may be inserted in such a way that it completely replaces the native coding sequence and thus the substituted sequence is flanked at its 3' end by the gene terminator and polyadenylation signal.

Transcriptional enhancer elements optionally may be included in the expression cassette. By transcriptional enhancer elements is intended DNA sequences which are primary regulators of transcriptional activity and which can act to increase transcription from a promoter element, and generally do not have to be in the 5' orientation with respect to the promoter in order to enhance transcriptional activity. The combination of promoter and enhancer element(s) used in a particular expression cassette can be selected by one skilled in the art to maximize specific effects. Different enhancer elements can be used to produce a desired level of transgene expression in a wide variety of tissue and cell types. For example, the human CMV immediate early promoter-enhancer element can be used to produce high level transgene expression in many different tissues in vivo.

Examples of other enhancer elements which confer a high level of transcription on linked genes in a number of different cell types from many species include enhancers from SV40 and RSV-LTR. The SV40 and RSV-LTR are essentially constitutive. They may be combined with other enhancers which have specific effects, or the specific enhancers may be used alone. Thus, where specific control of transcription is desired, efficient enhancer elements that are active only in a tissue-, developmental-, or cell-specific fashion include immunoglobulin, interleukin-2 (IL-2) and β-globin enhancers are of interest. Tissue-, developmental-, or cell-specific enhancers can be used to obtain transgene expression in particular cell types, such as B-lymphocytes and T-lymphocytes, as well as myeloid, or erythroid progenitor cells. Alternatively, a tissue-specific promoter such as that derived from the human cystic fibrosis transmembrane conductance regulator (CFTR) gene can be fused to a very active, heterologous enhancer element, such as the SV40 enhancer, in order to confer both a high level of transcription and tissue-specific transgene transcription. In addition, the use of tissue-specific promoters, such as LCK, may allow targeting of transgene transcription to T lymphocytes. Tissue specific transcription of the transgene may be important, particularly in cases where the results of transcription of the transgene in tissues other than the target tissue would be deleterious.

Tandem repeats of two or more enhancer elements or combinations of enhancer elements may significantly increase transgene expression when compared to the use of a single copy of an enhancer element; hence enhancer elements find use in the expression cassette. The use of two different enhancer elements from the same or different sources flanking or within a single promoter can in some cases produce transgene expression in each tissue in which each individual enhancer acting alone would have an effect, thereby increasing the number of tissues in which transcription is obtained. In other cases, the presence of two different enhancer elements results in silencing of the enhancer effects. Evaluation of particular combinations of enhancer elements for a particular desired effect or tissue of expression is within the level of skill in the art. Although generally it is not necessary to include an intron in the expression cassette, an intron comprising a 5' splice site (donor site) and a 3' splice site (acceptor site) separated by a sufficient intervening sequence to produce high level, extended in vivo expression of a transgene administered iv or ip can optionally be included. Generally, an intervening sequence of about 100 bp produces the desired expression pattern and/or level, but the size of the sequence can be varied as needed to achieve a desired result. The optional intron placed 5' to the coding sequence results in high level extended in vivo expression of a transgene administered iv or ip but generally is not necessary to obtain expression. Optimally, the 5' intron specifically lacks cryptic splice sites which result in aberrantly spliced mRNA sequences. If used, the intron splice donor and splice acceptor sites, arranged from 5' to 3' respectively, are placed between the transcription initiation site and the translational start codon as diagrammed in (1), below.

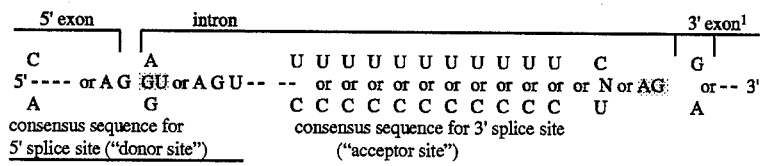

(1)

[1] The sequence given is that for the RNA chain; the nearly invariant GU and AG dinucleotides at either end of the intron are shaded.

Alternatively, the intervening sequence may be placed 3' to the translational stop codon and the transcriptional terminator or inside the coding region. The intron can be a hybrid intron with an intervening sequence or an intron taken from a genomic coding sequence. An intron 3' to the coding region, a 5' intron which is of less than 100 bp, or an intron which contains cryptic splice sites may under certain condition substantially reduce the level of transgene expression produced in vivo. However, unexpectedly, a high level of in vivo expression of a transgene can be achieved using a vector that lacks an intron. Such vectors therefore are of particular interest for in vivo transfection.

In some cases, it may be desirable to use constructs that produce long term transgene expression in vivo, either by integration into host cell genomic DNA at high levels or by persistence of the transgene in the nucleus of cells in vivo in stable, episomal form. Integration of the transgene into genomic DNA of host cells in vivo may be facilitated by administering the transgene in a linearized form (either the coding region alone, or the coding region together with 5' and 3' regulatory sequences, but without any plasmid sequences present). Additionally, in some instances, it may be desirable to delete or inactivate a mutant gene and replace it with a desired transgene. This may be achieved by using an expression cassette suitable for homologous recombination in vivo. Thus, for example, a linearized plasmid comprising an expression cassette may be used such as is described in European patent applications 88/201743.7 and PP89/202106.4. These applications disclose a plasmid for targeting of a specific gene. For the present application, a linear plasmid can be constructed wherein the replacement gene is flanked by 5' and 3' sequences which are sufficiently homologous with the 5' and 3' sequences of the defective gene to provide for homologous recombination. Where it desired to insert the replacement gene in the mutant gene (thereby inactivating it) a means for selection is included within the 5' and 3' flanking sequences of the plasmid.

The incidence of transgene integration into genomic DNA may be increased by incorporating a purified retroviral enzyme, such as the HIV-1 integrase enzyme, into the lipid carrier-DNA complex. Appropriate flanking sequences are placed at the 5' and 3' ends of the transgene DNA. These flanking sequences have been shown to mediate integration of the HIV-1 DNA into host cell genomic DNA in the presence of HIV-1 integrase. Alternatively, the duration of the transgene expression in vivo can be prolonged by the use of constructs that contain non-transforming sequences of a virus such as Epstein-Barr virus, sequences such as oriP and EBNA-1 which appear to be sufficient to allow heterologous DNA to be replicated as an episome in mammalian cells (Buhans et al., Cell (1986) 52: 955).

Downstream from and under control of the transcriptional initiation regulatory regions is a multiple cloning site for insertion of a nucleic acid sequence of interest which will provide for one or more alterations of host genotype and modulation of host phenotype. Conveniently, the multiple cloning site may be employed for a variety of nucleic acid sequences in an efficient manner. The nucleic acid sequence inserted in the cloning site may have any open reading frame encoding a polypeptide of interest, for example, an enzyme, with the proviso that where the coding sequence encodes a polypeptide of interest, it should lack cryptic splice sites which can bleak production of appropriate mRNA molecules and/or produce aberrantly spliced or abnormal mRNA molecules. The nucleic acid sequence may be DNA; it also may be a sequence complementary to a genomic sequence, where the genomic sequence may be one or more of an open reading frame, an intron, a non-coding leader sequence, or any other sequence where the complementary sequence will inhibit transcription, messenger RNA processing, for example splicing, or translation.

A number of nucleic acid sequences are of interest for use in vivo gene therapy of lung diseases or diseases of other tissues. When it is desired to have an extra-pulmonary effect, nucleic acid providing for secretory leader sequence is included in the expression cassette. Where the nucleic acid codes for a polypeptide, the polypeptide may be one which is active intracellularly, a transmembrane protein, or it may be a secreted protein. It may also code for a mutant protein for example are which is normally secreted but which has been altered to act intracellularly. The nucleic acid may also be a DNA sequences coding for mRNA (antisense or ribozyme sequences such as those to HIV-REV or BCR-ABL sequences) or for proteins such as transdominant negative mutants which specifically prevent the integration of HIV genes into the host cell genomic DNA, replication of HIV sequences, translation of HIV proteins, processing of HIV mRNA or virus packaging in human cells; the LDL (low density lipoprotein) receptor, which specifically lowers serum cholesterol, and which can reduce the risk of heart attack in individuals with elevated serum cholesterol levels, and proteins such as granulocyte macrophage colony stimulating factor (GM-CSF) which can stimulate the production of white blood cells from the bone marrow of immunocompromised patients and produce significant anti-tumor activity or cystic fibrosis transmembrance conductance regulator (CFTR) for treatment cystic fibrosis. These, or other beneficial (therapeutic) nucleic acid sequences can be expressed in appropriate cells in vivo using this invention.

Examples of beneficial therapeutic nucleic acid sequences are those encoding molecules have superoxide dismutase activity or catalase activity to protect the lung from oxidant injury; endothelial prostaglandin synthase to produce prostacyclin and prostaglandin E2; and antiprotease alpha-1 antitrypsin. Thus, this approach could dramatically improve the treatment of acquired immune deficiency syndrome (ADS), cystic fibrosis, cancer, heart dim, autoimmune diseases and a variety of life threatening infections. For the treatment AIDS, anti-TAT, REV TAR or other critical anti-HIV sequences may be used, particularly for expression of the appropriate coding sequences in T lymphocytes, macrophages and monocytes which can be achieved following iv administration of the appropriate coding sequences; expression of wild-type CFTR gene in the lungs of cystic fibrosis patients (see Collins, *Science* (1992) 256: 774–783) CFTR cDNA can be obtained from Dr. Collins at University of Michigan or Dr. Tsui at Toronto Sick Children's Hospital; expression of wild-type p53 in tumors of cancer patients with absent or aberrant expression of this gene, p53 is obtainable from Dr. Vogelstein at John Hopkins Univ; antisense sequences to over-expressed, transforming oncogenes, such as myc or ras in tumors; genes which block activity of activated T cell clones which attack myelin in multiple sclerosis or other targets in autoimmune diseases. A T-cell lymphocyte clone activated to recognize and attack myelin can be targeted by using an anti-sense sequence, ribozyme sequence or transgene coding for a transdominant negative mutant which specifically blocks surface expression on the T-cell of T-cell receptor components which mediate recognition and/or attack of myelin-sheathed cells.

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Adenylation residues, preferably more than 32 and up to 200 or more as necessary may be included in order to stabilize the mRNA. Alternatively, a terminator and polyadenylation signal from different gene/genes may be employed with similar results. Specific sequences which regulate post-transcriptional mRNA stability may optionally be included. For example, certain polyA sequences (Volloch et al. *Cell* (1981) 23: 509) and β-globin mRNA elements can increase mRNA stability, whereas certain AU-rich sequences in mRNA can decrease mRNA stability (Shyu et al., *Genes and Devel.* (1989) 3: 60). In addition, AU regions in 3' non-coding regions may be used to destabilize mRNA if a short half-life mRNA is desirable for the gene of interest.

The construct may additionally include sequences for selection, such as a neomycin resistance gene or a dihydrofolate reductase gene and/or signal sequences to regenerate recombinant proteins that are targeted to different cellular compartments or secreted when the wild type sequence is not. Any of a variety of signal sequences may be used which are well-known to those skilled in the art. These signal sequences may allow generation of new vaccine strategies or produce soluble antagonists directed against specific cell surface receptors such as transformed oncogenes. The sequences for selection may be on a separate plasmid and cotransfected with the plasmid carrying the therapeutic nucleic acid. Where a carrier is used, the selection plasmid may be complexed to a different carrier or to the same carrier as the therapeutic plasmid.

The recombinant coding-sequence flanked at its 5' end by the promoter and regulatory sequences and at its 3' end by a terminator and regulatory sequences may be introduced into a suitable cloning plasmid (e.g., pUC18, pSP72) for use in direct DNA uptake in host cells following introduction into the host Isolation of Genes and Construction of Lipid Carriers Nucleic acid sequences for use in the present invention, can be derived from known sources, for example by isolating the nucleic acid from cells containing the desired gene, using standard techniques. Similarly, the gene sequence can be generated synthetically, using standard modes of polynucleotide synthesis, well known in the art. See, e.g. Edge, M. D., *Nature* (1981). 292: 756; Nambair, et al., *Science* (1984) 223: 1299; Jay, Ernest, *J Biol Chem* (1984) 259: 6311. Generally, synthetic oligonucleotides are prepared by either the phosphotriester method as described by Edge et al., *Nature* (supra) and Duckworth et al., *Nucleic Acids Res* (1981)9: 1691, or the phosphoramidite method as described by Beaucage, S. L., and Caruthers, M. H., *Tet. Letts.* (1981) 22: 1859, and Matteucci, M. D., and Caruthers, M. H., *J. Am. Chem. Soc.* (1981) 103: 3185, and can be prepared using commercially available automated oligonucleotide synthesizers. The gene sequence can be designed with the appropriate codons for the particular amino acid sequence. In general, one will select preferred codons for expression in the intended host. The complete sequence is assembled from overlapping oligonucleotides prepared by standard methods and assembled into a complete coding sequence. See, e.g., Edge (1981) *Nature* 292: 756; Nambair et al., (1984) *Science* 223: 1299; Jay et al., (1984) *J. Biol. Chem.* 259: 6311.

A particularly convenient method for obtaining nucleic acid for use in the lipid carrier-nucleic acid preparations, is by recombinant means. Thus, the desired gene can be excised from a plasmid carrying the desired gene, using standard restriction enzymes and procedures. Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in *Methods in Enzymology* (1950) 65: 499–560.

Restriction cleaved fragments may be blunt ended by treating with the large fragment of *E. coli* DNA polymerase I (Klenow) in the presence of the four deoxynucleotide triphosphates (dNTPs) using standard techniques. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture can be extracted with e.g. phenol/chloroform, and ethanol precipitated. Treatment under appropriate conditions with S1 nuclease or BAL-31 results in hydrolysis of any single-stranded portion.

Once coding sequences for the desired proteins have been prepared or isolated, they can be cloned into any suitable vector or replicon. Numerous cloning vectors are known to those of skill in the art; the selection of an appropriate cloning vector is known to those of skill in the art, and the selection of an appropriate cloning vector is a matter of choice. Ligation to other sequences is performed using standard procedures, known in the art. For example, ligations can be accomplished in 30 mM Tris-Cl pH 7.8, 10 mM MgCl$_2$, 10 mM DTT, 50 µg/ml BSA, and either 1 mM ATP, 0.01–1.0 (Weiss) units T4 DNA ligase at 16° C. (for "sticky end" ligation) or 1 mM ATP, 0.5–1.0 (Weiss) units T4 DNA ligase at 20° C. (for "blunt end" ligation). Intermolecular "sticky end" ligations are usually performed at 30–100 µg/ml total DNA concentration (5–100 nM total end concentration).

The nucleic sequence is placed under the control of a promoter, ribosome binding site and, optionally, an operator (collectively referred to herein as "control" elements), so that the coding sequence is transcribed into RNA in the host tissue transformed by the lipid carrier-nucleic acid. The coding sequence may or may not contain a signal peptide or leader sequence. A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the transcription start codon (ATG) of a coding sequence and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase. Nucleic acid "control sequences" or "regulatory regions" refer collectively to promoter sequences, ribosome binding sites, polyadenylation signals, transcription termination sequences, upstream regulatory domains, enhancers, and the like, which collectively provide for the transcription and translation of a coding sequence in a host cell.

The choice of regulatory elements will depend on the host cell which is to be transformed and the type of nucleic acid preparation used. Thus, if the host cells' endogenous transcription and translation machinery will be used to express a polypeptide of interest, control elements functional in the particular host which provide for expression are used. Several promoters for use in mammalian cells are known in the art and include, but are not limited to, a SV40 (Simian Virus 40) early promoter, a RSV (Rous Sarcoma Virus) promoter, an Adenovirus major late promoter, and a human CMV (Cytomegalovirus) immediate early one promoter. Other promoters which may be used include those derived from mouse mammary tumor virus (MMTV, T7, T3, and the like). Particularly useful in the present invention are the RSV promoter and the CMV promoter, particularly the immediate early promoter from the AD169 strain of CMV.

In addition to the above sequences, it may be desirable to add to the nucleic acid construct regulatory sequences which allow for regulation of the expression of the polypeptide of interest sequences. Regulatory sequences are known to those of skill in the art, and examples include those which cause the expression of a gene to be turned on or off in response to a chemical or physical stimulus, including the presence of a regulatory compound. Such promoters can be used to regulate expression of the transgene by the use of external stimuli such as inteferon or glucocorticoids.

Other types of regulatory elements may also be present in the plasmid, for example, enhancer sequences. Such regulatory elements include those obtainable from β-inteferon, heat shock, metallothionein or steroid hormone responsive genes, including insect genes such as the ecdysone receptor gene. Since the arrangement of eukaryotic promoter elements is highly flexible, combinations of constitutive and inducible elements can be used. Tandem arrays of two or more inducible promoter elements may increase the level of induction above baseline levels of transcription which can be achieved with a single inducible element. By transcription enhancer elements are intended DNA sequences which are primary regulators of transcriptional activity which can act to increase transcription from a promoter element, and generally do not have to be in the 5' orientation with respect to the promoter in order to enhance transcriptional activity.

The combination of promoter and enhancer elements used in a particular nucleic acid construct can be selected by one skilled in the art to maximize specific effects; different enhancer elements can be used to produce a desired level of transgene expression. For example, a tissue specific promoter such as that derived from the human cystic fibrosis transmembrane conductance regulator (CFTR) gene can be used flanking a very active, heterologous enhancer element, such as the SV40 enhancer, in order to obtain both a high level of expression and expression of the transgene primarily in airway epithelial cells in the lung. Tandem repeats of two or more enhancer elements or combinations of enhancer elements may significantly increase transgene expression when compared to the use of a single copy of an enhancer element. The use of two different enhancer elements from the same or different sources, flanking or within a single promoter may be used. Evaluation of particular combinations of enhancer elements for a particular desired effect or expression level is within the knowledge of one skilled in the art. Promoter-enhancer elements which are least partially derived from CMV Townes and/or AD169 strains are of particular interest for providing a high level of expression of a transgene.

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Adenylation residues, preferably more than 32 and up to 200 or more if necessary may be included in order to stabilize the mRNA. Alternatively, terminator and polydenylation signals from a different gene/genes may be employed with similar results. Specific sequences which regulate post-transcriptional mRNA stability may optionally be included. For example, certain polyA sequences (Volloch et al., *Cell* (1981) 23: 509) and β-globin mRNA elements can increase mRNA stability, whereas certain AU-rich sequences in mRNA can decrease mRNA stability (Shyu et al., *Genes and Development* (1989) 3: 60). In addition, AU regions in 3' non-coding regions may be used to destabilize mRNA if a short half life mRNA is desirable. A 3'-intron should be avoided, particularly a SV40 3'-intron. If used, the 3'-intron should be greater than about 70 bp.

The nucleic acid construct may include sequences for selection, such as a neomycin resistance gene, dihydrofolate reductase gene, and/or signal sequences to regenerate recombinant proteins that are targeted to different cellular compartment or secreted when the wild type sequence is not. Any of a variety of signal sequences may be used which are well known to those skilled in the art. The signal sequences may allow generation of new vaccine strategies or produce soluble antagonists directly against specific cell surface receptors such as transformed oncogenes. The sequences for selection may be on a separate plasmid and cotransfected with the plasmid carrying the nucleic acid coding for the therapeutic polypeptide. The selection plasmid may be complexed to a different carrier or to the same carrier as the therapeutic plasmid.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

It may be desirable to produce mutants or analogs of the proteins of interest. Mutants or analogs may be prepared by the deletion of a portion of the sequence encoding the protein, by insertion of a sequence, and/or by substitution of one or more nucleotides within the sequence. The mutation can be one that affects secretion of a normally secreted protein, so as to eliminate or decrease systemic side effects of the protein, for example, tumor necrosis factor. Techniques for modifying nucleotide sequences, such as site-directed mutagenesis, are well known to those skilled in the art. See, e.g., Sambrook et al., infra; *DNA Cloning*, Vols. I and II, supra; *Nucleic Acid Hybridization*, infra.

If the gene sequence of the desired protein is not known, it can be obtained using the following general techniques. The desired protein can be isolated from, for example, tissue samples containing the same. This is generally accomplished by first preparing a crude extract which lacks tissue components and several extraneous proteins. The desired proteins can then be further purified i.e. by column chromatography, HPLC, immunoabsorbent techniques or other conventional methods well known in the art. Purification of the protein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook, et al., supra. First, a DNA library is prepared. The library can consist of a genomic DNA library from the species of choice. Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate.

In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consist of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionary close or distant species. The selection of the appropriate conditions is within the skill of the art. See, generally, *Nucleic Acid Hybrindization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein. The desired DNA sequence can then be cloned into a cloning vector and further used, as described below.

Preparation of Lipid Carriers

Liposomal preparations for use in the instant invention include cationic (positively charged), anionic (negatively charged) and neutral preparations. However, cationic lipid carriers are particularly preferred because a tight charge complex can be formed between the cationic lipid carrier and the polyanionic nucleic acid, resulting in a lipid carrier-nucleic acid complex which will withstand both the forces of nebulization and the environment within the lung airways and be capable of transfecting lung cells after the aerosolized DNA:lipid carrier complex has been deposited in the lung. Cationic liposomes have been shown to mediate intracellular delivery of plasmid DNA (Felgner, et al., *Proc. Natl. Acad. Sci. USA* (1987) 84: 7413–7416); mRNA (Malone, et al., *Proc. Natl. Acad. Sci. USA* (1989) 86: 6077–6081); and purified transcription factors (Debs, et al., *J. Biol. Chem.* (1990) 265: 10189–10192), in functional form.

Lipid carriers can be prepared from a variety of cationic lipids, including DOTAP, DOTMA, DDAB, L-PE, and the like. Lipid carriers containing a cationic lipid, such as {N(1-2-3-dioleyloxy) propyl}-N,N,N-triethylammonium} (DOTMA), dimethyl dioctadecyl ammonium bromide (DDAB), or 1,2-dioleoyloxy-3-(trimethylammonio) propane (DOTAP) or lysinylphosphatidylethanolamine (L-PE) and a second lipid, such as distearoylphosphatidylethanolamine (DSPE), dislcoylphosphatidylethanolamine (DOPE), or cholesterol (Chol), are of particular interest. DOTMA synthesis is described in Felgner, et al., *Proc. Nat. Acad. Sciences.* (USA) (1987) 84: 7413–7417. DOTAP synthesis is described in Stamatatos, et al., *Biochemistry* (1988) 27: 3917. DOTMA:DOPE liposomes carriers in the form of liposomes can be purchased from, for example, BRL. DOTAP:DOPE liposomes can be purchased from Boehringer Mannheim. Cholesterol and DDAB are commercially available from Sigma Corporation. DOPE is commercially available from Avanti Polar Lipids. DDAB:DOPE can be purchased from Promega. Biodegradable lipid carriers are of particular interest. Cationic lipids wherein the positive change is positioned very close to the lipid bilayer e.g. DDAB, rather than projecting out from the bilayer and therefore more exposed e.g. ethylphosphatidylethanolamine (E-PC), are also of interest.

Cationic lipid carrier:DNA complexes are internalized by cells by a classical receptor-mediated endocytosis using cell surface receptors which contain specific binding sites for, and are able to internalize, cationic molecules. Using agents such as cytokines, growth factors, other soluble proteins and certain drugs, it is thus possible to selectively up or down regulate these cation-binding receptors. The rate of up or down regulation of these receptors by the appropriate agent will allow selection of specific cells for enhanced or reduced levels of transfection in vivo. Thus, the use of specific cationic lipids can confer specific advantages for in vivo delivery. For example, iv injection of DOTAP-containing or ethylphosphatidylcholine (E-PC) lipid carriers can target transgene expression primarily to the lung and may offer increased advantages for aerosolized delivery. Furthermore, E-PC and DOTAP, as well as L-PE and CEBA are fully metabolized by cells, whereas DOTMA cannot be fully metabolized by cells. Therefore, DOTAP and L-PE, but not DOTMA, are suitable for repeated administration to mammalian hosts. Additionally, complexing the cationic lipid with a second lipid, primarily either cholesterol (0–50 mole percent, preferably 33–50 mole percent) or DOPE can maximize transgene expression in vivo. For example, mixing cholesterol instead of DOPE with DOTAP, DOTMA, or DDAB may substantially increase transgene expression in vivo.

Particular cells within the lung may be targeted by modifying the lipid carriers to direct them to particular types of cells using site-directing molecules. Thus antibodies or ligands for particular receptors may be employed, to target a cell associated with a particular surface protein. A particular ligand or antibody may be conjugated to the lipid carrier in accordance with conventional ways, either by conjugating the site-directing molecule to a lipid for incorporation into the lipid bilayer or by providing for a linking group on a lipid present in the bilayer for linking to a functionality of the site-directing compound. Such techniques are well known to those skilled in the art. For example, ligand-directed DNA-polycation complexes have been shown to transfect hepatocytes in the liver after iv injection. More precise intrapulmonary targeting may be achieved by a) altering aerosol particle size to preferentially direct the aerosol to alveoli or proximal versus distal airways or (b) to covalently couple monoclonal antibodies to the lipid carrier surface, thereby targeting lung cells expressing the corresponding cell surface antigen or using specific cationic lipids that have specific affinities for specific lung cell types.

Non-cationic liposomes, particularly pH sensitive liposomes, offer another potentially attractive approach to in vivo gene therapy. However, as compared to cationic liposomes, pH sensitive liposomes are less efficient in capturing DNA and delivering DNA intracellularly. Anionic and neutral liposomes are readily available, such as from Avanti Polar Lipids (Birmingham, Al.), or can be easily prepared using readily available materials. Such materials include phosphatidylcholine, cholesterol, phosphatidylethanolamine, dioleoylphosphatidylcholine (DOPC), dioleoylphoshaildylethanolamine (DOPE), among others. These materials can also be mixed with the DOTMA and DOTAP starting materials in appropriate ratios. Methods for making liposomes using these materials are well known in the art.

Unexpectedly, the lipid composition of the lipid carriers used for nebulization can dramatically affect the level of transgene expression produced in vivo. Thus, the liposomal lipid compositions generally have a composition of 50% molar ratio of cationic lipid to non-cationic lipid, but may range from 5% to 100%. The diameter of the lipid carriers should generally be within the range of 100 nm to 10 microns, preferably 100 nm to 500 nm. Other DNA sequences, such as adenovirus VA genes can be included in the lipid carrier-DNA complex formulation or be co-transfected with the gene of interest. The presence of genes coding for the adenovirus VA gene product may significantly enhance the translation of mRNA transcribed from the plasmid.

The lipid carriers can comprise multilamellar vesicles (MLVs), small unilamellar vesicles (SUVs), or large unilamellar vesicles (LUVs). MLV and LUV are prepared by vortexing rather than sonicating after addition of the aqueous material to the dry lipid film. If desired, the resulting lipid carriers can be extruded under high pressure through sized polycarbonate membranes to achieve more uniform size distributions. SUVs are prepared by extended sonication of MLVs to produce a homogeneous population of unilamellar lipid carriers. Commonly used methods for making lipid carriers include $Ca^{2+}$-EDTA chelation (Papahadjopoulos, et al., *Biochim. Biophys. Acta* (1975) 394: 483; Wilson, et al., *Cell* (1979) 17: 77); ether injection (Deamer, D. and Bangham, A., *Biochim. Biophys. Acta* (1976) 443: 629; Ostro, et al., *Biochem. Biophys. Res. Commun.* (1977) 76: 836; Fraley, et al., *Proc. Natl. Acad. Sci. USA* (1979) 76: 3348); detergent dialysis (Enoch, H. and Strittmatter, P., *Proc. Natl. Acad. Sci. USA* (1979) 76: 145) and reverse-phase evaporation (REV) (Fraley, et al., *J. Biol. Chem.* (1980) 255: 10431; Szoka, F. and Papahadjopoulos, D., *Proc. Natl. Acad. Sci. USA* (1978)75: 145; Schaefer-Ridder, et al., *Science* (1982) 215: 166).

The various lipid carrier-nucleic acid complexes wherein the lipid carrier is a liposome are prepared using methods well known in the art. See, e.g., Straubinger et al., in *Methods of Immunology* (1983), Vol. 101, pp. 512–527. By "lipid carrier-nucleic acid complex" is meant a nucleic acid sequence as described above, generally bound to the surface of a lipid carrier preparation. The lipid carrier preparation can also include other substances, such as enzymes necessary for integration, transcription and translation, cofactors, etc. Furthermore, the lipid carrier-nucleic acid complex can include targeting agents to deliver the complex to particular cell or tissue types.

To prepare the complexes, generally, the nucleic acid material is added to a suspension of preformed MLVs or SLVs only after the lipid carriers have been prepared and then vortexed. When using lipid carriers containing cationic lipids, the dried lipid film is resuspended in an appropriate mixing solution such as sterile water or an isotonic buffer solution such as 10 mm Tris/NaCl, or 5% dextrose in sterile water, sonicated, and then the preformed lipid carriers are mixed directly with the DNA. The lipid carrier and DNA form a very stable complex due to binding of the negatively charged DNA to the cationic lipid carriers. SUVs find use with small nucleic acid fragments as well as large regions of DNA (≧250 kb). In preparing the lipid carrier-nucleic acid complexes, care should be taken to exclude any compounds from the mixing solution which may promote the formation of aggregates of the lipid carrier-nucleic acid complexes. Large particles generally will not be aerosolized by the nebulizer and even if aerosolized would be too large to penetrate beyond the large airways. Aggregation of the lipid carrier-nucleic acid complex is prevented by controlling the ratio of DNA to lipid carrier, minimizing the overall concentration of DNA:lipid carrier complex in solution, usually less than 5 mg DNA/8 ml solution, and the avoiding chelating agents as EDTA, and significant amounts of salt which tend to promote macroaggregation. The preferred excipient is water, dextrose/water or another solution having low or no ionic strength. Further, the volume must be adjusted to the minimum for deposition in the lungs of the host mammal, but taking care not to make the solution too concentrated so that aggregates form.

The choice of lipid carriers and the concentration of lipid carrier-nucleic acid complexes thus involves a two step process. The first step is to identify lipid carriers and concentration of lipid carrier-nucleic acid complexes that do not aggregate when the components are combined or during the significant agitation of the mixture that occurs during the nebulization step. The second step is to identify among those that are identified as of interest at the first step (i.e. do not aggregate) those complexes that provide for a high level of transfection and expression of a gene of interest in target cells in the lung. The level of expression and the cell types in which expression of the recombinant gene is obtained may be determined at the mRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reported gene product present in the expression cassette.

As an example, a reporter gene CAT (which encodes chloramphenicol acetyl transferase) can be inserted in the expression cassette and used to evaluate each lipid carrier composition of interest. The DNA:lipid carrier complexes must be mixed in solutions which do not themselves induce aggregation of the DNA:lipid carrier complexes such as sterile water. The expression cassette (DNA) is mixed together with the lipid carriers to be tested in multiple different ratios, ranging as an example from 4:1 to 1:10 (micrograms DNA to nanomoles cationic lipid). The results provide information concerning which ratios result in aggregation of the DNA:lipid carrier complexes and are therefore not useful for use in vivo, and which complexes remain in a form suitable for aerosolization. The ratios which do not result in aggregation are tested in animal models to determine which of the DNA:lipid carrier ratios confer the highest level of transgene expression in vivo. For example, the optimal DNA:lipid carrier ratios for SUV for DOTMA/DOPE, E-PC:cholesterol, ethyldimystrylphosphatidylcholine and DDAB:Chol are 1:1 or 1:2.

Administration

The mammalian host may be any mammal having symptoms of a genetically-based disorder. Thus, the subject application finds use in domestic animals, feed stock, such as bovine, ovine, and porcine, as well as primates, particularly humans. In the method of the invention, transformation in vivo is obtained by introducing a non-integrating therapeutic plasmid into the mammalian host complexed to a lipid carrier, particularly a cationic lipid carrier more particularly, for human use or for repeated applications a biodegradable lipid carrier. For introduction into the mammalian host any physiologically acceptable medium may be employed for administering the DNA or lipid carriers, such as deionized water, 5% dextrose in water, and the like. Other components may be included in the formulation such as stabilizers, biocides, etc, providing that they meet the criteria outlined above, i.e. do not cause aggregation of the complexes. The various components listed above find extensive exemplification in the literature and need not be described in particular here.

The lipid carrier-nucleic acid complex is aerosolized by any appropriate method. For use with humans or other primates, the aerosol is generated by a medical nebulizer system which delivers the aerosol through a mouthpiece, facemask, etc. from which the mammalian host can draw the aerosol into the lungs. Various nebulizer are known in the art and can be used in the method of the present invention. See, for example, Boiarski, et al., U.S. Pat. No. 4,268,460; Lehmbeck, et al., U.S. Pat. No. 4,253,468; U.S. Pat. No. 4,046,146; Havstad, et al., U.S. Pat. No. 3,826,255; Knight, et al., U.S. Pat. No. 4,649,911; Bordoni, et al., U.S. Pat. No. 4,510,829. The selection of a nebulizer system depends on whether alveolar or airway delivery (i.e., trachea, primary, secondary or tertiary bronchi, etc.), is desired as well as verifying that the specific nebulizer system does not denature or inactivate the nucleic acid construct.

A convenient way to insure effective delivery of the nucleic acid to the alveoli is to select a nebulizer which produces sufficiently small particles for example, particles with a mean particle diameter of less than 5.0 microns (μm). More preferably the particles have a mean particle diameter of about 0.2 to about 4.0 μm, and most preferably the particles have mean diameter of about 0.2 to about 2 μm, since larger particles (≧5 μm) are generally deposited in the proximal airways or nasopharynx. As an alternative to selecting small mean particle diameters to achieve substantial distal airway and alveolar deposition, a very high dosage of the lipid carrier-nucleic acid preparation can be administered, with a larger mean particle diameter. A proviso to such an approach is that the particular lipid carrier-nucleic acid complex is chosen that is not too irritating at the required dosage and that there be a sufficient number of particles in the total particle population having a diameter in the 0.5 to about 5 μm range to allow for deposition in the alveoli. For proximal airway delivery, the mean particle size will be larger. For example, suitable mean particle diameters will generally be less than about 15 μm, more preferably from about 4 μm, and most preferably from about 5 μm to about 10 μm.

Examples of nebulizers useful for alveolar delivery include the Acorn 1 nebulizer, and the Respirgard II® Nebulizer System, both available commercially from Marquest Medical Products, Inc., Inglewood, Colo. Other commercially available nebulizers for use with the instant invention include the UltraVent® nebulizer available from Mallinckrodt, Inc. (Maryland Heights, Mo.); the Wright nebulizer (Wright, B. M., *Lancet* (1958) 3: 24–25); and the DeVilbiss nebulizer (Mercer et al., *Ant. Ind. Hyg. Assoc. J.* (1968) 29: 66–78; T. T. Mercer, *Chest* (1981) 80: 6 (Sup) 813–817). Nebulizers useful for airway delivery include those typically used in the treatment of asthma. Such nebulizers are also commercially available. One of skill in the art can determine the usefulness of a particular nebulizer by measuring the mean particle size generated thereby with for example, a 7 stage Mercer cascade impactor (Intox Products, Albuquerque, N.Mex.). Concentrations of the lipid carrier-nucleic acid complex from the impactor plates can be determined by eluting the complex therefrom and assessing the optical density at an appropriate wavelength and comparing the standard curves. Results are generally expressed as mass median aerodynamic diameter ± geometric standard deviation (Raabe, *J. Aerosol Sci.* (1971) 2: 289–303).

The amount of lipid carriers used will be an amount sufficient to provide for adequate transfection of cells after entry of the DNA or complexes into the lung and to provide for a therapeutic level of transcription and/or translation in transfected cells. A therapeutic level of transcription and/or translation is a sufficient amount to treat or palliate a disease of the host mammal following administration of the lipid carrier-nucleic acid complex to the host mammal's lung, particularly the alveoli or airway. Thus, an "effective amount" of the aerosolized lipid carrier-nucleic acid preparation, is a dose sufficient to effect treatment, that is, to cause alleviation or reduction of symptoms, to inhibit the worsening of symptoms, to prevent the onset of symptoms, and the like. The dosages of the present compositions which constitute an effective amount can be determined in view of this disclosure by one of ordinary skill in the art by running routine trials with appropriate controls. Comparison of the appropriate treatment groups to the controls will indicate whether a particular dosage is effective in preventing or reducing particular symptoms. Appropriate doses are discussed further below. While there is no direct method of measuring the actual amount of lipid carrier-nucleic acid complex delivered to the alveoli, bronchoalveolar lavage (BAL) can be used to indirectly measure alveolar concentrations of any expressed and secreted protein, usually 18–24 hrs after inhalation to allow clearance of the protein deposited in the larger airways and bronchi.

The total amount of nucleic acid delivered to a mammalian host will depend upon many factors, including the total amount aerosolized, the type of nebulizer, the particle size, breathing patterns of the mammalian host, severity of lung disease, concentration and mean diameter of the lipid carrier-nucleic acid complex in the aerosolized solution, and length of inhalation therapy. Thus, the amount of expressed protein measured in the alveoli may be substantially less than what would be expected to be expressed from the amount of nucleic acid present in the aerosol, since a large portion of the complex may be exhaled by the subject or trapped on the interior surfaces of the nebulizer apparatus. For example, approximately one third of the lipid carrier-nucleic acid dose that is placed into the nebulizer remains in the nebulizer and associated tubing after inhalation is completed. This is true regardless of the dose size, duration of inhalation, and type of nebulizer used. Moreover, resuspension of the residue and readministration does not significantly increase the dose delivered to the subject; about one third remains in the nebulizer. Furthermore, even with minimization of airway deposition, a portion of the dose is still deposited in the airways. Additionally, efficiency of expression of the encoded protein will vary widely with the expression system used.

Despite the interacting factors described above, one of ordinary skill in the art will be able readily to design effective protocols, particularly if the particle size of the aerosolisoptimized.Basedonestimatesofnebulizerefficiency, an effective dose delivered usually lies in the range of about 1 mg/treatment to about 500 mg/treatment, although more or less may be found to be effective depending on the subject and desired result. It is generally desirable to administer higher doses when treating more severe conditions. Generally, the nucleic acid is not integrated into the host cell genome, thus if necessary, the treatment can be repeated on an ad hoe basis depending upon the results achieved. If the treatment is repeated, the mammalian host is monitored to ensure that there is no adverse immune response to the treatment. The frequency of treatments depends upon a number of factors, such as the amount of lipid carrier-nucleic acid complex administered per dose, as well as the health and history of the subject. As used herein, with reference to dosages, "lipid carrier-nucleic acid aerosol" refers to the amount of lipid carrier-nucleic acid complex that is placed in the nebulizer and subjected to aerosolization. The "amount nebulized" or "amount aerosolized" of the complex means the amount that actually leaves the apparatus as an aerosol, i.e., the amount placed into the apparatus less the amount retained in the reservoir and on the inner surfaces of the apparatus at the conclusion of a treatment session.

In particular treatment regimens, for example, in the treatment of cancer, it may be necessary to administer sequential doses at intervals ranging from every 8 to 12 hours to once a month. The frequency of treatment can be monitored by evaluating whether there has been until significant melioration or complete disappearance of the cancer with a particular treatment regimen. Treatment may have to be modified if dose-limiting host toxicity develops. Similar administration protocols also may be developed in for example, patients where all macroscopic evidence of tumor has been removed, in order to prevent tumor recurrence due to persistence of undetected microscopic disease.

To treat pulmonary infections such as bronchitis and pneumonia, it will usually be necessary to administer at least one dose per day over a period of about 4 to about 21 consecutive days or longer. The treatment is usually carried out on consecutive days because new areas of the lungs open up to penetration and deposition of the nucleic acid with increasing resolution of the infection. The success of the treatment can be monitored and the administration regimen altered by assessing conventional clinical criteria; e.g., clearing of radiographic infiltrate, improved arterial $PO_2$ (e.g., >70 mmHg), reduction in dyspnea, respiratory rate and/or fever. For the treatment of genetic disorders, such as cystic fibrosis, the lipid carrier-nucleic acid complex will be administered at regular intervals, from once a week to once every one to several months, in order to provide wild-type CFTR protein in critical host airway cells, since these cells continue to turn over. It may also be possible to stably transfect the CFTR gene into appropriate lung stem cells, which would then provide a continuous source of normal airway cells without requiring lifelong treatment. Potential therapeutic effects of the gene product can be measured, by determining the effects of gene expression on survival of transgenic host mammals in which the transgene is expressed. Production of significant amounts of a transgene product will substantially prolong the survival of the affiliated host.

Where expression of the polypeptide/protein or even the mRNA itself confers a changed biochemical phenotype upon the host, the presence of a new phenotype or absence of an old phenotype may be evaluated; for example, as a result of transformation of the host cells, there may be enhanced production of pre-existing desirable products formerly produced in insufficient quantities or there may be reduction or even suppression of an undesirable gene product using antisense, ribozyme or co-suppression technologies; in the case of reduction or suppression, a reduction or elimination of the gene product may be determined.

The potential toxicity of the treatment may be evaluated by behavioral manifestations, and where appropriate, by analysis of biopsy specimens. Thus, behavioral activity which evidences distress, such as changes in activity level, changes in eating and drinking patterns and the like, can be monitored, as well as evidence of necrosis, edema or inflammation in biopsy specimens.

The subject compositions can be provided for use in one or more procedures. Kits will usually include the DNA either as naked DNA or complexed to lipid carriers. Additionally, lipid carriers may be provided in a separate container for complexing with the provided DNA. The DNA or the lipid carrier/DNA complexes may be present as concentrates which may be further diluted prior to use or they may be provided at the concentration of use, where the vials may include one or more dosages. Conveniently, single dosages may be provided in sterilized containers suitable for use with a nebulizer, so that the physician or veterinarian may employ the containers directly with a nebulizer, where the containers will have the desired amount and concentration of agents. Thus, the kit may have a plurality of containers containing the DNA or the DNA/lipid carrier complexes in appropriate proportional amounts, and optionally, appropriate diluent and mixing solutions. When the containers contain the formulation for direct use, usually there will be no need for other reagents for use with the method.

Uses

Uses of the subject invention include but are not limited to the following. The present invention is particularly useful for the delivery of substances directly into the lung for the prevention and/or treatment of pulmonary disorders such as lung cancer, emphysema, asthma, lung infections such as chronic bronchitis and pneumonia, degenerative diseases of the lung, as well as genetic disorders such as cystic fibrosis and α-1 antitrypsin deficiency.

For the treatment of lung tumors, genes encoding toxic peptides (for example, therapeutic agents such as ricin, diphtheria toxin and cobra venom factor), wild-type tumor suppressor genes (such as p53, genes coding for mRNA sequences which are antisense to transforming oncogenes, or other antineoplastic peptides, such as tumor necrosis factor (TNF) and other cytokines, or transdominant negative mutants of transforming oncogenes), can be inserted into the nucleic acid construct and using the above described methods, complexed to a lipid carrier and delivered for expression at or near the tumor site. Some tumors such as colon minors can be specifically targeted by incorporating targeting agents, such as antibodies directed against tumor cell surface antigens, onto the lipid carrier. See, e.g., Laserman, et al., *Nature* (1980) 288: 602–604; Huang, et al., *Biochemistry* (1981) 20: 4299–4238, for methods of incorporating antibodies onto liposomal surfaces. Similarly, genes coding for peptides known to display antiviral and/or antibacterial activity, or stimulate the host' immune system, can also be administered to the lung in order to treat pulmonary infections. Thus, the genes encoding many of the various cytokines (or functional fragments thereof), such as the interleukins, intefferons, and colony stimulating factors, will find use with the instant invention. The gene sequences for a number of these substances are known. Inteferon-γ produces significant anti-pneumocystis carinii pneumonial (PCP) activity in immunodeficient mice with PCP following aerosol delivery of the peptide. Beck et al., *Infect. and Immun.* (1991) 59: 3859–3862.

Genes encoding antioxidants will also find use for the treatment or prevention of lung damage due to degenerative lung disorders caused by smoking and other environmental agents. For example, genes encoding superoxide dismutase (SOD) or catalase, as well as α-1 antitrypsin, will be particularly useful for this purpose. These gene sequences are known. See, e.g., Long et al., *Biochem,* (1984) 23: 4828–4837 for the α-1 antitrypsin gene sequence. For the treatment of genetic disorders, such as cystic fibrosis and emphysema, functional genes, corresponding to genes known to be deficient in the particular disorder, can be administered to the subject. For example, it is known that individuals lacking sufficient levels of α-1 antitrypsin are prone to emphysema and other pulmonary disorders. Thus, this gene can be administered prophylactically, as well as in response to clinical manifestations of the disease, for both the prevention and/or treatment of this disorder. Similarly, the gene involved in cystic fibrosis has been identified. Goodfellow, P., *Nature* (1989) 341: 102–103; Rommens, et al., *Science* (1989) 245: 1059–1054; Beardsley, et al., *Sci. Am.* (1989)261: 28–30. Thus, this gene, or fragments which encode a biologically active expression product, can be delivered to a mammalian host suffering from this disorder.

The invention also finds use for the delivery of substances into the systematic circulation via the lung. For example, as explained above, a number of substances, such as cytokines, are toxic when administered using conventional methods of delivery. See, e.g., Debs et al., *J. Immunol* (1988) 140: 3482–3488. The invention allows the delivery of these substances for example, to treat cancer, as well as bacterial and vital infections, systemically. This approach already has shown promise for the treatment of extra-pulmonary cancer in humans.

The instant methods also find use in antisense therapy, for the delivery of oligonucleotides able to hybridize to specific complementary sequences, thereby inhibiting the transcription and/or translation of these sequences. Thus, DNA or RNA coding for proteins necessary for the progress of a particular disease, can be targeted, thereby disrupting the disease process. For a review of antisense therapy and oligonucleotides useful in the same, see, Uhlmann, E. and Peyman, A., *Chem. Rev.* (1990) 90: 543–584.

The following examples are provided for illustrative purposes only and are not intended to limit the scope of the present invention.

EXAMPLES

The practice of the present invention employs unless otherwise indicated, conventional techniques of cell culture, molecular biology, microbiology, recombinant DNA, and immunology, which are within the skill of the art. Such techniques are explained fully in the literature. See, Sambrook, et al., *Molecular Cloning: A Laboratory Manual*, Second Edition (1989) Vols. 1–3; DNA Cloning (1985) Vols. I and II, D. N. Glover (ed.); *Nucleic Acid Hybridization* (1984), B. D. Hames, et al., (eds.); Perbal, B., *A Practical Guide to Molecular Cloning* (1984); *Methods in Enzymology* (the series), Academic Press, Inc.; Vectors: *A Survey of Molecular Cloning Vectors and Their Uses* (1987), R. L. Rodriguez, et al., (eds.), Butterworths; and Miller, J. H., et al., *Experiments in Molecular Genetics* (1972) Cold Spring Harbor Laboratory.

Up to 48 mice may be placed in the chamber at one time. The amount of the total amount of DNA-lipid carrier complex placed in the nebulizer that is delivered to the lungs of each mouse is approximately 0.02%.

Example I

Expression of Chloramphenicol Aacetyltransferase (CAT) Gene, in Rodent Lungs Following Aerosolized Delivery of Lipid Carrier-Nucleic Acid Complexes.

The lipid carriers used were plasmid pRSV-CAT, as described by Gorman, et al., *Proc. Natl. Acad. Sci. USA* (1982) 79: 6777–6781; and Juang, and Gorman, *Mol. Cell. Biol.* (1990) 10: 1805–1810; a plasmid containing the CAT gene driven by the RSV long terminal repeat; and plasmid pRSV-β-gal, as described by Hazinski et al., *Am. J. Respir. Cell Mol. Biol.* (1991) 4: 206–209.

Figure 1:
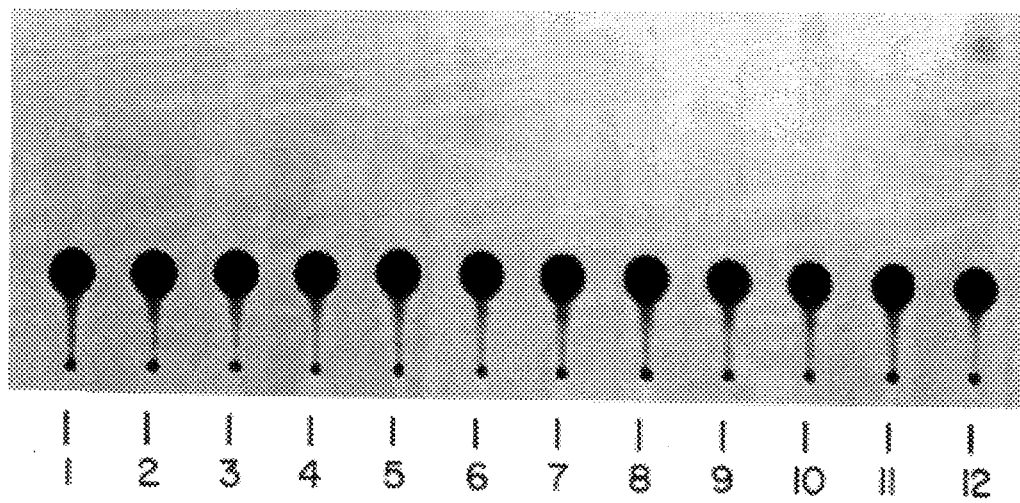

The pRSV-CAT plasmid was complexed to liposomes and administered to 25 gram female BALB/c mice as follows. Two mg of pRSV-CAT was mixed with 4 μmoles of DOTMA (GIBCO BRL, Grand Island, N.Y.)/cholesterol (2:1) small unilamellar liposomes in phosphate buffered saline and then nebulized in an Acorn I nebulizer (Marquest Medical Products, Inc., Inglewood, Colo.) to groups of rots or mice in an Intox nose-only exposure chamber (Intox Products, Albuquerque, N.Mex.). The same procedure was followed with 0.5 mg pRSV-CAT mixed with 1.0 μmol DOTMA-cholesterol (2:1), as well as 2.0 mg pRSV-CAT alone. Two to five days later, animals were sacrificed and lungs collected. Lungs were also collected from untreated controls. The lungs were homogenized and cells disrupted with three freeze-thaw cycles. CAT activity in aliquots from the lung extracts was measured using a standard assay as described by Wolff, et al., *Science* (1990) 247: 1465–1468. As can be seen in FIG. 1, animals administered 2.0 mg RSV-CAT with 4.0 μmol DOTMA/cholesterol (2:1) expressed the CAT protein in the lungs while the control animals as well as animals receiving aerosolized RSV-CAT DNA alone, or lower doses of RSV-CAT:DOTMA:chol complexes did not. A similar procedure was followed with respect to pRSV-β-gal, with the exception that 50 mg of pRSV-β-gal was mixed with 50 μmoles of DOTMA/cholesterol (2:1). The presence of β-gal activity was determined using a standard histochemical staining procedure. β-gal activity was present in the airway epithelial cells of exposed rats.

Also tested was a plasmid containing the CAT gene driven by the CMV promoter. This plasmid was made as described in Huang, M. T. F. and Gorman, C. M. *Nuc. Acids Res.* (1990) 8: 937–947, with the exception that a CMV promoter and a hybrid intron sequence were used rather than the SV40 promoter in the plasmid pML.I.CAT, described therein. Briefly, the CAT lipid carrier was constructed by first making a pML-based plasmid containing the CMV promoter immediately followed by a portion of the 5'-untranslated leader from the adenovirus-major late (AML) region. This region contained all but the first 13 nucleotides of the first exon of the tripartite leader plus a portion of an intervening sequence (IVS) from the AML region. A synthetic oligonucleotide was inserted which merged with the adenovirus intron to provide a functional splice acceptor sequence derived from an IgG variable region. Bothwell, et al., *Cell* (1981) 24: 625–637. This plasmid was then cut at two restriction sites bordering the intron (ClaI and PstI) to remove a 292 bp fragment. A matching synthetic oligonucleotide linker was inserted. The plasmid was termed pCIS-CAT.

Figure 2:
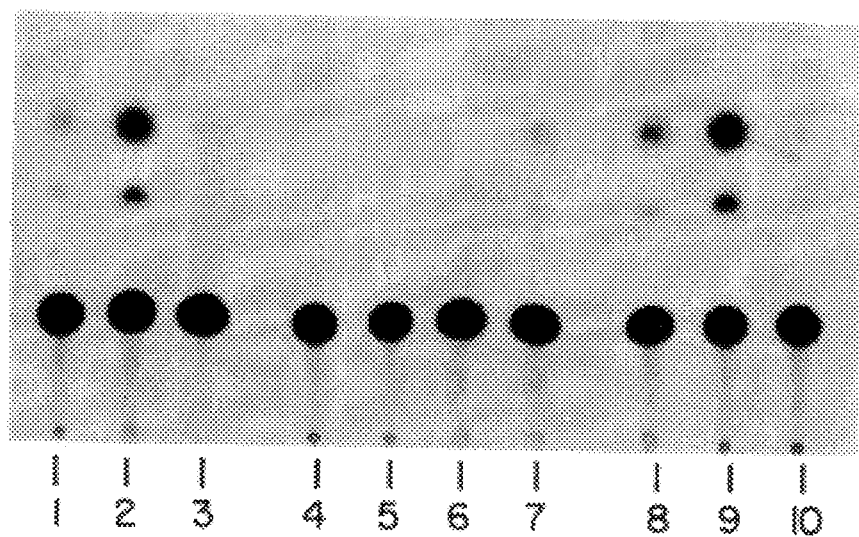
Figure 3A:
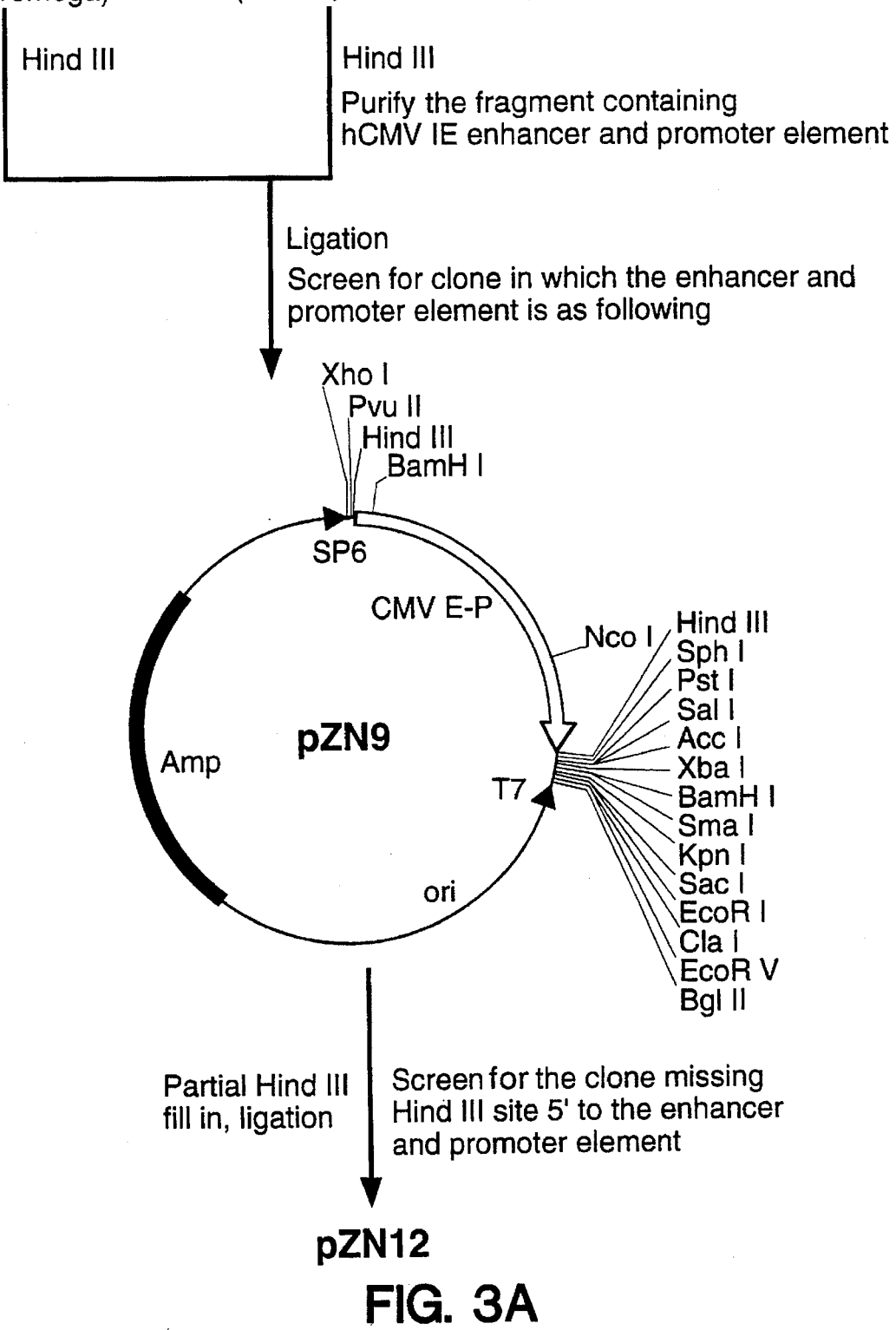
Figure 3B:
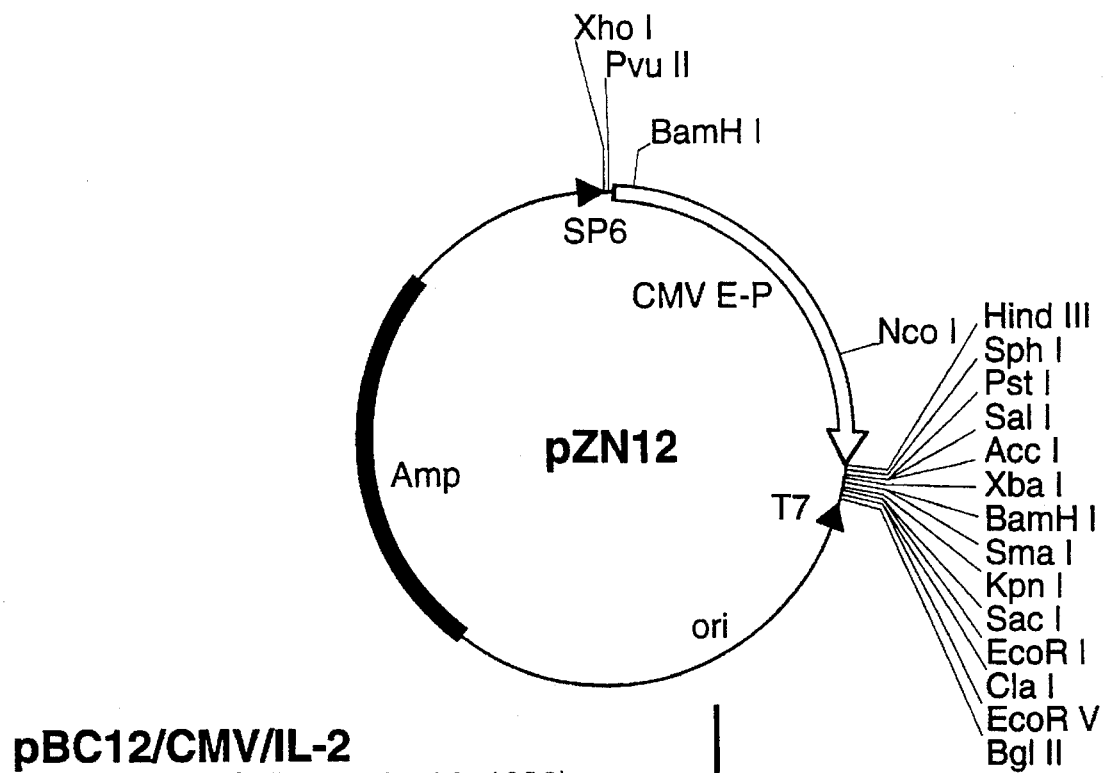
Figure 3B:
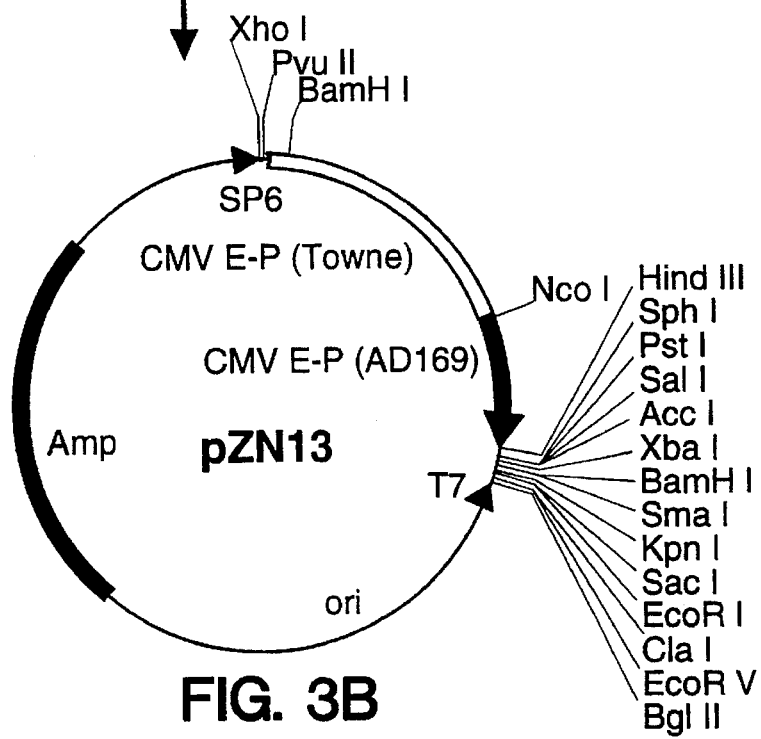
Figure 3C:
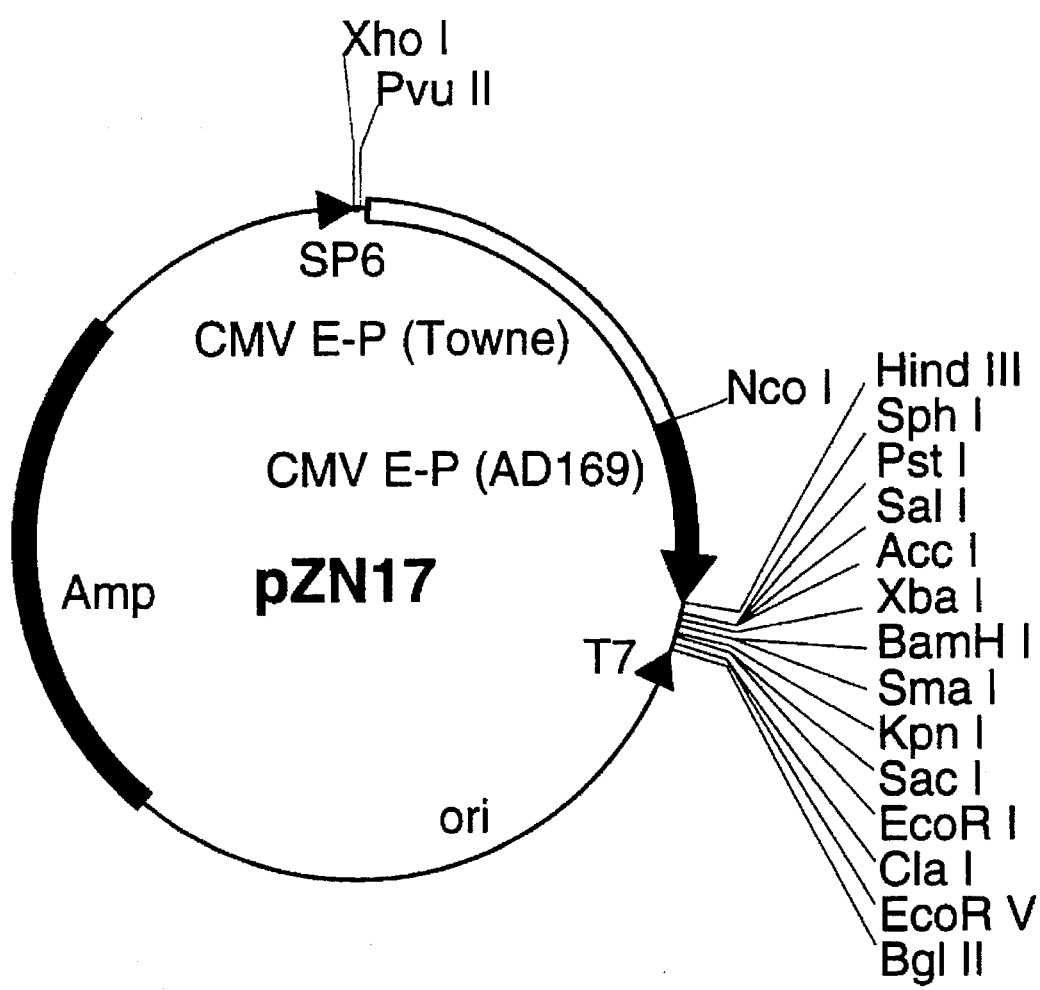

To test for expression of the CAT gene using pCIS-CAT, 12 mg pCIS-CAT was mixed with 24 μmoles of DOTMA/DOPE (1:1). Female ICR mice were placed in three different aerosol receiving chambers. All mice received the same amount of the CAT expression plasmid complexed to liposomes, as described above. Animals 1–3 were exposed to the aerosol in an Intox designed aerosol chamber. Animals 4–7 were exposed to the aerosol in a modified rat cage containing dividers for individual mice. Animals 8–10 were placed in a smaller, similarly modified mouse cage after being put in the restrainers used in the Intox chamber. 48 hours following aerosolization, the animals were sacrificed and whole lungs assayed for CAT expression using the chromatographic CAT assay. As can be seen in FIG. 2, a single aerosol dose of a CAT gene-expression plasmid complexed to cationic liposomes can produce high-level transgene expression in the lungs of mice. Significant levels of transgene expression are present in the lungs of all 7 mice (numbers 1–3 and 8–10) which were exposed to the aerosol mist in Intox nose-only exposure robes which were constructed to maximize the amount of aerosol that the mice inhaled. The amount of variation seen here is comparable to that seen in other aerosol experiments and may have several explanations, including variations in exposure to the aerosol mist, individual variations in efficiency of nasal filtration, etc.

Example II

Aerosol Administration of CMV-CAT Cationic Lipid Carrier Complexes Produces High Level, Lung Specific Expression of the CAT Gene.

Animals.

Two month old, female, ICR mice were used in all experiments.

Preparation of plasmid DNA.

The chloramphenicol acetyltransferase (CAT) gene was used as a reporter to measure transgene expression levels (Gorman et at., *Proc. Nat'Acad Sci* (USA) (1982) 79: 6777–6781). The plasmid used contains the CAT gene fused to the human cytomegalovirus (CMV) immediate early promoter-enhancer element (pCIS-CAT). The plasmid was purified using alkaline lysis and ammonium acetate precipitation (Sambrook et al. (1989) *supra*), and the nucleic acid concentration measured by UV absorption at 260 nm. The CAT gene is not present in eukaryotic cells. Its product is an enzyme which catalyzes the transfer of acetyl groups from acetylCoA to the substrate chloramphenicol.

Preparation of cationic liposomes.

Liposomes were prepared as small unilamellar vesicles (approximately 100 nm in diameter) containing the cationic lipid DOTMA as DOTMA:DOPE (1:1 mole ratio). DOTMA is (N[1-2,3-dioleyloxy)propyl]-N,N,N-triethylammonium (Syntex Corporation), and DOPE is the neutral lipid dioleoylphosphatidylethanolamine (Avanti Polar Lipids). Stock solutions of the lipids were dissolved in chloroform and stored under argon at −20° C. Lipids were mixed in a round-bottomed flask and evaporated to dryness on a rotary evaporator under reduced pressure. Double-distilled water was added to produce final lipid concentrations of 10 mM each, and the resulting mix was sonicated for approximately 20 minutes in a bath sonicator (Laboratory Supplies, Hicksville, N.Y.). The liposomes were stored under argon at 4° C. until use.

Aerosol delivery of plasmid/liposome complexes to mice.

Twelve mg of plasmid complexed to 24 μmols of DOTMA:DOPE (1:1 mole ratio) liposomes was aerosolized and administered to mice over two different aerosol periods on the same day. In order to prevent aggregation and precipitation of the oppositely charged components, the plasmid and the liposomes were diluted separately in sterile water prior to mixing. Six mg of plasmid DNA and 12 μmols of DOTMA:DOPE (1:1 mole ratio) liposomes were each diluted to 8 ml with water and mixed. Light ml was then placed into each of two Acorn I nebulizers (Marquest, Englewood, Colo.), the animals placed into an Intox small animal exposure chamber (Albuquerque, N.Mex.), and an air flow rate of 1 L min$^{-4}$ used to generate the aerosol. Approximately 90 minutes were required to aerosolize 16 ml. The animals were removed from the chamber for 1–2 hours and then the above procedure was repeated with a second 16 ml dose.

Radiometric Assay of CAT Activity.

Organs were dissected from animals sacrificed in a $CO_2$ chamber at periods from 1 to 21 days following aerosolization, washed in cold phosphate buffered saline (PBS), and homogenized using a hand-held tissue homogenizer in 250 mM Tris-HCl, pH. 7.5, containing 5 mM EDTA for lungs and spleen and 250 mM Tris-HCl, pH 7.5, containing 5 mM EDTA plus the protease inhibitors aporotitin, E-64, and leupeptic (Boehringer Mannheim) for liver, heart and kidneys. The inhibitors prevent degradation of acetylated chloramphenicol species generated during the assay, thereby allowing optimal detection of CAT expression.

Following homogenization of the tissue, cells were lysed by three freeze/thaw cycles, the lysate heated (65° C. for 10 minutes), and centrifugated (16,000×g, 2 minutes). The protein concentrations of the extracts were measured using a Coomassie blue-based assay (Bio-Rad). Protein concentrations were normalized and a volume of extract added to 10 μl of 100 mM acetylCoA (Sigma), 0.3 μCi of [$^{14}C$]-labelled chloramphenicol (Amersham), and distilled water to a final volume of 180 μl, and allowed to react at 37° C. for 8–10 hours (Gorman et al. (1982) supra). Following the reaction, the acetylated and unacetylated chloramphenicol species were extracted with cold ethyl acetate, spotted on silica TLC plates, and developed with a chloroform:methanol (95:5v/v) solvent. The TLC plates were exposed to photographic film (Kodak X-OMAT) for one to three days, then evaluated by visual inspection.

Preparation of Genomic DNA and Southern Hybridization.

Immediately following aerosolization, mice were sacrificed and their lungs removed. Genomic DNA was isolated and analyzed by Southern hybridization (Sambrook et al. (1989) supra) using a Hybond N+ membrane (Amersham). A CAT probe was prepared from a 1.6 kb fragment of the CAT gene labelled with α-[$^{32}$]dATP by random priming, which yielded a probe with an approximate specific activity of $2 \times 10^9$ dpm/μg. After hybridization, the membrane was washed three times in 2×SSC, 0.1% SDS at 65° C. for 20 minutes and exposed to film for 24 hours. In order to determine the approximate transfected CAT gene copy number, blots were alto hybridized with a 1.1 kb BSU 36-1 single copy probe from a mouse factor VIII-A genomic done (Levinson et al., Genomics (1992) 13: 862–865). Relative amounts of the CAT plasmid deposited in individual mouse lungs were quantitated by phosphorimagining analysis using a Molecular dynamics 400A phosphorimaginer (Johnson et al., Electrophoresis (1990) 11: 355–360). The mount of retained probe in each lane following hybridization with the CAT probe was normalized to the amount of DNA loaded per lane using the counts measured after hybridization with a Factor VIII-A single copy probe.

In Situ Immunochemical Staining for CAT enzyme.

At selected time points following aerosolization, mice were sacrificed and their lungs immediately removed. The lungs were slowly inflated with phosphate buffered saline (PBS) containing 33% by volume OCT (Miles, Inc.), placed in a tissue cassette filled with OCT, and frozen in 2-methylbutane chilled in a dry ice/ethanol bath. Cryosections were cut at 5 μm and collected onto salinized slides. CAT was detected after fixation of cryosections for 10 minutes in either 4% acetone or 2% paraformaldehyde in PBS containing 0.1% Tween 20 (PBST). All subsequent dilutions and washes were also done in PBST.

Following fixation, sections were washed three times (5 minutes each) then covered with 10% normal rabbit serum for 10 minutes at 20° C. The serum was replaced with diluted (1:500) rabbit polyclonal antibody against CAT (Drs. Parker Antin and David Standring, UCSF Medical Center). The antibody covered section was gently overlaid with a siliconized coverslip and incubated in a humid chamber at 4° C. for 24 hours. Slides were then warmed to 20° C. and washed three times. The presence of bound rabbit antibody against CAT was detected by covering sections with biotinylated, affinity purified, goat anti-rabbit antibody (Vector Laboratories) diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromogen, with endogenous alkaline phosphatase being inhibited with levamisole (Zymed). To control for potential spurious adherence of the streptavidin conjugate to bronchiolar epithelium, some sections were treated with free avidin and biotin prior to application of the primary antibody. Other controls, run concurrently, included the use of normal rabbit serum in place of primary antibody and the use of lung tissue from untreated mice. Photo-microscopy was performed using Kodak Ektachrome 64T film X50 (FIG. 6 A,D) and X250 (FIG. 6 B,C,E,F).

Result

Initially, mice were exposed either to an aerosol generated from a solution containing 12 mg of a CMV-CAT expression plasmid alone or to an aerosol generated from a solution containing 12 mg of CMV-CAT complexed to 24 μmoles of DOTMA:DOPE (1:1) liposomes. Aerosols were administered to animals after they were placed individually in nose-out cones and inserted into an Intox small animal exposure chamber. The mice showed no apparent ill effects or respiratory distress either during or after aerosol exposure. FIG. 7 shows the results of CAT assays from extracts of the lungs of mice sacrificed 72 hours following aerosol administration. Significant CAT gene expression was seen only in mice exposed to aerosolized DNA/liposome complexes.

How long CAT protein was present in the lungs of mice and whether expression of the reporter gene was limited to the lung was also investigated. Despite inter-animal variation, high levels of CAT activity are present for at least 21 days following a single aerosol dose of DNA/liposome complexes (FIG. 8A). No CAT activity was detectable in extracts from the heart, spleen, kidneys or liver of animals that showed high level expression in the lung (FIG. 8B), suggesting that transgene expression following aerosol delivery is restricted to the lung. This is consistent with prior observations showing that penetration of very high molecular weight substances through the respiratory epithelium of normal animals is very limited. Plasmid DNA/liposome complexes have molecular weights greater than $10^6$ daltons.

Although the small animal exposure chamber used in these experiments is designed to efficiently deliver a uniform aerosol dose to up to 48 animals, we have observed significant variations in the level of CAT activity in the lungs of mice within a single experiment. One possible explanation for this variability is that the amount of DNA/liposome complex deposited in the lungs of mice is not uniform. In order to test this hypothesis, initial lung deposition of liposomes was measured using fluorescence analysis and initial lung deposition of DNA was measured using Southern blot analysis.

Aerosolized cationic liposomes alone or DNA/liposome alone or DNA/liposome complexes containing 0.5 mole percent of a fluorescently labelled lipid, rhodamine-phosphatidylethanolamine, were administered to mice. Immediately following aerosolization, the animals were sacrificed and their lungs removed, homogenized and rhodamine fluorescence measured using a fluorimeter. The recovered fluorescence per animal was 0.06% ±0.02 (S.D.) of the total amount aerosolized. This suggests that less than 10 µg out of the 12 mg of DNA aerosolized per experiment was actually deposited in the lung. In addition, there was no significant difference in lipid deposition between animals receiving liposomes alone and those receiving the DNA/liposomes complexes. Since it is possible that a disruption of the complex could have occurred during nebulization, the amount of CAT gene deposited during aerosolization (FIG. 9) was also assessed. Immediately following aerosol delivery of DNA/liposome complexes, mice were sacrificed and total lung DNA prepared. Southern blots were probed with a $\alpha[^{32}P]$-labelled CAT gene. Labelled bands were scanned and demonstrated less than a 4-fold difference in plasmid deposition between animals in the same experiment (FIG. 9). These results suggest that the mouse to mouse variation in CAT gene levels following aerosol delivery (up to tenfold) is not only a function of the mount of complex initially deposited in the lung, but also may reflect differences in the site of uptake, rate of lung clearance, and/or variation in the ability of different lung cell types to express the transgene.

To determine the types and percentage of lung cells which were transfected in vivo, lungs of mice sacrificed 72 hours following exposure to an aerosol containing DNA/liposome complexes were cryosectioned, probed with a polyclonal anti-CAT antibody and counterstained to detect intracellular CAT protein (FIG. 6). Lung sections taken from DNA/liposome treated mice had a diffuse immunostaining pattern involving bronchiolar and alveolar components. The bronchiolar epithelial cytoplasm stained with greatest intensity and uniformity. CAT antigen was detected (as demonstrated by red staining) in nearly all conducting airways with only rare individual or 2–3 cell clusters not staining (FIG. 6A,B). The diffuse alveolar pattern was due to moderately intense staining of the majority of alveolar lining cells (FIG. 6C). These areas occasionally faded into small, randomly scattered regions where lining cell staining was faint. Focal, intense staining (arrows) occurred in the cytoplasm of scattered, individual, alveolar lining cells (FIG. 6C). Controls included substitution of the primary antibody with normal rabbit serum (FIG. 6D) and use of lung sections from untreated animals (FIG. 6 E,F). Immunostaining was not detectable in either of the control preparations. Examination of multiple sections of lung from treated and control mice demonstrated no significant lesions which would indicate adverse effects of the aerosol treatment.

Example III

High Level Airway Expression of the Human CFTR Gene in Mouse Lungs After Aerosol Administration of DDAB:Cholesterol Liposome-pZN32 Complexes Animals.

Two months old, female, ICR mice obtained from Simonsen, Gilroy, Calif., were used.

Preparation of plasmid DNA.

Figure 4A:
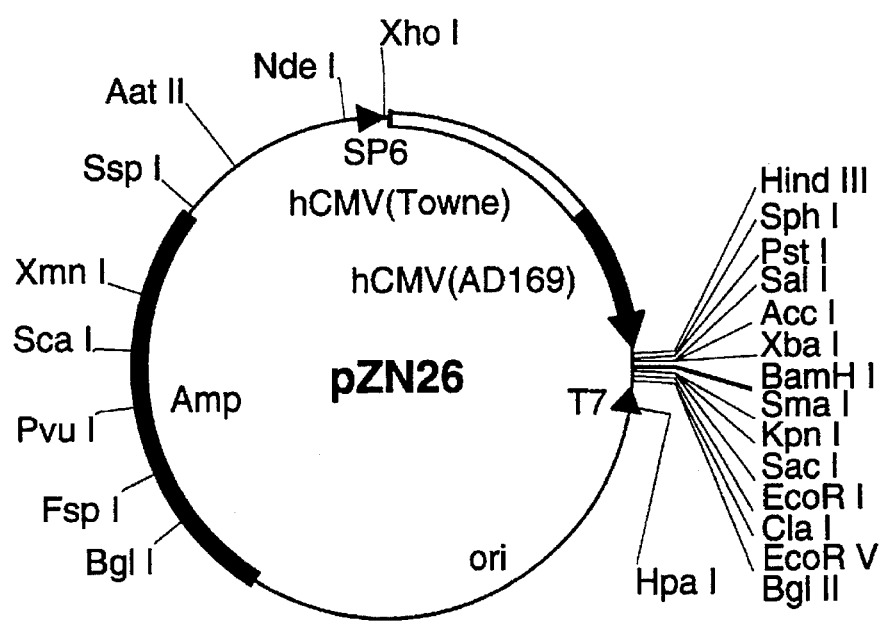
Figure 5:
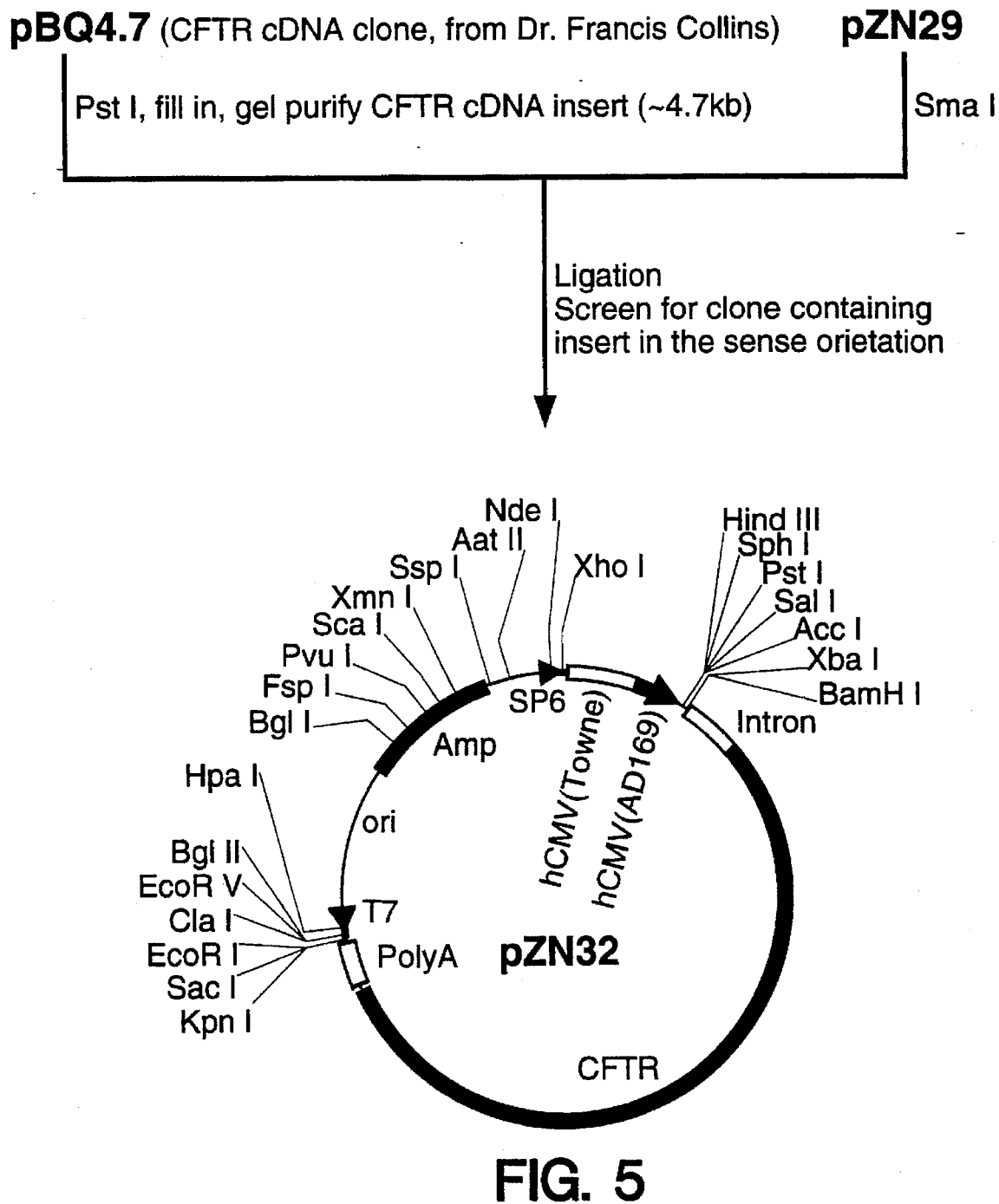
FIG. 5 show construction of pZN32.
Figure 6A:
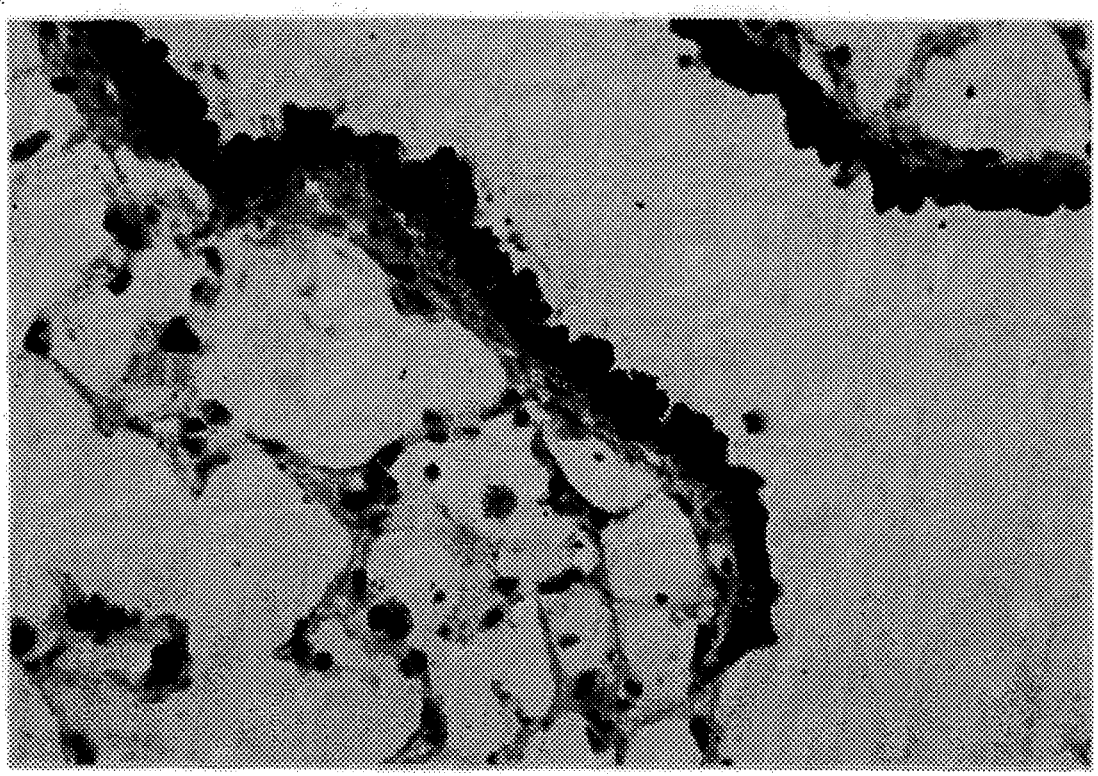
Figure 6B:
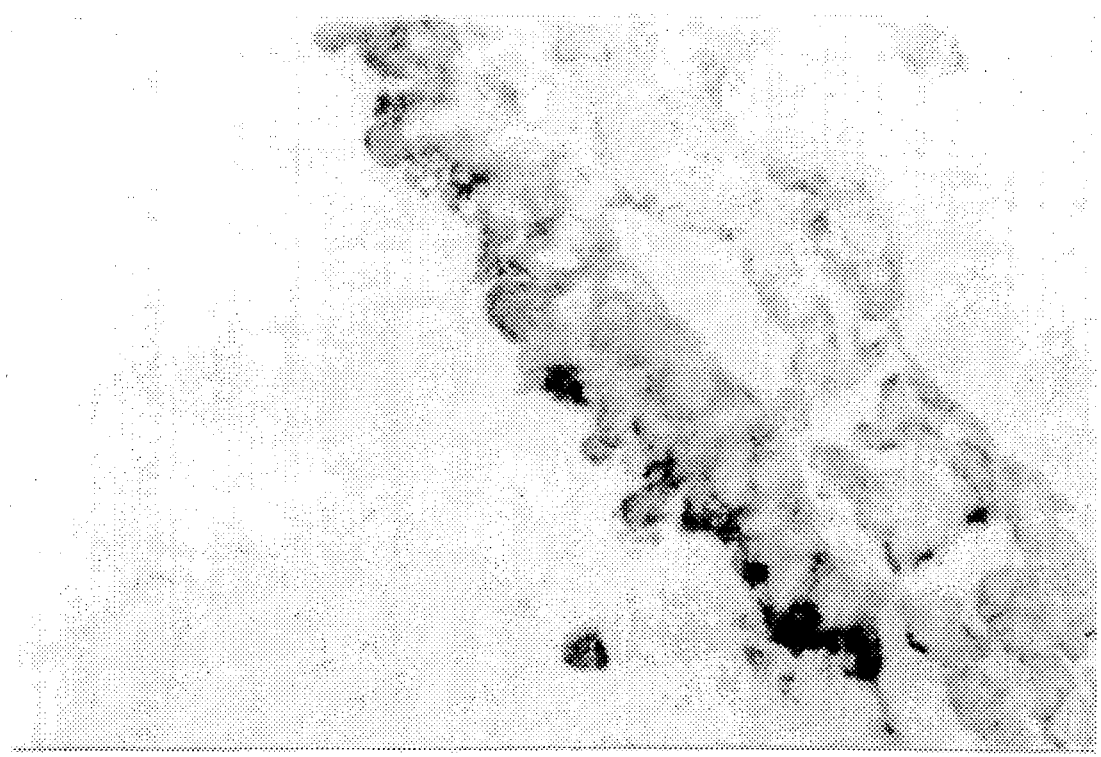
Figure 6C:
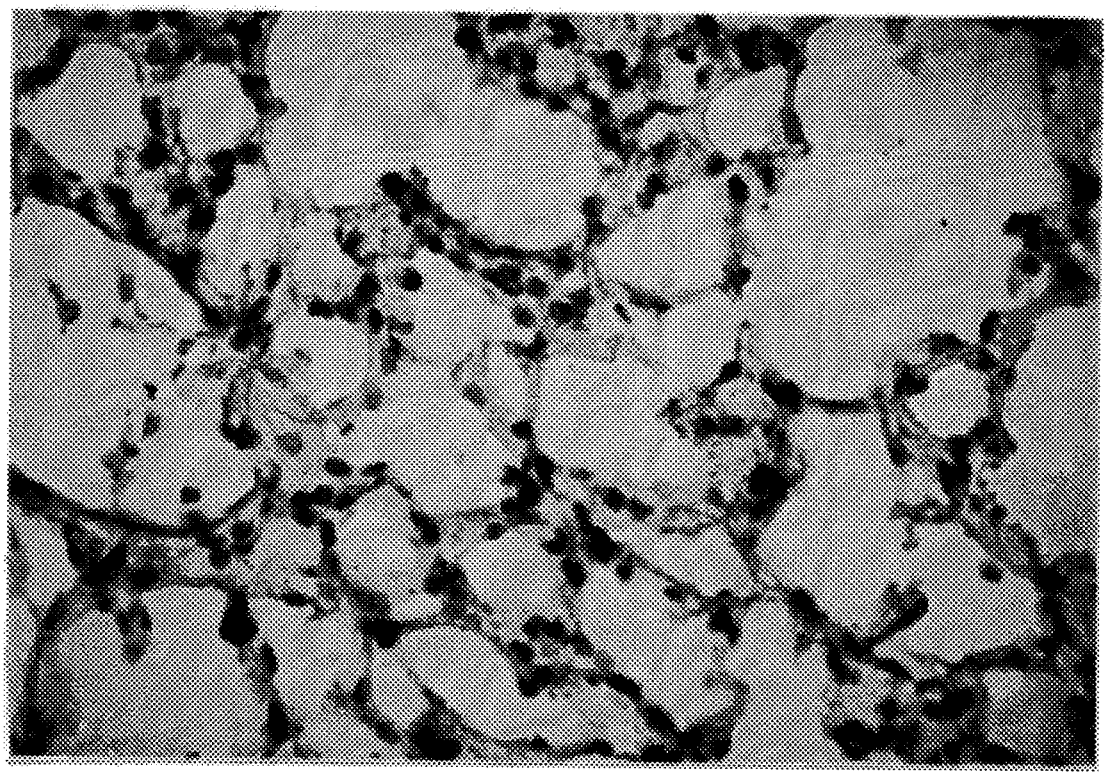
Figure 6D:
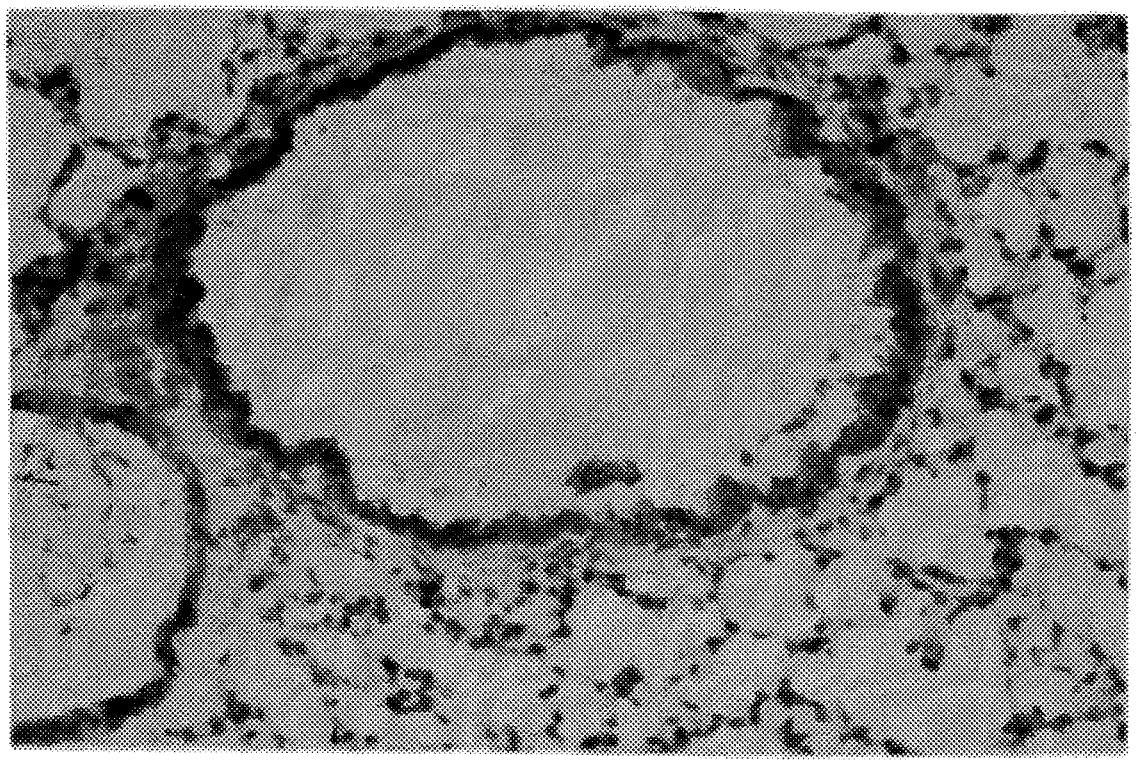
Figure 6E:
Figure 6F:
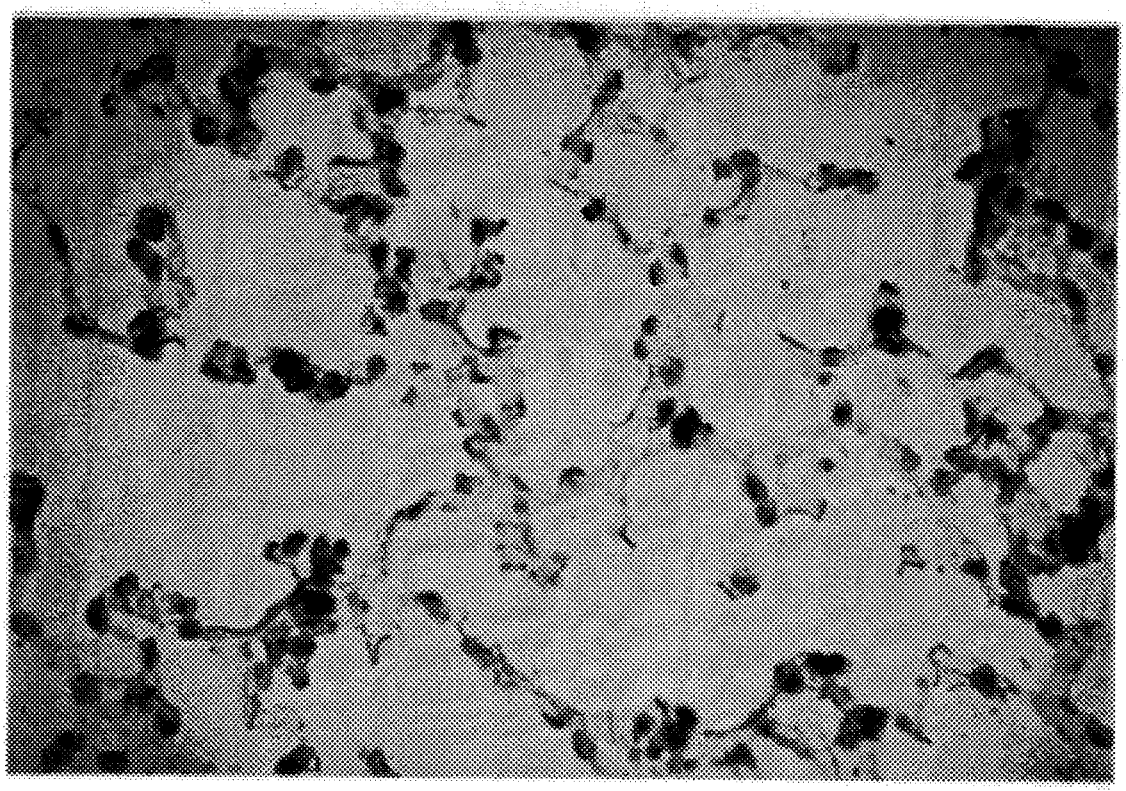

The plasmid liposome used, pZN32, contains the human CFTR gene coding region fused to the human cytomegalovirus immediate early promoter-enhancer element shown in FIGS. 3–5 attached hereto. A full restriction map of the immediate early enhancer and promoter region of HCMV (Towne) and HCMV (AD169) is provided in FIGS. 11A and 11C. The two sequences are compared in FIG. 11B. pZN32 was purified using alkaline lysis and ammonium acetate precipitation, and the nucleic acid concentration measured by UV absorption at 260 nm.

Preparation of cationic lipid carriers.

Lipid carriers were prepared as small unilamellar vesicles (approximately 100 nm in diameter) containing the cationic lipid DDAB (dimethyl dioctadecyl ammonium bromide) as DDAB cholesterol in a 1:1 molar ratio. DDAB was purchased from Sigma, St. Louis, Mo., and cholesterol was purchased from CalBioChem, San Diego, Calif. Stock solutions of the lipids were dissolved in chloroform. Lipids were mixed in a round-bottomed flask and evaporated to dryness on a rotary evaporator under reduced pressure. Double distilled water was added to produce final lipid concentrations of 10 mM each, and the resulting mix was sonicated for approximately 20 minutes in a bath sonicator (Laboratory Supplies, Hicksville, N.Y.).

Aerosol delivery of plasmid/lipid carrier complexes to mice.

Twelve mg of pZN32 complexed to 24 µmols of DDAB:cholesterol (1:1 mole ratio) liposomes was aerosolized over two different aerosol periods on the same day. To prevent aggregation and precipitation of the oppositely charged components, the liposomes and DNA were diluted separately in sterile water prior to mixing. Six mg of plasmid DNA and 12 µmols of DDAB:cholesterol (1:1 mole ratio) liposomes were each diluted to 8 ml with water and mixed. Eight ml of the DNA-liposome mixture was then placed into each of two Acorn I nebulizers (Marquest, Englewood, Colo.), and the animals placed in an Intox small animal exposure chamber (Albuquerque, N.Mex.). An air flow rate of 4 L min$^{-1}$ was used to generate the aerosol. Ninety minutes were required to aerosolize this volume (16 ml) of DNA-liposome mixture. The animals were removed from the chamber for 1–2 hours and then the above procedure was repeated with a second 16 ml dose.

Immunohistochemical staining for the human CFTR protein in mouse lungs.

At selected time points following aerosolization, mice were sacrificed and their lungs immediately removed. The lungs were slowly inflated with phosphate buffered saline (PBS) containing 3.3% by volume OCT (Miles, Inc.), then placed in a tissue cassette filled with OCT, and frozen in 2-methylbutane chilled in a dry ice/ethanol bath. Cryosections were cut at 5 µm and collected onto sialinized slides. CFTR protein was detected after fixation of cryosections for 10 minutes in either 4% acetone or 2% paraformaldehyde in PBS containing 0.1% Tween 20 (PBST). All subsequent dilutions and washes were done in PBST. Following fixation, sections were washed three times (5 minutes each) with PBST then covered with 10% normal rabbit serum for 10 minutes at 20° C. Immunolocalization of CFTR was then performed using an affinity purified rabbit polyclonal anti-CFTR antibody, $\alpha$-1468, provided by Dr. Jonathan Cohn, Duke University. The serum was replaced with $\alpha$-468, diluted (1:1000). The antibody-covered section was gently overlaid with a siliconized coverslip and incubated in a humid chamber at 4° C. for 24 hours. Slides were then warmed to 20° C. and washed three times. The presence of bound rabbit antibody against CFTR was detected by covering sections with biotinylated, affinity-purified, goat anti-rabbit antibody (Lipid carrier Laboratories), diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromogen; endogenous alkaline phosphatase was inhibited with levamisole (Zymed). Other controls, run concurrently, included the use of normal rabbit serum in place of primary antibody and the use of lung tissue from untreated mice. Photo-microscopy was performed using Kodak Ektachrome 64T film at X50 and X250.

Results.

Photomicrographs of frozen sections (viewed at different magnifications) of mouse lung 48 hours following aerosol exposure to pZN32-DDAB:cholesterol 1:1 mole ratio liposome complexes and lung from untreated control are shown in FIGS. 10A–10E. As demonstrated by the intense staining with the polyclonal anti-CFTR antibody, α-1468, the overwhelming majority of the airways were transfected with the human CFTR gene. See FIGS. 10A, 10C and 10E. By visual inspection, essentially all the cells in transfected airways stain positively, demonstrating that the overwhelming majority of airway cells are transfected with the human CFTR gene in vivo with a single aerosol dose of pZN32 complexed to DDAB-cholesterol 1:1 mole ratio liposomes. Representative sections are shown in FIG. 10. There was no histologic evidence of lung damage, inflammation or edema present in any of the pZN32-DDAB:cholesterol-1:1 mole ratio liposome-treated animals. pZN32-DDAB:cholesterol 1:1 mole ratio liposome-treated and control animals could not be distinguished histologically. Significant expression of the human CFTR gene is present in at least 50% of all the airways and at least 50% of all of the airway lining cells (by visual inspection) in mouse lungs for at least 60 days following a single aerosol dose of pZN32 complexed to DDAB-cholesterol 1:1 mole ratio liposomes. Frozen sections of mouse lungs from control animals (FIGS. 10B and 10D) do not show any detectable staining for CFTR, confirming that all the CFTR expression present in FIG. 10A, 10C and 10E is due to transfection of lung cells with the human CFTR gene.

Example IV

Efficient Transfection of a Variety of Human Lung Cancer Cell Lines Using Cationic Liposome-Mediated Delivery of DNA.

Method:
Cell Culture:
NCl-H69, NCl-H82, and NCI-H520. H69 and H520 cells were grown in RPMI-1640 with 10% fetal bovine serum (FBS) and H82 cells were grown in Dulbecco's minimum essential medium (DME)-H21 with 10% FBS.
Liposome preparation:
Liposomes were prepared as follows: a total of 4 μmoles of lipid dissolved in chloroform, (or in ethanol (DOTMA)) were evaporated to dryness on a rotary evaporator. One ml of 50 mM Tris, 0.5 mM EDTA, 50 mM NaCl, 100 mM $ZnCl_2$ buffer per 20 mmoles of lipid was added, and the mixture was sonicated in a bath sonicator (Laboratory Supply Co., Hicksville, N.Y.) for 20 min. The resulting liposomes have an approximate mean diameter of 100±25 nm. The following liposome preparations were used: pure DOTMA, DOTMA:chol in a 2 to 1 molar milo, pure L-PE or L-PE:chol-b-ala in a 6 to 4 molar ratio.

Cellular transfection:

For transfection of cells, $2 \times 10^6$ cells in 4 ml of serum-free medium were plated in 100 mm plastic petri dishes (Falcon, Oxnard, Calif.). The plasmid DNA-liposome complex was prepared by first adding 1) DNA and then 2), liposomes and mixing gently. The complex was then suspended in 1 ml of serum-free medium and added to the cells. Four hours later, the cells were washed twice, resuspended in 10 ml of serum-containing medium, and subsequently harvested, either 44 hours later. Just prior to harvesting, the cells were washed 2 times, and the plates were then scraped with a rubber policeman. The cells were centrifugated at 1,000 ×g for 5 min, and 0.135 ml of 0.25M Tris buffer was added to each pellet. The cells were freeze-thawed 3×, heated at 65° C. for 10 min, and spun at 12,500 ×g for 10 min. The supernatant was assayed for protein and 20 μg of supernatant protein per sample was used to measure CAT activity, as described above.

Results:

The ability of cationic liposomes to mediate transfection of two different human small cell lung cancer lines (H-69 and H-82) and a squamous cell lung cancer line (H-520) was assessed. All three lines were very efficiently transfected by RSV-CAT when complexed to 3 different cationic liposome formulations. These human cell lines were either as or more efficiently transfected than rodent cell lines transfected under comparable conditions.

As shown by the above results, a single aerosol dose of an expression liposome, containing a gene of interest, complexed to cationic liposomes transfects the majority of the cells lining both the conducting airways and the alveoli of the lung, the gene product is present in the lung for at least 60 days, the expression appears to be lung-specific, and there is no histological evidence of damage following exposure. Thus, the aerosolized cationic liposomes mediate efficient transfection of non-dividing as well as dividing cells. This is important because many airway epithelial cells are well differentiated and divide slowly or not at all. The lipid carriers appear to be both well tolerated and non-immunogenic. Additionally, the effects of repeated aerosol administration of the DNA/liposome complexes is effective and is non-toxic. The cationic liposome-mediated DNA delivery by aerosol provides high level, lung-specific transgene expression in vivo.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising:

a nebulized transfection agent, prepared by nebulizing a mixture comprising complexes between DNA molecules comprising expression cassettes and cationic lipid carriers in a pharmaceutically acceptable carrier, wherein the cationic lipid carriers are in the form of vesicles having diameter of about 100–500 nm, wherein said expression cassettes and said cationic lipid carriers are present in said mixture in a ratio ranging from about 4:1 to about 1:2 mg DNA to micromole of cationic lipid, wherein said mixture is substantially free of macroaggregates of said complexes, and wherein said expression cassettes comprise a DNA sequence that is transcribed to produce a transcription product in vivo in a mammalian lung cell transfected by said nebulized transfection agent.

2. The composition according to claim 1, wherein said DNA sequence comprises an inducible promoter.

3. The composition according to claim 2, wherein said inducible promoter is a cell specific promoter, a tissue specific promoter or a hormone responsive promoter.

4. The composition according to claim 2, wherein said DNA sequence comprises an SV40 enhancer element whereby transcription from said promoter is enhanced.

5. A method of transfecting mammalian lung cells in vivo and obtaining synthesis of a polypeptide in said cells, said method comprising contacting said cells with a sufficient amount of a nebulized composition according to claim 1 to produce transfected cells that synthesize said polypeptide.

6. The method according to claim 5, wherein said lung cells are distal airway cells or proximal airway cells.

7. The method according to claim 5, wherein said lung cells are tracheal cells.

8. The method according claim 5, wherein said lung cells are normal lung cells.

9. The composition according to claim 1, wherein said cationic lipid carriers are small unilamellar vesicles.

10. The composition according to claim 9, wherein said small unilamellar vesicles comprise (a) dioleoylphosphatidylethanolamine (DOPE) and N[1-2,3-dioleyloxy)propyl]-N,N,N-triethylammonium (DOTMA) or (b) dimethyldioctadecylammoniumbromide (DDAB) and cholesterol.

11. The composition according to claim 1, wherein said expression cassettes and said cationic lipid carriers are present in said mixture in a ratio in the range of from about 1:1 to 1:2 mg DNA to μmol of cationic lipid.

12. The composition according to claim 1, wherein said cationic lipid carrier comprises a lipid selected from the group consisting of N[1-2,3-dioleyloxy)propyl]-N,N,N-triethylammonium (DOTMA); dimethyl dioctadecyl ammonium bromide (DDAB); 1,2-dioleyloxy-3-(trimethylammonio) propane (DOTAP); lysinylphosphatidyl-ethanolamine (L-PE); dioleoylphosphatidylethanolamine (DOPE); and cholesterol.

13. The composition according to claim 1, wherein said cationic lipid carrier comprises cholesterol and a lipid selected from the group consisting of N[1-2,3-dioleyloxy)propyl]-N,N,N-triethylammonium (DOTMA); dimethyldioctadecylammoniumbromide (DDAB); 1,2-dioleyloxy-3-(trimethylammonio)propane (DOTAP); and lysinylphosphatidyl-ethanolamine (L-PE).

14. The composition according to claim 1, wherein said cationic lipid carrier comprises dioleoylphosphatidylethanolamine (DOPE) and a lipid selected from the group consisting of N[1-2,3-dioleyloxy)propyl]-N,N,N-triethylammonium (DOTMA); dimethyldioctadecylammoniumbromide (DOTAP); 1,2-dioleoyloxy-3-(trimethylammonio)propane (DOTAP); and lysinylphosphatidyl-ethanolamine (L-PE).

15. A method for transfecting cells lining conducting airways and alveoli of a mammalian lung, said method comprising:

introducing a sufficient amount of a composition according to claim 1 into said lung via intraoral or intranasal delivery to transfect said airways and said alveoli.

* * * * *

SEQUENCE LISTING ( 1 ) GENERAL INFORMATION:

( i i i ) NUMBER OF SEQUENCES: 4

(2) INFORMATION FOR SEQ ID NO: 1:

(i) SEQUENCE CHARACTERISTICS:
        (A) LENGTH: 616
        (B) TYPE: nucleic acid
        (C) STRANDEDNESS: single
        (D) TOPOLOGY: linear (xi) SEQUENCE DESCRIPTION: SEQ ID NO: 1:

| | | | | | | |
|---|---|---|---|---|---|---|
| GGCGACCGCC | CAGCGACCCC | CGCCCGTTGA | CGTCAATAGT | GACGTATGTT | CCCATAGTAA | 60 |
| CGCCAATAGG | GACTTTCCAT | TGACGTCAAT | GGGTGGAGTA | TTTACGGTAA | ACTGCCTACT | 120 |
| TGGCAGTACA | TCAAGTGTAT | CATATGCCAA | GTCCGCCCCC | TATTGACGTC | AATGACGGTA | 180 |
| AATGGCCCGC | CTAGCATTAT | GCCCAGTACA | TGACCTTACG | GGAGTTTCCT | ACTTGGCAGT | 240 |
| ACATCTACGT | ATTAGTCATC | GCTATTACCA | TGGTGATGCG | GTTTTGGCAG | TACACCAATG | 300 |
| GGCGTGGATA | GCGGTTTGAC | TCACGGGGAT | TTCCAAGTCT | CCACCCCATT | GACGTCAATG | 360 |
| GGAGTTTGTT | TTGGCACCAA | AATCAACGGG | ACTTTCCAAA | ATGTCGTAAT | AACCCCGCCC | 420 |
| CGTTGACGCA | AATGGGCGGT | AGGCGTGTAC | GGTGGGAGGT | CTATATAGCA | GAGCTCGTTT | 480 |
| AGTGAACCGT | CAGATCGCCT | GGAGACGCCA | TCCACGCTGT | TTTGACCTCC | ATAGAAGACA | 540 |
| CCGGGACCGA | TCCAGCCTCC | GCGGCCGGGA | ACGGTGCATT | GGAACGCGGA | TTCCCCGTGC | 600 |
| CAAGAGTGAC | GTAAGT | | | | | 616 |

(2) INFORMATION FOR SEQ ID NO: 2:

(i) SEQUENCE CHARACTERISTICS:
        (A) LENGTH: 930
        (B) TYPE: nucleic acid
        (C) STRANDEDNESS: single
        (D) TOPOLOGY: linear (xi) SEQUENCE DESCRIPTION: SEQ ID NO: 2:

| | | | | | | |
|---|---|---|---|---|---|---|
| AATCAATATT | GGCCATTAGC | CATATTATTC | ATTGGTTATA | TAGCATAAAT | CAATATTGGC | 60 |
| TATTGGCCAT | TGCATACGTT | GTATCCATAT | CATAATATGT | ACATTTATAT | TGGCTCATGT | 120 |
| CCAACATTAC | CGCCATGTTG | ACATTGATTA | TTGACTAGTT | ATTAATAGTA | ATCAATTACG | 180 |
| GGGTCATTAG | TTCATAGCCC | ATATATGGAG | TTCCGCGTTA | CATAACTTAC | GGTAAATGGC | 240 |
| CCGCCTGGCT | GACCGCCCAA | CGACCCCCGC | CCATTGACGT | CAATAATGAC | GTATGTTCCC | 300 |
| ATAGTAACGC | CAATAGGGAC | TTTCCATTGA | CGTCAATGGG | TGGAGTATTT | ACGGTAAACT | 360 |
| GCCCACTTGG | CAGTACATCA | AGTGTATCAT | ATGCCAAGTA | CGCCCCCTAT | TGACGTCAAT | 420 |
| GACGGTAAAT | GGCCCGCCTG | GCATTATGCC | CAGTACATGA | CCTTATGGGA | CTTTCCTACT | 480 |
| TGGCAGTACA | TCTACGTATT | AGTCATCGCT | ATTACCATGG | TGATGCGGTT | TTGGCAGTAC | 540 |
| ATCAATGGGC | GTGGATAGCG | GTTTGACTCA | CGGGGATTTC | CAAGTCTCCA | CCCCATTGAC | 600 |
| GTCAATGGGA | GTTTGTTTTG | GCACCAAAAT | CAACGGGACT | TCCAAAATG | TCGTAACAAC | 660 |
| TCCGCCCCAT | TGACGCAAAT | GGGCGGTAGG | CGTGTACGGT | GGGAGGTCTA | TATAAGCAGA | 720 |
| GCTCGTTTAG | TGAACCGTCA | GATCGCCTGG | AGACGCCATC | CACGCTGTTT | TGACCTCCAT | 780 |
| AGAAGACACC | GGGACCGATC | CAGCCTCCGC | GGCCGGGAAC | GGTGCATTGG | AACGCGGATT | 840 |
| CCCCGTGCCA | AGAGTGACGT | AAGTACCGCC | TATAGAGTCT | ATAGGCCCAC | CCCCTTGGCT | 900 |
| TCTTATGCAT | GCTATACTGT | TTTTGGCTTG | | | | 930 |

(2) INFORMATION FOR SEQ ID NO: 3:

(i) SEQUENCE CHARACTERISTICS:
        (A) LENGTH: 616

( B ) TYPE: nucleic acid
        ( C ) STRANDEDNESS: single
        ( D ) TOPOLOGY: linear ( x i ) SEQUENCE DESCRIPTION: SEQ ID NO: 3:

```
GGCGACCGCC  CAGCGACCCC  CGCCCGTTGA  CGTCAATAGT  GACGTATGTT  CCCATAGTAA      60
CGCCAATAGG  GACTTTCCAT  TGACGTCAAT  GGGTGGAGTA  TTTACGGTAA  ACTGCCCACT     120
TGGCAGTACA  TCAAGTGTAT  CATATGCCAA  GTCCGCCCCC  TATTGACGTC  AATGACGGTA     180
AATGGCCCGC  CTAGCATTAT  GCCCAGTACA  TGACCTTACG  GGAGTTTCCT  ACTTGGCAGT     240
ACATCTACGT  ATTAGTCATC  GCTATTACCA  TGGTGATGCG  GTTTTGGCAG  TACACCAATG     300
GGCGTGGATA  GCGGTTTGAC  TCACGGGGAT  TTCCAAGTCT  CCACCCCATT  GACGTCAATG     360
GGAGTTTGTT  TTGGCACCAA  AATCAACGGG  ACTTTCCAAA  ATGTCGTAAT  AACCCCGCCC     420
CGTTGACGCA  AATGGGCGGT  AGGCGTGTAC  GGTGGGAGGT  CTATATAGCA  GAGCTCGTTT     480
AGTGAACCGT  CAGATCGCCT  GGAGACGCCA  TCCACGCTGT  TTTGACCTCC  ATAGAAGACA     540
CCGGGACCGA  TCCAGCCTCC  GCGGCCGGGA  ACGGTGCATT  GGAACGCGGA  TTCCCCGTGC     600
CAAGAGTGAC  GTAAGT                                                         616
```

( 2 ) INFORMATION FOR SEQ ID NO: 4:

( i ) SEQUENCE CHARACTERISTICS:
        ( A ) LENGTH: 930
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
AATCAATATT  GGCCATTAGC  CATATTATTC  ATTGGTTATA  TAGCATAAAT  CAATATTGGC      60
TATTGGCCAT  TGCATACGTT  GTATCCATAT  CATAATATGT  ACATTTATAT  TGGCTCATGT     120
CCAACATTAC  CGCCATGTTG  ACATTGATTA  TTGACTAGTT  ATTAATAGTA  ATCAATTACG     180
GGGTCATTAG  TTCATAGCCC  ATATATGGAG  TTCCGCGTTA  CATAACTTAC  GGTAAATGGC     240
CCGCCTGGCT  GACCGCCCAA  CGACCCCGC  CCATTGACGT  CAATAATGAC  GTATGTTCCC     300
ATAGTAACGC  CAATAGGGAC  TTTCCATTGA  CGTCAATGGG  TGGAGTATTT  ACGGTAAACT     360
GCCCACTTGG  CAGTACATCA  AGTGTATCAT  ATGCCAAGTA  CGCCCCCTAT  TGACGTCAAT     420
GACGGTAAAT  GGCCCGCCTG  GCATTATGCC  CAGTACATGA  CCTTATGGGA  CTTTCCTACT     480
TGGCAGTACA  TCTACGTATT  AGTCATCGCT  ATTACCATGG  TGATGCGGTT  TTGGCAGTAC     540
ATCAATGGGC  GTGGATAGCG  GTTTGACTCA  CGGGGATTTC  CAAGTCTCCA  CCCCATTGAC     600
GTCAATGGGA  GTTTGTTTTG  GCACCAAAAT  CAACGGGACT  TTCCAAAATG  TCGTAACAAC     660
TCCGCCCCAT  TGACGCAAAT  GGGCGGTAGG  CGTGTACGGT  GGGAGGTCTA  TATAAGCAGA     720
GCTCGTTTAG  TGAACCGTCA  GATCGCCTGG  AGACGCCATC  CACGCTGTTT  TGACCTCCAT     780
AGAAGACACC  GGGACCGATC  CAGCCTCCGC  GGCCGGGAAC  GGTGCATTGG  AACGCGGATT     840
CCCCGTGCCA  AGAGTGACGT  AAGTACCGCC  TATAGAGTCT  ATAGGCCCAC  CCCCTTGGCT     900
TCTTATGCAT  GCTATACTGT  TTTTGGCTTG                                         930
```